United States Patent
Constantini et al.

(10) Patent No.: US 6,307,019 B1
(45) Date of Patent: Oct. 23, 2001

(54) AXIN GENE AND USES THEREOF

(75) Inventors: Franklin Constantini; Li Zeng, both of New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/890,865

(22) Filed: Jul. 10, 1997

(51) Int. Cl.$^7$ .......................... C07K 14/00; C07H 21/02; C07H 21/04; C12P 21/06

(52) U.S. Cl. .................. 530/350; 536/23.1; 536/23.5; 536/24.5; 435/69.1; 435/320.1; 435/325; 435/252; 435/1; 435/254.2

(58) Field of Search ............................ 536/23.1, 23.5, 536/24.5; 435/69.1, 320.1, 325, 252.1, 254.2; 530/350

(56) References Cited

PUBLICATIONS

Mayr, T. et al., Mech. Develop., vol. 63, pp. 109–125, Apr. 1997.*

Wagner, R., Nature, vol. 372, pp. 333–335, Nov. 1994.*

Zeng, L. et al., Cell, vol. 90, pp. 181–192, Jul. 1997.*

Carnac, G., et al. (1996) "The homeobox gene Siamois is a target of the Wnt dorsalization pathway and triggers organizer activity in the absence of mesoderm." *Development* 122: 3055–3065.

Conlon, F., and Beddington, R. (1995) "Mouse gastrulation from a frog's perspective." *Semin. Dev. Biol.* 6: 249–256.

Fagotto, F., et al. (1996) "Binding to cadherins antagonizes the signaling activity of beta–catenin during axis formation in Xenopus." *J. Cell. Biol.* 132: 1105–1114.

Fagotto, F., et al. (1997) "Induction of the primary dorsalizing center in Xenopus by the Wnt/GSK/β–catenin signaling pathway, but not by Vgl, Activin, or Noggin." *Development* 124: 453–460.

Fagotto, F., and Gumbiner, B.M. (1994) "Beta–catenin localization during Xenopus embryogenesis: accumulation at tissue and somite boundaries." *Development* 120: 3667–3679.

Gluecksohn–Schoenheimer, S. (1949) "The effects of a lethal mutation responsible for duplications and twinning in mouse embryos." *J. Exp. Zool.* 110: 47–76.

Hopppler, S., et al. (1996) "Expression of a dominant–negative Wnt blocks induction of MyoD in Xenopus embryos." *Genes Dev* 10: 2805–2817.

Jacobs–Cohen, R.J., et al. (1984) "Knobby, a new dominant mutation in the mouse that affects embryonic ectoderm organization." *Genet. Res.* 43: 43–50.

Miller, J.R., and Moon, R.T. (1996) "Signal transduction through β–catenin and specification of cell fate during embryogenesis." *Genes Dev* 10: 2527–2539.

Morin, P.J., et al. (1997) "Activation of beta–catenin–Tcf signaling in colon cancer by mutations in beta–catenin or APC." *Science* 275: 1787–1790.

Nusse, R. (1992) The Wnt gene family in tumorgenesis and in normal development [Review]. *J. Steroid Biochem. Mol. Biol.* 43: 9–12.

Nusse, R., and Varmus, H.E. (1992) "Wnt genes." *Cell* 69: 1073–1087.

Reifer, M. (1997) "Beta–catenin as oncogene: the smoking gun." Science 275: 1752–1753.

Perry, W.L., et al. (1995) "Phenotypic and molecular analysis of a transgenic insertional allele of the mouse fused locus." *Genetics* 141: 321–332.

Polakis, P. (1997) "The adenomatous polyposis coli (APC) tumor suppressor." *Biochem. Biophys. Acta.* 1332: F127–147.

Rubinfeld, B., et al. (1996) "Binding of GSK3 to the APC–β–catenin complex and regulation of complex assembly." *Science* 272: 1023–1026.

Tilghman, S.M. (1996) "Lessons learned, promises kept: a biologist's eye view of the Genome Project." *Genome Res.* 6: 773–780.

Wylie, C., et al. (1996) "Maternal beta–catenin establishes a 'dorsal signal' in early Xenopus embryos." *Development* 122: 2897–2996.

* cited by examiner

*Primary Examiner*—Ponnathapu Achutamurthy
*Assistant Examiner*—Peter P. Tung
(74) *Attorney, Agent, or Firm*—John P. White; Cooper & Dunham LLP

(57) ABSTRACT

This invention provides an isolated nucleic acid which encodes Axin. This invention further provides an isolated nucleic acid which encodes a polypeptide comprising the amino acid sequence of Axin. This invention further provides a purified wildtype or mutant Axin. This invention further provides an oligonucleotide capable of distinguishing nucleic acids encoding mutant or wildtype Axin. This invention also provides various methods of use: such as a method for determining whether a subject carries a mutation in the axin gene, a method of determining whether a subject has a predisposition for cancer, a method for treating a subject who has a predisposition to cancer, a method for determining whether a subject has cancer, a method for detecting a mutation in cancerous cells of the subject, a method of suppressing cells unable to regulate themselves and a method for identifying a chemical compound which is capable of suppressing cells unable to regulate themselves. This invention also provides a variety of pharmaceutical compositions and a method of treating a subject who has cancer comprising administration the pharmaceutical compositions. This invention also provides a transgenic, nonhuman mammal, specifically a transgenic expressing mutant Axin.

22 Claims, 27 Drawing Sheets

FIGURE 3A

```
m   1   LGSGSRLREALAAAAGACWGRAGAWFQRGLVRVSSRFWRRSAACLAPPPGHGSPSRRRR m  61   RDGGPPGPRPRRGPPAEPPLSAWASPGREPGPGPRLHSRRALERLIPLGAVSTEVLGCSA
                                       1 GPGSRHH--RARDRLIHFGAVSTDVLGCSA
                                                        1 DFGSSP
                *          *
m 121   HCSLMQSPKMNVQEQGFPLDLGASFTEDAPRPPVPGEEGELVSTDSRPVNHSFCSGKGTS
h  29   HCSLTQSPKMNIQEQGFPLDLGASFTEDAPRPPVPGEEGELVSTDPRPASYSFCSGKGVG
c   7   AVQT SAR-KMNIQGKGFPLDLGRSFTEDAPRPPVPGEEGELVSTDPRPVSHGFYSSKSDA m 181   IKSETSTATPRRSDLDLGYEPEGSASPTPPYLRWAESLHSLLDDQDGISLFRTFLKQEGC
h  89   IKGETSTATPRRSDLDLGYEPEGSASPTPPYLKWAESLHSLLDDQDGISLFRTFLKQEGC
c  66   VRNETSTATPRRSDLDLGYEPEGSASPTPPYLKWAESLHSLLDDQDGINLFRTFLKQEDC m 241   ADLLDFWFACSGFRKLEPCDSNEEKRLKLARATYRKYILDSNGIVSRQTKPATKSFIKDC
h 149   ADLLDFWFAQIDGFRKLEPCDSNEEKRLKLARATYRKYILDNNGIVSRQTKPATKSFIKDC
c 126   ADLLDFWFACSGFRKLEPCVSNEEKRLKLAKATYRKAIYKKYILDNNGIVSRQTKPATKSFIKGC m 301   VMKQQIDPAMFDQAQTEIQSTMEENTYPSFLKSDIYLEVTRTGSESPKVCSDQSSGSGTG
h 209   IMKQLIDPAMFDQAQTEIQATMEENTYPSFLKSDIYLEVTRTGSESPKVCSDQSSGSGTG
c 186   VMKLQIDPDMFDQAQTEIQCMIEDNTYPLFLKSDIYLEVTRTGGESPKITYSDPSSGSGTG m 361   KGMSGYLPTLNEDEEWKCDQDADEDDGRDPLPPSRLTQKLLLETAAPRAPSSRRYNEGRE
h 269   KGISGYLPTLNEDEEWKCDQDMDEDDGRDAAPPGRLPQKLLLETAAPRVSSSRRYSEGRE
c 246   KGLPGYLPTLNEDEEWKCDQDTPEASRDSAPSSRLTQKLLLETATQRATSTRRYSEGRE m 421   LRYGSWREPVNPYYVNSGYALAPATSANDSEQQSLSSDADTLSLTDSSVDGIPPYRIRKQ
h 329   FRYGSWREPVNPYYVNAGYALAPATSANDSEQQSLSSDADTLSLTDSSVDDIPPYRIRKQ
c 306   FRHGSWREPVNPYYVNTGYAMAPATSANDSEQQSMSSDADTMSLTDSSIDGIPPYRLRKQ m 481   HRREMQESIQVNGRVPLPHIPRTYRMPKEIRVEPQKFAEELIHRLEAVQRTREAEEKLEE
h 389   HRREMQESAQVNGRVPLPHIPRTYRVPKEVRVEPQKFAEELIHRLEAVQRTREAEEKLEE
c 366   HRREMQESAKANGRVPLPHIPRTYRMPKDTHVEPEKFAAELINRLEEVQKEREAEEKLEE
```

FIGURE 3B

```
m 541  RLKRVRMEEEGEDGEMPSGP-MASHKLPSVPAWHHFPPRY-VDMGCSGL---RDAHEENPE
h 449  RLKRVRMEEEGEDGDPSSGPPGPCHKLPPAPAWHHFPPRLCWTWACAGL---RDAHEENPE
c 426  RLKRVRAEEEGEDADISSGPSVISHKMPSAQPFHHFAPRY-SEMGCAGMQMRDAHEENPE m 597  SILDEHVQRVMRTPGCQSPGPG-H----RSPDSGHVAKT-AVLGGTASGHGKHVPKLGLK
h 507  SILDEHVQRVLRTIGBQSPGPG-H----RSPDSGHVAKMPVALGGAASGHGKHVPKSGAK
c 485  SILDEHVQRVMKTPGCQSPGPGRIHSPKPRSPESGHLGKLSGTLGTIPPGHGKHTTKSGMK m 651  LDTAGLHHHRHVHHHVHHNSAR-PKEQMEAEVARRVQSSFSWGPETHGHAK-PRSYSENA
h 562  LDAAGLHHHRHVHHHVHHSTAR-PKEQVEAEATRRAQSSFAWGLEPHSHGARSRGYSESV
c 545  LDAANLYHKHVYHHIHHHSMMKPKEQIEAEATQRVQNSFAWNVDSHNYATKSRNYSENL m 709  GTTLSAGD-LAFGGKTSAPSKRNTKKAESGKN---ANAEVPSTTEDAEKNQKIMQWIIEGE
h 621  GAAPNASDGLAHSGKVGVACKRNAKKAESGKS---ASTEVPGASEDAEKNQKIMQWIIEGE
c 605  GMAPVPMDSLGYSGKASLLSKRNIKKTDSGKSDGANYEMPGSPEDVERNQKILQWIIEGE m 766  KEISRHRKAGHGSSGLRKQQAHESSRPLSIERPGAVHPWVSAQLRNSVQPSHLFIQDPTM
h 679  KEISRHRRITGHGSSGTRKPQPHENSRPLSLE----HPWAGPQLRTSVQPSHLFIQDPTM
c 665  KEISRHKKTNHGSSGVKKQLSHDMVRPLSIERPMAVHPWVSAQLRNVVQPSHPFIQDPTM m 826  PPNPAPNPLTQLEEARRLEEEKRANKLPSKQRYVQAVMQRGRTCVRPACAPVLSVVPA
h 734  PPHPAPNPLTQLEEARRLEEEKRASRAPSKQRYVQEVMRRGRACVRPACAPVLHVVPA
c 725  PPNPAPNPLTQLEEARRLEEEKRAGKLPLKQR--36aa insert in form 2-- m 886  VSDLELSETETKSQRKAGGGSAPPCDSIVVGYYFCGEPIPYRTLVRGRAVTLGQFKELLT
h 794  VSDMELSETETRSQRKVGGGSAQPCDSIVVAYYFCGEPIPYRTLVRGRAVTLGQFKELLT
c 759  -------LKPQKRPGSGASQPCENIVVAYYFCGEPIPYRTLVKGRVTLGQFKELLT m 946  KKGSYRYYFKKVSDEFDCGVVFEEVREDEPVLPVFEEKIIGKVEKVD 992
h 854  KKGSYRYYFKKVSDEFDCGVVFEEVREDEAVLPVFEEKIIGKVEKVD 900
c 809  KKGNYRYYFKKVSDEFDCGVVFEEVREDDTILPIFEEKIIGKVEKID 855
```

FIGURE 3C

```
hRGS2    LWSEAFDELLASKYGLAAFRAFLKSEFCEENIEFWLACEDFKKTKSP----QKLSSKARKIYTD
hRGS5    QWRDSLDKLLQNNYGLASFKSFLKSEFSEENLEFWLACEDYKKIKSP----AKMAEKAKQIYEE
hRGS3    KMGESLEKLLVHKYGLAVFQAFLRTEFSEENLEFWLACEDFKKVKSQ----SKMASKAKKIFAE
rRGS4    KWAESLENLISHECGLAAFKAFLKSEYSEENIDFWISCEEYKKIKSP----SKLSPKAKKIYNE
hRGS1    QWSQSLEKLLANQTGQNVFGSFLKSEFSEENIEFWLACEDYKKTES-----DLLPCKAEEIYKA
hGAIP    SWAQSFDKLMHSPAGRSVFRAFLKSEYSEENMLFWLACEELKAEANQ----HVVDEKARLIYED
hRGS7    RMGFGMDEALKDPVGREQFLKFLESEFSSENLRFWLAVEDLKKRPI-----KEVPSRVQEIWQE
hRGS10   KWAASLENLLEDPEGVKRFREFLKKEFSEENVLFWLACEDFKKMQKD----TQMQEKAKEIYMT
mAxin    RWAESLHSLLDDQDGISLFRITFLKQEGCADLLDFWFACSGFRKLEPCDSNEEKRLKLARAIYRK hRGS2    FIEKEA---PKEINIDFQTKTLIAGNIQEATSGCFTTAQKRVVSLMENNSYPRFLESEFYQDL
hRGS5    FIQTEA---PKEVNIDHFTKDITMKNLVEPISLSSFDMAQKRITHALMEKDSLPRFVRSEFYQEL
hRGS3    YIAIQA---CKEVNLDSYTREHTKDNLLAQKRIFGLMEKDSYPRFLRSDLYLDL
rRGS4    FISVQA---TKEVNLDSCTREETISRNMLEPTITCFDEAQKKIIFNLMEKDSYPRFLKSRFYLDL
hRGS1    FVHSDA---AKQINIDFRTRESUAKKIKAPTPTCFDEAQKVIYTLMEKDSYPRFLKSHIYLNL
hGAIP    YVSILS---PKEVSIDSRVREGINKKMQEPSAHTFDDAQLQIYTLMHRDSYPRFLSSPTYRAL
hRGS7    FLAPGA---PSAINLDSKSYDKITQNVKEPGRYTFEDAQEHIYKLMKSDSYPRFLKSDLFLKH
hRGS10   FLSSKA---SSQVNVEGQ-SRLNEKILEEPHPLMFQKLQDQIFNLMKYDSYSPRFLKSDLFLKH
mAxin    YILDSNGIVSRQTKPATKSFIKDCVMKQQIDPAMFDQAQTEIQSTMEENTYPSFLKSDIYLEY
```

FIGURE 3D

```
mDv1-1   28   VTLADFKNVLSNRPVHAYKFFFKSMDQDF--GVVKEEIFDDNAKLPCFNGRVV   78
mDv1-2   38   ITLGDFKSVLQR--PAGAKYFFKSMDQDF--GVVKEEISDDNARLPCFNGRVV   86
Dsh      35   VTLRDFKLVLNKQ-NNNYKYFFKSMDADF--GVVKEEIADDSTILPCFNGRVV   84
mAxin   935   VTLGQFKELLTK--KGSVRYYFKKVSDEFDCGVVFEEVREDEPVLPVFEEKII  985
```

FIGURE 8

/translation="LGSGSRLREALAAAAAGACWGRAGAWFQRGLVRVSSRFWRRSAA
CLAPPPGHGSPSRRRRDGGPPGPRPRRGPPAEPPLSAWASPGREPGPGPRLHSRRAL
ERLIPLGAVSTEVLGCSAHCSLMQSPKMNVQEQGFPLDLGASFTEDAPRPPVPGEEGE
LVSTDSRPVNHSFCSGKGTSIKSETSTATPRRSDLDLGYEPEGSASPTPPYLRWAESL
HSLLDDQDGISLFRTFLKQEGCADLLDFWFACSGFRKLEPCDSNEEKRLKLARAIYRK
YILDSNGIVSRQTKPATKSFIKDCVMKQQIDPAMFDQAQTEIQSTMEENTYPSFLKSD
IYLEYTRTGSESPKVCSDQSSGSGTGKGMSGYLPTLNEDEEWKCDQDADEDDGRDPLP
PSRLTQKLLLETAAPRAPSSRRYNEGRELRYGSWREPVNPYYVNSGYALAPATSANDS
EQQSLSSDADTLSLTDSSVDGIPPYRIRKQHRREMQESIQVNGRVPLPHIPRTYRMPK
EIRVEPQKFAEELIHRLEAVQRTREAEEKLEERLKRVRMEEEGEDGEMPSGPMASHKL
PSVPAWHHFPPRYVDMGCSGLRDAHEENPESILDEHVQRVMRTPGCQSPGPGHRSPDS
GHVAKTAVLGGTASGHGKHVPKLGLKLDTAGLHHHRHVHHHVHHNSARPKEQMEAEVA
RRVQSSFSWGPETHGHAKPRSYSENAGTTLSAGDLPFGGKTSAPSKRNTKKAESGKNA
NAEVPSTTEDAEKNQKIMQWIIEGEKEISRHRKAGHGSSGLRKQQAHESSRPLSIERP
GAVHPWVSAQLRNSVQPSHLFIQDPTMPPNPAPNPLTQLEEARRLEEEKRANKLPS
KQRYVQAVMQRGRTCVRPACAPVLSVVPAVSDLELSETETKSQRKAGGGSAPPCDSIV
VGYYFCGEPIPYRTLVRGRAVTLGQFKELLTKKGSYRYFKKVSDEFDCGVVFEEVRE
DEPVLPVFEEKIIGKVEKVD"

FIG. 9A

```
   1 ctctggctc aggctcccgg ctcagggaag cgcttgcggc cgccgccgca ggagcctgct
  61 ggggtcgggc tggagcctgg ttccagagag ggctggtgag agtgagcagc cggttttggc
 121 ggcgctctgc ggcctgcctt gcgccgcctc cgggccacgg gtcgccgagc cgccgccgcc
 181 gccgcgatgg gggccccca gggccgcgcc cccgccgtgg cccgccccgct gagccgccgc
 241 tgagcgcatg gcctcgccgg gccggggagc caggcccccg gccgccgcctc cacagccgcc
 301 gcgcgctgga gagattgatt cccttgggag ctgtaagtac tgaggtatta gggtgcagcg
 361 ctcattgttc actgatgcag agtcccaaaa tgaatgtcca ggagcaggt ttcccttgg
 421 acctcggagc aagtttcacc gaagatgccc cccggcccc agtgcctgga gaagagggag
 481 aactgtatc tactgattcg aggcctgtca accacagttt ctgttctggg aaagtacca
 541 gcattaaaag tgagacctca acagccaccc caagacgttc agatctggat ctgggatatg
 601 agcccgaggg cagtgcctcc cccacccccac catatttgag gtgggctgag tcactgcatt
 661 ccttactgga tgaccaagat gggatcagcc tgttccaggac tttcctgaag caggagggct
 721 gtgctgacct gctggacttc tggttttgcct gcagtggctt caggaagctt gagcctgtg
 781 actcaaatga ggaaaagagg ctgaagctgg caagagccat ctaccgaaag tacatcctgg
 841 atagcaatgg cattgtgtcc agacaaacca agccagccac taagagcttc ataaaggact
 901 gtgtcatgaa gcagcagata gatcctgcca tgtttgacca ggcacagaca gaaatccagt
 961 ccaccatgga ggagaatacc taccctttcct ttcttaagtc tgacatttat ttggagtaca
1021 caaggacagg ctcagagagt ccgaaggtct gcagtgacca gagctcaggg tctggaacag
1081 ggaaggcat gtctggatac ctgccacctt tgaatgagga tgaagaatgg aaatgtgacc
1141 aagatgcaga tgaggatgat ggccgagacc ctctcccccc cagcaggctc accagaagc
1201 tgctattgga gactgctgcc ccgagggccc cctcaagtag acgtacaaac gaaggcagag
1261 agctcaggta tggatcttgg agggagcccg tcaaccccta ctacgtcaac tctgctatg
1321 ccctggcccc agccaccagt gccaatgaca gtgagcagca gagcctgtcc cccatacagg
1381 acacgctatc ccttacggac agtagtgtgg atgaatccc aagtcaatgg gcggtacct ctacctcaca
1441 agcacggaag ggagatgcag gagagtatcc ccaaaggaga tccgggtaga gccacagaa tttgctgaag
1501 ttcctcgcac ttaccgaatg ccaaagtcca ggctgtccag gcactcgaga gcactgaga aagttggagg
1561 agcttattca ccgtctagag gctgtccagc gcactcgaga ggctgaagaa aagttggagg
1621 aacgctgaa gcgtgtacgc atggagaag cctctgtcc aagggagga tggtgaaatg ccttctggcc
1681 ccatgcaag tcacaagctg ccttctgtcc cagcttgca ccatacagg cccgctatg
1741 tggatatggg ctgctctga ctgcggatg cccatgagga gaatcctgag agcatcctgg
1801 atgagcacgt gcaaaggtc atgaggacac ctgctgcca gtcacctggc ccaggccacc
1861 gctctcctga cagtgggcat gtggctaaga ctgcagtgct agggggtaca aggggtaca gcctccgggc
```

FIG. 9B

```
1921 atgggaagca tgttcctaag ttagggttga agctgatac agctgcctg caccatcata
1981 gacatgtcca ccaccatgtt caccataatt cagctagacc taaggagcaa atggaggctg
2041 aagttgcccg cagggtccag agcagcttct cgtgggccc agaaacacat ggtcatgcca
2101 agcccggag ctattccgag aacgcaggca ccaccctcag tgctgggat ttgcccttg
2161 gtggtaaaac tagtgcacct tccaaaagaa acaccaagaa ggctgaatct gggaagaatg
2221 ccaatgctga ggtaccagt accacagagg acgctgagaa gaaccagaag atcatgcagt
2281 ggatcattga gggagagaag gagatcagta gacaccggaa ggcaggccat gggtcttctg
2341 ggttgaggaa gcagcaggcc catgaaagct ccagcccctt gtccatcgag cgtcctgggg
2401 ccgtgcaccc ctgggtcagc gctcagcttc ggaattctgt ccagccttct catcttttca
2461 tccaagatcc cacaatgcca cccaatccag ccctaatcc cctgacccag ctgaagagg
2521 cccgcaggcg tttggaagaa gagcaaaaga gagcaaacaa actgccctcc aagcagaggt
2581 atgtgcaggc agtcatgcag cggggacgca cctgtgtcag gccagcttgt gcaccggtgc
2641 tgagtgtggt accagccgtg tcggacttgg aactctccga gacagagaca aaatcacaaa
2701 gaaaggcagg tggcgggagt gcaccaccat gtgacagcat tgttgtgggc tactatttct
2761 gtggggaacc catcccctac cggaccctgg tgagggggcg tgctgtcacc ctggccagt
2821 tcaaggagct gctaaccaag aaggggagct acagatacta ctttaagaaa gtgagtgatg
2881 agtttgactg tggtgtggta tttgaggaag tacgggagga tgagcccgtc ttgcctgtct
2941 ttgaagaaaa gatcatcggc aagtgtggaaa agtggactg agcactgggc agcacacccg
3001 gagcacacca tcactactgt gcattgtcat cagtcaggtg gacagccttg tcctcaggag
3061 cctgtgtgtgg aagattgtgt aagattgtgt catgagctct tctatcgggg tgaggctggg
3121 gaccttaggt gtctgccagc ctctgtccct ctggctttgg gaaagtgggg gtggggtc
3181 gtcctactga gtggttcctt gggtttctct gttttcctgt ccttcaacat agttccactt
3241 accaccacat taccccctga agcaatacca ggagccatct catgaccctc agcagctctt
3301 gcttctgaat ccagtctgac ctaggatac tttgcccctgg gcttgtatcc cactgtcctc
3361 ttctctctct ctggaccta tccactgcac ctggtttggc tcaggtccag gagcaggga
3421 tcctgtgggg gctctatat attgtacatg tcactgagtg ccttcaacat agctgtctct
3481 tgcctgccac tgtgtgaatc tggcagctga gtatctcagg gtatctcagg ccccttgcc tgtctccagc
3541 caccagcttg gttcagcagg aggggggcg gtgtgtgg cccttccaa gtgtccgtgt
3601 aaatatgtac atttctcagg ccaggccag caggggata cctgagccc atttttcatg
3661 caatgacttg tacaattatc tttcaaagg tacttggata ataatgaaat aaaaacgttt
3721 ttgaaccttc caaaaaaaaa aaaaaaaaaa aaaaaaaaaaa a
```

FIGURE 10A

```
   1 ggcccgggg tcccgccacc accgcgcgcg ggacagattg attcactttg gagctgtaag
  61 tactgatgta ttagggtgca gcgctcattg ttcattgacg cagagtccca aaatgaatat
 121 ccaagagcag ggtttcccct tggacctcgg agcaagtttc accgaagatg ctcccgacc
 181 cccagtgcct ggtgaggagg gagaactggt gtccacagac ccgaggcccg ccagctacag
 241 tttctgctcc gggaaaggtg ttggcattaa aggtgagact tcgacggcca ctccgaggcg
 301 ctcggatctg gacctggggt atgagcctga gggcagtgcc tcccccaccc caccatactt
 361 gaagtgggct gagtcactgc attccctgct ggatgaccaa gatggataa gctgttcag
 421 gactttcctg aagcaggagg gctgtgccga cttgctggac ttctggtttg cctgcactgg
 481 cttcaggaag ctggagccct gtgactcgaa cgaggagaag aggctgaagc tggcgagagc
 541 catctaccga aagtacattc ttgataacaa tggcatcgtg tcccggcaga ccaagccagc
 601 caccaagagc ttcatataagg gctgcatcat gaagcagctg atcgatcctg ccatgttttga
 661 ccaggcccag accgaaatcc aggccactat ggaggaaaac acctatccct ccttccttaa
 721 gtctgatatt tatttggaat atacgaggac aggctcggag agcccccaaag tctgtagtga
 781 ccagagctct gggtcaggga cagggaaggg catatcctga tacctgccga ccttaaatga
 841 agatgaggaa tggaagtgtg accaggacat ggacgaggac gatgcagag acgctgctcc
 901 cccccggaaga ctcccctcaga agctgctcct ggagacagct gccccgaggg tctcctccag
 961 tagacgtac agcgaaggca gagagttcag gtatggatcc tggcgggagc cagtcaaccc
1021 ctattatgtc aatgcccggct atgccccttggc cccagccacc agtgccaaacg acagcgagca
1081 gcagagcctg tccagcgatg cagacaccct gtccctcacg gacacagcg tggatgggat
1141 cccccatac aggatccgta agcagcaccg cagggagatg caggagagcg cgcaggtcaa
1201 tgggcgggtg cccctacctc acattcccg cacgtaccgg gtgccgaagg cgcagtccgct
1261 ggagcctcag aagttcgcgg aggagctcat ccacggcctg gaggctgtgc agcgcacgcg
1321 ggaggccgag gagaagctgg aggagggct gaagcgcgtg cgcatggagg agaaggtga
1381 ggatggcgat ccatcgtcag ggccccagg gcccccagg gccgtgtcac aagctgcctc ccgccccgc
1441 ttggcaccac ttccccgccc gcttgtgttg gacatgggct tgtgccgggc tccggatgc
1501 acacgaggag aaccctgaga gcatcctgga cgagcacgta cagcgtgtgc tgaggacaac
1561 tgccgccag tcgcctgggc ctggccatcg ctccccggac agtgggcacg tggccaagat
```

FIGURE 10B

```
1621 gccagtggca ctggggggtg ccgcctcggg gcacggaag cacgtaccca agtcagggc
1681 gaagctggac gcggccggcc tgcaccacca ccgacacgtc caccaccacg tccaccacag
1741 cacagcccgg cccaaggagc agtggaggc cgaggccacc cgcaggccc agagcagctt
1801 cgcctggggc ctggaaccac acagccatgg ggcaaggtcc cgaggctact cagagagtgt
1861 tggcgctgcc cccaacgcca gtgatggcct cgcccacagt gggaaggtgg gcgttgcgtg
1921 caaagaaat gccaagaagg ctgagtcggg gaagagcgc agcaccgagg tgccaggtgc
1981 ctcggaggat gcggagaaga accajaaaat catgcagtgg atcattgagg gggaaaagga
2041 gatcagcagg caccgcagga ccggccacgg gtcttcgggg acgaggaagc cacagcccca
2101 tgagaactcc agaccyttgt cccttgagca cccctggcc ggccctcagc tccggactc
2161 cgtgcagccc tcccactct tcatccaaga ccaccatg ccaccccacc cagctcccaa
2221 ccccctaacc cagctggagg agcgcgccg acgtctggag gaggaagaaa agagcccag
2281 ccgagcaccc tccaagcaga ggtatgtgca ggaggttatg cggcggggac gcgcctgcgt
2341 caggccagcg tgcgcgcgg tgctgcacgt gtaccacgt gtgtcggaca tggagctctc
2401 cgagacagag acaagatcgc agaggaagt gggcggcggg agtgccagc cgtgtgacag
2461 catcgttgtg gcgtactact tctgcgggga accatcccc taccgcaccc tggtgagggg
2521 cgcgctgtc accctgggcc agttcaagga gctgctgacc aaaagggca gctacagata
2581 ctacttcaag aaagtgagcg acgagtttga ctgtggggtg gtgttgagg aggttcgaga
2641 ggacgaggcc gtcctgcccg tcttgtctct ggcaaagtgg agaaggtgga
2701 ctgataggct ggtgggctgg ccgctgtgcc aggcgaggcc cttggcgggc acgggtgtca
2761 cggccaggca gatgacctcg tactcaggag cccgatgggg aacagtgttg ggtgtaccac
2821 ccatccctgt ggtctaccg tgtctagagg caggtaggg gtccctccaa gtggtccaca
2881 agcttctgtc ctgcccccaa ggaggcagcc tggaccactc ctcatagcaa tacttggagg
2941 gccagccca agtgaggcag ccgaggtccc tgctgccagc ttcagtgac ccccccat
3001 cccccggcac ctcccttggg cacgtgtgct gggatctact tccctctgg gatttgcca
3061 cgtacccagg tctggctggg gccaggcc ggatgcagag gcctgcaggg cctctgtcaa
3121 ttgtacgcgc caccagtgc cttcaacaca gcttgtctct gcctgccac tgtgtgaatc
3181 ggcgacgag cactgcacct gcctccagc gccggctgtg cagtcctggg tcctccttc
3241 tgagggccg tgtaaatatg tacattctc aggctagggc cagcagggc tgccgagtc
3301 tgtttttcat gcgatgacac ttgtacaatt atctttcaa agtacttgg ataataatga
3361 aataaactg tttttgaacc tgaataaaaa aaaaaaaaaa aaaaaaaaaa a
```

FIGURE 11

/translation="GPGSRHHRARDRLIHFGAVSTDVLGCSAHCSLTQSPKMNIQEQG
FPLDLGASFTEDAPRPPVPGEEGELVSTDPRPASYSFCSGKGVGIKGETSTATPRRSD
LDLGYEPEGSASPTPPYLKWAESLHSLLDDQDGISLFRTFLKQEGCADLLDFWFACTG
FRKLEPCDSNEEKRLKLARAIYRKYILDNNGIVSRQTKPATKSFIKGCIMKQLIDPAM
FDQAQTEIQATMEENTYPSFLKSDIYLEYTRTGSESPKVCSDQSSGSGTGKGISGYLP
TLNEDEEWKCDQDMEDDGRDAAPPGRLPQKLLLETAAPRVSSSRRYSEGREFRYGSW
REPVNPYYVNAGYALAPATSANDSEQQSLSSDADTLSLTDSSVDGIPPYRIRKQHRRE
MQESAQVNGRVPLPHIPRTYRVPKEVRVEPQKFAEELIHRLEAVQRTREAEEKLEERL
KRVRMEEEGEDGDPSSGPPGPCHKLPPAPAWHHFPPRLCWTWACAGLRDAHEENFESI
LDEHVQRVLRTTGRQSPGPGHRSPDSGHVAKMPVALGGAASGHGKHVFKSGAKLDAAG
LHHRRHVHHHVHHSTARPKEQVEAEATRRAQSFAWGLEPHSHGARSRGYSESVGAAP
NASDGLAHSGKVGVACKRNAKKAESGKSASTEVPGASEDAEKNQKIMQWIIEGEKEIS
RHRRTGHGSSGTRKPQPHENSRPLSLEHPWAGPQLRTSVQPSHLFIQDPTMPPHPAPN
PLTQLEEARRLEEEKRASRAPSKQRYVQEVMRRGPACVRPACAPVLHVVPAVSDME
LSETETRSQRKVGGGSAQPCDSIVVAYFFCGEPIPYRTLVRGRAVTLGQFKELLTKKG
SYRYYFKKVSDEFDCGVVFEEVREDEAVLPVEEEKTIGKVEKVD"

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 992 amino acids
      (B) TYPE: amino acid
      (C) STRANDEDNESS: single
      (D) TOPOLOGY: linear (ii) MOLECULE TYPE: Protein (xi) SEQUENCE DESCRIPTION: SEQ ID NO:1:

```
Leu Gly Ser Gly Ser Arg Leu Arg Glu Ala Leu Ala Ala Ala Ala Ala
  1               5                  10                  15

Gly Ala Cys Trp Gly Arg Ala Gly Ala Trp Phe Gln Arg Gly Leu Val
                 20                  25                  30

Arg Val Ser Ser Arg Phe Trp Arg Arg Ser Ala Ala Cys Leu Ala Pro
             35                  40                  45

Pro Pro Gly His Gly Ser Pro Ser Arg Arg Arg Arg Asp Gly Gly
     50                  55                  60

Pro Pro Gly Pro Arg Pro Arg Arg Gly Pro Pro Ala Glu Pro Pro Leu
 65                  70                  75                  80

Ser Ala Trp Ala Ser Pro Gly Arg Glu Pro Gly Pro Gly Pro Arg Leu
                 85                  90                  95

His Ser Arg Arg Ala Leu Glu Arg Leu Ile Pro Leu Gly Ala Val Ser
                100                 105                 110

Thr Glu Val Leu Gly Cys Ser Ala His Cys Ser Leu Met Gln Ser Pro
            115                 120                 125

Lys Met Asn Val Gln Glu Gln Gly Phe Pro Leu Asp Leu Gly Ala Ser
            130                 135                 140

Phe Thr Glu Asp Ala Pro Arg Pro Pro Val Pro Gly Glu Glu Gly Glu
145                 150                 155                 160

Leu Val Ser Thr Asp Ser Arg Pro Val Asn His Ser Phe Cys Ser Gly
                165                 170                 175

Lys Gly Thr Ser Ile Lys Ser Glu Thr Ser Thr Ala Thr Pro Arg Arg
                180                 185                 190

Ser Asp Leu Asp Leu Gly Tyr Glu Pro Glu Gly Ser Ala Ser Pro Thr
            195                 200                 205

Pro Pro Tyr Leu Arg Trp Ala Glu Ser Leu His Ser Leu Leu Asp Asp
    210                 215                 220

Gln Asp Gly Ile Ser Leu Phe Arg Thr Phe Leu Lys Gln Glu Gly Cys
225                 230                 235                 240

Ala Asp Leu Leu Asp Phe Trp Phe Ala Cys Ser Gly Phe Arg Lys Leu
                245                 250                 255

Glu Pro Cys Asp Ser Asn Glu Glu Lys Arg Leu Lys Leu Ala Arg Ala
            260                 265                 270

Ile Tyr Arg Lys Tyr Ile Leu Asp Ser Asn Gly Ile Val Ser Arg Gln
        275                 280                 285

Thr Lys Pro Ala Thr Lys Ser Phe Ile Lys Asp Cys Val Met Lys Gln
            290                 295                 300

Gln Ile Asp Pro Ala Met Phe Asp Gln Ala Gln Thr Glu Ile Gln Ser
305                 310                 315                 320
```

-continued

```
Thr Met Glu Glu Asn Thr Tyr Pro Ser Phe Leu Lys Ser Asp Ile Tyr
            325                 330                 335
Leu Glu Tyr Thr Arg Thr Gly Ser Glu Ser Pro Lys Val Cys Ser Asp
            340                 345                 350
Gln Ser Ser Gly Ser Gly Thr Gly Lys Gly Met Ser Gly Tyr Leu Pro
            355                 360                 365
Thr Leu Asn Glu Asp Glu Glu Trp Lys Cys Asp Gln Asp Ala Asp Glu
            370                 375                 380
Asp Asp Gly Arg Asp Pro Leu Pro Pro Ser Arg Leu Thr Gln Lys Leu
385                 390                 395                 400
Leu Leu Glu Thr Ala Ala Pro Arg Ala Pro Ser Ser Arg Arg Tyr Asn
            405                 410                 415
Glu Gly Arg Glu Leu Arg Tyr Gly Ser Trp Arg Glu Pro Val Asn Pro
            420                 425                 430
Tyr Tyr Val Asn Ser Gly Tyr Ala Leu Ala Pro Ala Thr Ser Ala Asn
            435                 440                 445
Asp Ser Glu Gln Gln Ser Leu Ser Ser Asp Ala Asp Thr Leu Ser Leu
            450                 455                 460
Thr Asp Ser Ser Val Asp Gly Ile Pro Pro Tyr Arg Ile Arg Lys Gln
465                 470                 475                 480
His Arg Arg Glu Met Gln Glu Ser Ile Gln Val Asn Gly Arg Val Pro
            485                 490                 495
Leu Pro His Ile Pro Arg Thr Tyr Arg Met Pro Lys Glu Ile Arg Val
            500                 505                 510
Glu Pro Gln Lys Phe Ala Glu Glu Leu Ile His Arg Leu Glu Ala Val
            515                 520                 525
Gln Arg Thr Arg Glu Ala Glu Glu Lys Leu Glu Glu Arg Leu Lys Arg
            530                 535                 540
Val Arg Met Glu Glu Glu Gly Glu Asp Gly Glu Met Pro Ser Gly Pro
545                 550                 555                 560
Met Ala Ser His Lys Leu Pro Ser Val Pro Ala Trp His His Phe Pro
            565                 570                 575
Pro Arg Tyr Val Asp Met Gly Cys Ser Gly Leu Arg Asp Ala His Glu
            580                 585                 590
Glu Asn Pro Glu Ser Ile Leu Asp Glu His Val Gln Arg Val Met Arg
            595                 600                 605
Thr Pro Gly Cys Gln Ser Pro Gly Pro Gly His Arg Ser Pro Asp Ser
            610                 615                 620
Gly His Val Ala Lys Thr Ala Val Leu Gly Gly Thr Ala Ser Gly His
625                 630                 635                 640
Gly Lys His Val Pro Lys Leu Gly Leu Lys Leu Asp Thr Ala Gly Leu
            645                 650                 655
His His His Arg His Val His His His Val His His Asn Ser Ala Arg
            660                 665                 670
Pro Lys Glu Gln Met Glu Ala Glu Val Ala Arg Arg Val Gln Ser Ser
            675                 680                 685
Phe Ser Trp Gly Pro Glu Thr His Gly His Ala Lys Pro Arg Ser Tyr
            690                 695                 700
Ser Glu Asn Ala Gly Thr Thr Leu Ser Ala Gly Asp Leu Pro Phe Gly
705                 710                 715                 720
Gly Lys Thr Ser Ala Pro Ser Lys Arg Asn Thr Lys Lys Ala Glu Ser
            725                 730                 735
```

```
Gly Lys Asn Ala Asn Ala Glu Val Pro Ser Thr Thr Glu Asp Ala Glu
              740                 745                 750
Lys Asn Gln Lys Ile Met Gln Trp Ile Ile Glu Gly Glu Lys Glu Ile
          755                 760                 765
Ser Arg His Arg Lys Ala Gly His Gly Ser Ser Gly Leu Arg Lys Gln
      770                 775                 780
Gln Ala His Glu Ser Ser Arg Pro Leu Ser Ile Glu Arg Pro Gly Ala
785                 790                 795                 800
Val His Pro Trp Val Ser Ala Gln Leu Arg Asn Ser Val Gln Pro Ser
                  805                 810                 815
His Leu Phe Ile Gln Asp Pro Thr Met Pro Pro Asn Pro Ala Pro Asn
              820                 825                 830
Pro Leu Thr Gln Leu Glu Glu Ala Arg Arg Leu Glu Glu Glu
          835                 840                 845
Lys Arg Ala Asn Lys Leu Pro Ser Lys Gln Arg Tyr Val Gln Ala Val
      850                 855                 860
Met Gln Arg Gly Arg Thr Cys Val Arg Pro Ala Cys Ala Pro Val Leu
865                 870                 875                 880
Ser Val Val Pro Ala Val Ser Asp Leu Glu Leu Ser Glu Thr Glu Thr
                  885                 890                 895
Lys Ser Gln Arg Lys Ala Gly Gly Ser Ala Pro Pro Cys Asp Ser
              900                 905                 910
Ile Val Val Gly Tyr Tyr Phe Cys Gly Glu Pro Ile Pro Tyr Arg Thr
          915                 920                 925
Leu Val Arg Gly Arg Ala Val Thr Leu Gly Gln Phe Lys Glu Leu Leu
      930                 935                 940
Thr Lys Lys Gly Ser Tyr Arg Tyr Tyr Phe Lys Lys Val Ser Asp Glu
945                 950                 955                 960
Phe Asp Cys Gly Val Val Phe Glu Glu Val Arg Glu Asp Glu Pro Val
                  965                 970                 975
Leu Pro Val Phe Glu Glu Lys Ile Ile Gly Lys Val Glu Lys Val Asp
              980                 985                 990

(2) INFORMATION FOR SEQ ID NO:2:

(i) SEQUENCE CHARACTERISTICS:
        (A) LENGTH: 3761 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

CTCTGGGCTC AGGCTCCCGG CTCAGGGAAG CGCTTGCGGC CGCCGCCGCA GGAGCCTGCT      60

GGGGTCGGGC TGGAGCCTGG TTCCAGAGAG GGCTGGTGAG AGTGAGCAGC CGGTTTTGGC     120

GGCGCTCTGC GGCCTGCCTT CGCCGCCCTC CGGGCCACGG GTCGCCGAGC CGCCGCCGCC     180

GCCGCGATGG GGCCCCCCA GGGCCGCGCC CCGCCGTGG CCCGCCCGCT GAGCCGCCGC       240

TGAGCGCATG GGCCTCGCCG GGCCGGGAGC CAGGCCCCGG GCCGCGCCTC CACAGCCGCC     300

GCGCGCTGGA GAGATTGATT CCCTTGGGAG CTGTAAGTAC TGAGGTATTA GGGTGCAGCG     360

CTCATTGTTC ACTGATGCAG AGTCCCAAAA TGAATGTCCA GGAGCAGGGT TTCCCCTTGG     420

ACCTCGGAGC AAGTTTCACC GAAGATGCCC CCCGGCCCCC AGTGCCTGGA GAAGAGGGAG     480

AACTGGTATC TACTGATTCG AGGCCTGTCA ACCACAGTTT CTGTTCTGGG AAAGGTACCA     540
```

-continued

| | | | | |
|---|---|---|---|---|
| GCATTAAAAG | TGAGACCTCA | ACAGCCACCC | CAAGACGTTC | AGATCTGGAT CTGGGATATG | 600 |
| AGCCCGAGGG | CAGTGCCTCC | CCCACCCCAC | CATATTTGAG | GTGGGCTGAG TCACTGCATT | 660 |
| CCTTACTGGA | TGACCAAGAT | GGGATCAGCC | TGTTCAGGAC | TTTCCTGAAG CAGGAGGGCT | 720 |
| GTGCTGACCT | GCTGGACTTC | TGGTTTGCCT | GCAGTGGCTT | CAGGAAGCTT GAGCCCTGTG | 780 |
| ACTCAAATGA | GGAAAAGAGG | CTGAAGCTGG | CAAGAGCCAT | CTACCGAAAG TACATCCTGG | 840 |
| ATAGCAATGG | CATTGTGTCC | AGACAAACCA | AGCCAGCCAC | TAAGAGCTTC ATAAAGGACT | 900 |
| GTGTCATGAA | GCAGCAGATA | GATCCTGCCA | TGTTTGACCA | GGCACAGACA GAAATCCAGT | 960 |
| CCACCATGGA | GGAGAATACC | TACCCTTCCT | TTCTTAAGTC | TGACATTTAT TTGGAGTACA | 1020 |
| CAAGGACAGG | CTCAGAGAGT | CCGAAGGTCT | GCAGTGACCA | GAGCTCAGGG TCTGGAACAG | 1080 |
| GGAAGGGCAT | GTCTGGATAC | CTGCCCACTT | TGAATGAGGA | TGAAGAATGG AAATGTGACC | 1140 |
| AAGATGCAGA | TGAGGATGAT | GGCCGAGACC | CTCTCCCCCC | CAGCAGGCTC ACCCAGAAGC | 1200 |
| TGCTATTGGA | GACTGCTGCC | CCGAGGGCCC | CCTCAAGTAG | ACGGTACAAC GAAGGCAGAG | 1260 |
| AGCTCAGGTA | TGGATCTTGG | AGGGAGCCCG | TCAACCCCTA | CTACGTCAAC TCTGGCTATG | 1320 |
| CCCTGGCCCC | AGCCACCAGT | GCCAATGACA | GTGAGCAGCA | GAGCCTGTCC AGTGATGCTG | 1380 |
| ACACGCTATC | CCTTACGGAC | AGTAGTGTGG | ATGGAATCCC | CCCATACAGG ATCCGTAAGC | 1440 |
| AGCACCGAAG | GGAGATGCAG | GAGAGTATCC | AAGTCAATGG | GCGGGTACCT CTACCTCACA | 1500 |
| TTCCTCGCAC | TTACCGAATG | CCAAAGGAGA | TCCGGGTAGA | GCCACAGAAA TTTGCTGAAG | 1560 |
| AGCTTATTCA | CCGTCTAGAG | GCTGTCCAGC | GCACTCGAGA | GGCTGAAGAA AAGTTGGAGG | 1620 |
| AACGGCTGAA | GCGTGTACGC | ATGGAGGAAG | AAGGGGAGGA | TGGTGAAATG CCTTCTGGCC | 1680 |
| CCATGGCAAG | TCACAAGCTG | CCTTCTGTCC | CAGCTTGGCA | CCATTTCCCA CCCCGCTATG | 1740 |
| TGGATATGGG | CTGCTCTGGA | CTGCGGGATG | CCCATGAGGA | GAATCCTGAG AGCATCCTGG | 1800 |
| ATGAGCACGT | GCAAAGGGTC | ATGAGGACAC | CTGGCTGCCA | GTCACCTGGC CCAGGCCACC | 1860 |
| GCTCTCCTGA | CAGTGGGCAT | GTGGCTAAGA | CTGCAGTGCT | AGGGGGTACA GCCTCCGGGC | 1920 |
| ATGGGAAGCA | TGTTCCTAAG | TTAGGGTTGA | AGCTGGATAC | AGCTGGCCTG CACCATCATA | 1980 |
| GACATGTCCA | CCACCATGTT | CACCATAATT | CAGCTAGACC | TAAGGAGCAA ATGGAGGCTG | 2040 |
| AAGTTGCCCG | CAGGGTCCAG | AGCAGCTTCT | CGTGGGCCC | AGAAACACAT GGTCATGCCA | 2100 |
| AGCCCCGGAG | CTATTCCGAG | AACGCAGGCA | CCACCCTCAG | TGCTGGGGAT TTGCCCTTTG | 2160 |
| GTGGTAAAAC | TAGTGCACCT | TCCAAAAGAA | ACACCAAGAA | GGCTGAATCT GGGAAGAATG | 2220 |
| CCAATGCTGA | GGTACCCAGT | ACCACAGAGG | ACGCTGAGAA | GAACCAGAAG ATCATGCAGT | 2280 |
| GGATCATTGA | GGGAGAGAAG | GAGATCAGTA | GACACCGGAA | GCAGGCCAT GGGTCTTCTG | 2340 |
| GGTTGAGGAA | GCAGCAGGCC | CATGAAAGCT | CCAGGCCCTT | GTCCATCGAG CGTCCTGGGG | 2400 |
| CCGTGCACCC | CTGGGTCAGC | GCTCAGCTTC | GGAATTCTGT | CCAGCCTTCT CATCTTTTCA | 2460 |
| TCCAAGATCC | CACAATGCCA | CCCAATCCAG | CCCCTAATCC | CCTGACCCAG CTGGAAGAGG | 2520 |
| CCCGCAGGCG | TTTGGAAGAA | GAAGAAAAGA | GAGCAAACAA | ACTGCCCTCC AAGCAGAGGT | 2580 |
| ATGTGCAGGC | AGTCATGCAG | CGGGGACGCA | CCTGTGTCAG | GCCAGCTTGT GCACCGGTGC | 2640 |
| TGAGTGTGGT | ACCAGCCGTG | TCGGACTTGG | AACTCTCCGA | GACAGAGACA AAATCACAAA | 2700 |
| GAAAGGCAGG | TGGCGGGAGT | GCACCACCAT | GTGACAGCAT | TGTTGTGGGC TACTATTTCT | 2760 |
| GTGGGGAACC | CATCCCCTAC | CGGACCCTGG | TGAGGGCCG | TGCTGTCACC CTGGGCCAGT | 2820 |
| TCAAGGAGCT | GCTAACCAAG | AAGGGGAGCT | ACAGATACTA | CTTTAAGAAA GTGAGTGATG | 2880 |
| AGTTTGACTG | TGGTGTGGTA | TTTGAGGAAG | TACGGGAGGA | TGAGCCCGTC TTGCCTGTCT | 2940 |

-continued

```
TTGAAGAAAA GATCATCGGC AAGGTGGAAA AGGTGGACTG AGCACTGGGC AGCACACCCG   3000

GAGCACACCA TCACTACTGT GCATTGTCAT CAGTCAGGTG GACAGCCTTG TCCTCAGGAG   3060

CCTGGTGTGG GGAACAACAC AAGATTGTGT CATGAGCTCT TCTATCGGGG TGAGGCTGGG   3120

GACCTTAGGT GTCTGCCAGC CTCTGTCCCT CTGGCTTTGG GAAAGTGGGG GTGGGGGGTC   3180

GTCCTACTGA GTGGTTCCTT GGGTTTCTCT GTTTTCCTGT TCAAGAGGAA AGTTCCACTT   3240

ACCACCACAT TACCCCCTGA AGCAATACCA GGAGCCATCT CATGACCCTC AGCAGCTCTT   3300

GCTTCTGAAT CCAGTCTGAC CTAGGGATAC TTTGCCCTGG GCTTGTATCC CACTGTCCTC   3360

TTCTCTCTCT CTGGGACCTA TCCACTGCAC CTGGTTGGGC TCAGGTCCAG GAGCAGGGGA   3420

TCCTGTGGGG GCCTCTATAT ATTGTACATG TCACTGAGTG CCTTCAACAT AGCTGTCTCT   3480

TGCCTGCCAC TGTGTGAATC TGGCAGCTGA GTATCTCAGG CCCCTTTGCC TGTCTCCAGC   3540

CACCAGCTTG GTTCAGCAGG AGGGGGGGCG GTGTGTCTGG TCCCTTCCAA GTGTCCGTGT   3600

AAATATGTAC ATTTCTCAGG CCAGGGCCAG CAGGGGGATA CCCTGAGCCC ATTTTTCATG   3660

CAATGACTTG TACAATTATC TTTTCAAAGG TACTTGGATA ATAATGAAAT AAAAACGTTT   3720

TTGAACCTTC CAAAAAAAAA AAAAAAAAA AAAAAAAAA A                        3761
```

(2) INFORMATION FOR SEQ ID NO:3:

(i) SEQUENCE CHARACTERISTICS:
        (A) LENGTH: 3411 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGGCCCGGGG TCCCGCCACC ACCGCGCGCG GGACAGATTG ATTCACTTTG GAGCTGTAAG     60

TACTGATGTA TTAGGGTGCA GCGCTCATTG TTCATTGACG CAGAGTCCCA AAATGAATAT    120

CCAAGAGCAG GGTTTCCCCT TGGACCTCGG AGCAAGTTTC ACCGAAGATG CTCCCCGACC    180

CCCAGTGCCT GGTGAGGAGG GAGAACTGGT GTCCACAGAC CCGAGGCCCG CCAGCTACAG    240

TTTCTGCTCC GGGAAAGGTG TTGGCATTAA AGGTGAGACT TCGACGGCCA CTCCGAGGCG    300

CTCGGATCTG GACCTGGGGT ATGAGCCTGA GGGCAGTGCC TCCCCCACCC CACCATACTT    360

GAAGTGGGCT GAGTCACTGC ATTCCCTGCT GGATGACCAA GATGGGATAA GCCTGTTCAG    420

GACTTTCCTG AAGCAGGAGG CTGTGCCGA  CTTGCTGGAC TTCTGGTTTG CCTGCACTGG    480

CTTCAGGAAG CTGGAGCCCT GTGACTCGAA CGAGGAGAAG AGGCTGAAGC TGGCGAGAGC    540

CATCTACCGA AAGTACATTC TTGATAACAA TGGCATCGTG TCCCGGCAGA CCAAGCCAGC    600

CACCAAGAGC TTCATAAAGG GCTGCATCAT GAAGCAGCTG ATCGATCCTG CCATGTTTGA    660

CCAGGCCCAG ACCGAAATCC AGGCCACTAT GGAGGAAAAC ACCTATCCCT CCTTCCTTAA    720

GTCTGATATT TATTTGGAAT ATACGAGGAC AGGCTCGGAG AGCCCAAAG  TCTGTAGTGA    780

CCAGAGCTCT GGGTCAGGGA CAGGGAAGGG CATATCTGGA TACCTGCCGA CCTTAAATGA    840

AGATGAGGAA TGGAAGTGTG ACCAGGACAT GGACGAGGAC GATGGCAGAG ACGCTGCTCC    900

CCCCGGAAGA CTCCCTCAGA AGCTGCTCCT GGAGACAGCT GCCCCGAGGG TCTCCTCCAG    960

TAGACGGTAC AGCGAAGGCA GAGAGTTCAG GTATGGATCC TGGCGGGAGC CAGTCAACCC   1020

CTATTATGTC AATGCCGGCT ATGCCCTGGC CCCAGCCACC AGTGCCAACG ACAGCGAGCA   1080

GCAGAGCCTG TCCAGCGATG CAGACACCCT GTCCCTCACG GACAGCAGCG TGGATGGGAT   1140
```

-continued

```
CCCCCCATAC AGGATCCGTA AGCAGCACCG CAGGGAGATG CAGGAGAGCG CGCAGGTCAA    1200

TGGGCGGGTG CCCCTACCTC ACATTCCCCG CACGTACCGG GTGCCGAAGG AGGTCCGCGT    1260

GGAGCCTCAG AAGTTCGCGG AGGAGCTCAT CCACCGCCTG GAGGCTGTGC AGCGCACGCG    1320

GGAGGCCGAG GAGAAGCTGG AGGAGCGGCT GAAGCGCGTG CGCATGGAGG AGGAAGGTGA    1380

GGACGGCGAT CCATCGTCAG GGCCCCCAGG GCCGTGTCAC AAGCTGCCTC CCGCCCCCGC    1440

TTGGCACCAC TTCCCGCCCC GCTTGTGTTG GACATGGGCT TGTGCCGGGC TCCGGGATGC    1500

ACACGAGGAG AACCCTGAGA GCATCCTGGA CGAGCACGTA CAGCGTGTGC TGAGGACAAC    1560

TGGCCGCCAG TCGCCTGGGC CTGGCCATCG CTCCCCGGAC AGTGGGCACG TGGCCAAGAT    1620

GCCAGTGGCA CTGGGGGGTG CCGCCTCGGG GCACGGGAAG CACGTACCCA AGTCAGGGGC    1680

GAAGCTGGAC GCGGCCGGCC TGCACCACCA CCGACACGTC CACCACCACG TCCACCACAG    1740

CACAGCCCGG CCCAAGGAGC AGGTGGAGGC CGAGGCCACC CGCAGGGCCC AGAGCAGCTT    1800

CGCCTGGGGC CTGGAACCAC ACAGCCATGG GGCAAGGTCC CGAGGCTACT CAGAGAGTGT    1860

TGGCGCTGCC CCCAACGCCA GTGATGGCCT CGCCCACAGT GGGAAGGTGG GCGTTGCGTG    1920

CAAAAGAAAT GCCAAGAAGG CTGAGTCGGG GAAGAGCGCC AGCACCGAGG TGCCAGGTGC    1980

CTCGGAGGAT GCGGAGAAGA ACCAGAAAAT CATGCAGTGG ATCATTGAGG GGAAAAAGGA    2040

GATCAGCAGG CACCGCAGGA CCGGCCACGG GTCTTCGGGG ACGAGGAAGC CACAGCCCCA    2100

TGAGAACTCC AGACCYTTGT CCCTTGAGCA CCCCTGGGCC GGCCCTCAGC TCCGGACCTC    2160

CGTGCAGCCC TCCCACCTCT TCATCCAAGA CCCCACCATG CCACCCCACC CAGCTCCCAA    2220

CCCCCTAACC CAGCTGGAGG AGGCGCGCCG ACGTCTGGAG GAGGAAGAAA AGAGAGCCAG    2280

CCGAGCACCC TCCAAGCAGA GGTATGTGCA GGAGGTTATG CGGCGGGGAC GCGCCTGCGT    2340

CAGGCCAGCG TGCGCGCCGG TGCTGCACGT GGTACCAGCC GTGTCGGACA TGGAGCTCTC    2400

CGAGACAGAG ACAAGATCGC AGAGGAAGGT GGGCGGCGGG AGTGCCCAGC CGTGTGACAG    2460

CATCGTTGTG GCGTACTACT TCTGCGGGGA ACCCATCCCC TACCGCACCC TGGTGAGGGG    2520

CCGCGCTGTC ACCCTGGGCC AGTTCAAGGA GCTGCTGACC AAAAAGGGCA GCTACAGATA    2580

CTACTTCAAG AAAGTGAGCG ACGAGTTTGA CTGTGGGGTG GTGTTTGAGG AGGTTCGAGA    2640

GGACGAGGCC GTCCTGCCCG TCTTTGAGGA GAAGATCATC GGCAAAGTGG AGAAGGTGGA    2700

CTGATAGGCT GGTGGGCTGG CCGCTGTGCC AGGCGAGGCC CTTGGCGGGC ACGGGTGTCA    2760

CGGCCAGGCA GATGACCTCG TACTCAGGAG CCCGATGGGG AACAGTGTTG GGTGTACCAC    2820

CCATCCCTGT GGTCTACCCG TGTCTAGAGG CAGGTAGGGG GTCCCTCCAA GTGGTCCACA    2880

AGCTTCTGTC CTGCCCCCAA GGAGGCAGCC TGGACCACTC CTCATAGCAA TACTTGGAGG    2940

GCCCAGCCCA AGTGAGGCAG CCGAGGTCCC TGCTGCCAGC TTCAGGTGAC CCCCCCCCAT    3000

CCCCCGGCAC CTCCCTTGGG CACGTGTGCT GGGATCTACT TTCCCTCTGG GATTTGCCCA    3060

CGTACCCAGG TCTGGCTGGG GCCCAGGCCC GGATGCAGAG GCCTGCAGGG CCTCTGTCAA    3120

TTGTACGCGC CACCAAGTGC CTTCAACACA GCTTGTCTCT TGCCTGCCAC TGTGTGAATC    3180

GGCGACGGAG CACTGCACCT GCCTCCAGCC GCCGGCTGTG CAGTCCTGGG TCCTCCTTTC    3240

TGAGGGCCCG TGTAAATATG TACATTTCTC AGGCTAGGGC CAGCAGGGGC TGCCCGAGTC    3300

TGTTTTTCAT GCGATGACAC TTGTACAATT ATCTTTTCAA AGGTACTTGG ATAATAATGA    3360

AATAAAACTG TTTTTGAACC TGAATAAAAA AAAAAAAAA AAAAAAAAA A              3411
```

(2) INFORMATION FOR SEQ ID NO:4:

(i) SEQUENCE CHARACTERISTICS:
    (A) LENGTH: 900 amino acids
    (B) TYPE: amino acid
    (C) STRANDEDNESS: single
    (D) TOPOLOGY: linear (ii) MOLECULE TYPE: Protein (xi) SEQUENCE DESCRIPTION: SEQ ID NO:4:

```
Gly Pro Gly Ser Arg His His Arg Ala Arg Asp Arg Leu Ile His Phe
 1               5                  10                  15

Gly Ala Val Ser Thr Asp Val Leu Gly Cys Ser Ala His Cys Ser Leu
             20                  25                  30

Thr Gln Ser Pro Lys Met Asn Ile Gln Glu Gln Gly Phe Pro Leu Asp
         35                  40                  45

Leu Gly Ala Ser Phe Thr Glu Asp Ala Pro Arg Pro Val Pro Gly
     50                  55                  60

Glu Glu Gly Glu Leu Val Ser Thr Asp Pro Arg Pro Ala Ser Tyr Ser
 65                  70                  75                  80

Phe Cys Ser Gly Lys Gly Val Gly Ile Lys Gly Glu Thr Ser Thr Ala
                 85                  90                  95

Thr Pro Arg Arg Ser Asp Leu Asp Leu Gly Tyr Glu Pro Glu Gly Ser
                100                 105                 110

Ala Ser Pro Thr Pro Pro Tyr Leu Lys Trp Ala Glu Ser Leu His Ser
            115                 120                 125

Leu Leu Asp Asp Gln Asp Gly Ile Ser Leu Phe Arg Thr Phe Leu Lys
130                 135                 140

Gln Glu Gly Cys Ala Asp Leu Leu Asp Phe Trp Phe Ala Cys Thr Gly
145                 150                 155                 160

Phe Arg Lys Leu Glu Pro Cys Asp Ser Asn Glu Glu Lys Arg Leu Lys
                165                 170                 175

Leu Ala Arg Ala Ile Tyr Arg Lys Tyr Ile Leu Asp Asn Asn Gly Ile
            180                 185                 190

Val Ser Arg Gln Thr Lys Pro Ala Thr Lys Ser Phe Ile Lys Gly Cys
        195                 200                 205

Ile Met Lys Gln Leu Ile Asp Pro Ala Met Phe Asp Gln Ala Gln Thr
    210                 215                 220

Glu Ile Gln Ala Thr Met Glu Glu Asn Thr Tyr Pro Ser Phe Leu Lys
225                 230                 235                 240

Ser Asp Ile Tyr Leu Glu Tyr Thr Arg Thr Gly Ser Glu Ser Pro Lys
                245                 250                 255

Val Cys Ser Asp Gln Ser Ser Gly Ser Gly Thr Gly Lys Gly Ile Ser
            260                 265                 270

Gly Tyr Leu Pro Thr Leu Asn Glu Asp Glu Glu Trp Lys Cys Asp Gln
        275                 280                 285

Asp Met Asp Glu Asp Asp Gly Arg Asp Ala Ala Pro Pro Gly Arg Leu
    290                 295                 300

Pro Gln Lys Leu Leu Leu Glu Thr Ala Ala Pro Arg Val Ser Ser Ser
305                 310                 315                 320

Arg Arg Tyr Ser Glu Gly Arg Glu Phe Arg Tyr Gly Ser Trp Arg Glu
                325                 330                 335

Pro Val Asn Pro Tyr Tyr Val Asn Ala Gly Tyr Ala Leu Ala Pro Ala
            340                 345                 350

Thr Ser Ala Asn Asp Ser Glu Gln Gln Ser Leu Ser Ser Asp Ala Asp
        355                 360                 365
```

```
Thr Leu Ser Leu Thr Asp Ser Ser Val Asp Gly Ile Pro Pro Tyr Arg
    370                 375                 380
Ile Arg Lys Gln His Arg Arg Glu Met Gln Glu Ser Ala Gln Val Asn
385                 390                 395                 400
Gly Arg Val Pro Leu Pro His Ile Pro Arg Thr Tyr Arg Val Pro Lys
                405                 410                 415
Glu Val Arg Val Glu Pro Gln Lys Phe Ala Glu Leu Ile His Arg
                420                 425                 430
Leu Glu Ala Val Gln Arg Thr Arg Glu Ala Glu Lys Leu Glu Glu
            435                 440                 445
Arg Leu Lys Arg Val Arg Met Glu Glu Glu Gly Glu Asp Gly Asp Pro
450                 455                 460
Ser Ser Gly Pro Pro Gly Pro Cys His Lys Leu Pro Pro Ala Pro Ala
465                 470                 475                 480
Trp His His Phe Pro Pro Arg Leu Cys Trp Thr Trp Ala Cys Ala Gly
                485                 490                 495
Leu Arg Asp Ala His Glu Glu Asn Pro Glu Ser Ile Leu Asp Glu His
                500                 505                 510
Val Gln Arg Val Leu Arg Thr Thr Gly Arg Gln Ser Pro Gly Pro Gly
            515                 520                 525
His Arg Ser Pro Asp Ser Gly His Val Ala Lys Met Pro Val Ala Leu
530                 535                 540
Gly Gly Ala Ala Ser Gly His Gly Lys His Val Pro Lys Ser Gly Ala
545                 550                 555                 560
Lys Leu Asp Ala Ala Gly Leu His His Arg His Val His His His
                565                 570                 575
Val His His Ser Thr Ala Arg Pro Lys Glu Gln Val Glu Ala Glu Ala
            580                 585                 590
Thr Arg Arg Ala Gln Ser Ser Phe Ala Trp Gly Leu Glu Pro His Ser
            595                 600                 605
His Gly Ala Arg Ser Arg Gly Tyr Ser Glu Ser Val Gly Ala Ala Pro
        610                 615                 620
Asn Ala Ser Asp Gly Leu Ala His Ser Gly Lys Val Gly Val Ala Cys
625                 630                 635                 640
Lys Arg Asn Ala Lys Lys Ala Glu Ser Gly Lys Ser Ala Ser Thr Glu
                645                 650                 655
Val Pro Gly Ala Ser Glu Asp Ala Glu Lys Asn Gln Lys Ile Met Gln
                660                 665                 670
Trp Ile Ile Glu Gly Glu Lys Glu Ile Ser Arg His Arg Arg Thr Gly
            675                 680                 685
His Gly Ser Ser Gly Thr Arg Lys Pro Gln Pro His Glu Asn Ser Arg
    690                 695                 700
Pro Leu Ser Leu Glu His Pro Trp Ala Gly Pro Gln Leu Arg Thr Ser
705                 710                 715                 720
Val Gln Pro Ser His Leu Phe Ile Gln Asp Pro Thr Met Pro Pro His
                725                 730                 735
Pro Ala Pro Asn Pro Leu Thr Gln Leu Glu Glu Ala Arg Arg Arg Leu
                740                 745                 750
Glu Glu Glu Glu Lys Arg Ala Ser Arg Ala Pro Ser Lys Gln Arg Tyr
            755                 760                 765
Val Gln Glu Val Met Arg Arg Gly Arg Ala Cys Val Arg Pro Ala Cys
770                 775                 780
```

```
Ala Pro Val Leu His Val Val Pro Ala Val Ser Asp Met Glu Leu Ser
785                 790                 795                 800

Glu Thr Glu Thr Arg Ser Gln Arg Lys Val Gly Gly Ser Ala Gln
                805                 810                 815

Pro Cys Asp Ser Ile Val Val Ala Tyr Tyr Phe Cys Gly Glu Pro Ile
            820                 825                 830

Pro Tyr Arg Thr Leu Val Arg Gly Arg Ala Val Thr Leu Gly Gln Phe
            835                 840                 845

Lys Glu Leu Leu Thr Lys Lys Gly Ser Tyr Arg Tyr Tyr Phe Lys Lys
            850                 855                 860

Val Ser Asp Glu Phe Asp Cys Gly Val Val Phe Glu Glu Val Arg Glu
865                 870                 875                 880

Asp Glu Ala Val Leu Pro Val Phe Glu Glu Lys Ile Ile Gly Lys Val
                885                 890                 895

Glu Lys Val Asp
            900
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GAGGGAGAGA AGGAGATCAG                                              20
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

```
GTAGCTCCCC TTCTTGGTTA G                                            21
```

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
TTGGGAGACA GACATGA                                                 17
```

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TCCTGTTGAC TGCAGACT                                                 18

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CACCAGCCCT CTCTGGAACC                                               20

(2) INFORMATION FOR SEQ ID NO:10:

(i) SEQUENCE CHARACTERISTICS:
        (A) LENGTH: 855 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:10:

```
Asp Phe Gly Ser Ser Pro Ala Val Gln Thr Ser Ala Arg Lys Met Asn
 1               5                  10                  15

Ile Gln Gly Lys Gly Phe Pro Leu Asp Leu Gly Arg Ser Phe Thr Glu
                20                  25                  30

Asp Ala Pro Arg Pro Val Pro Gly Glu Glu Gly Glu Leu Val Ser
            35                  40                  45

Thr Asp Pro Arg Pro Val Ser His Gly Phe Tyr Ser Ser Lys Ser Asp
 50                  55                  60

Ala Val Arg Asn Glu Thr Ser Thr Ala Thr Pro Arg Arg Ser Asp Leu
 65                  70                  75                  80

Asp Leu Gly Tyr Glu Pro Glu Gly Ser Ala Ser Pro Thr Pro Pro Tyr
                85                  90                  95

Leu Lys Trp Ala Glu Ser Leu His Ser Leu Leu Asp Asp Gln Asp Gly
                100                 105                 110

Ile Asn Leu Phe Arg Thr Phe Leu Lys Gln Glu Asp Cys Ala Asp Leu
                115                 120                 125

Leu Asp Phe Trp Phe Ala Cys Ser Gly Phe Arg Lys Leu Glu Pro Cys
            130                 135                 140

Val Ser Asn Glu Glu Lys Arg Leu Lys Leu Ala Lys Ala Ile Tyr Lys
145                 150                 155                 160

Lys Tyr Ile Leu Asp Asn Asn Gly Ile Val Ser Arg Gln Ile Lys Pro
                165                 170                 175

Ala Thr Lys Ser Phe Ile Lys Asp Cys Val Met Lys Leu Gln Ile Asp
                180                 185                 190

Pro Asp Met Phe Asp Gln Ala Gln Thr Glu Ile Gln Cys Met Ile Glu
            195                 200                 205

Asp Asn Thr Tyr Pro Leu Phe Leu Lys Ser Asp Ile Tyr Leu Glu Tyr
            210                 215                 220

Thr Arg Thr Gly Gly Glu Ser Pro Lys Ile Tyr Ser Asp Pro Ser Ser
225                 230                 235                 240

Gly Ser Gly Thr Gly Lys Gly Leu Pro Gly Tyr Leu Pro Thr Leu Asn
```

```
                245                 250                 255
Glu Asp Glu Glu Trp Lys Cys Asp Gln Asp Thr Glu Pro Glu Ala Ser
                260                 265                 270
Arg Asp Ser Ala Pro Ser Ser Arg Leu Thr Gln Lys Leu Leu Leu Glu
            275                 280                 285
Thr Ala Thr Gln Arg Ala Thr Ser Thr Arg Arg Tyr Ser Glu Gly Arg
        290                 295                 300
Glu Phe Arg His Gly Ser Trp Arg Glu Pro Val Asn Pro Tyr Tyr Val
305                 310                 315                 320
Asn Thr Gly Tyr Ala Met Ala Pro Ala Thr Ser Ala Asn Asp Ser Glu
                325                 330                 335
Gln Gln Ser Met Ser Ser Asp Ala Asp Thr Met Ser Leu Thr Asp Ser
            340                 345                 350
Ser Ile Asp Gly Ile Pro Pro Tyr Arg Leu Arg Lys Gln His Arg Arg
        355                 360                 365
Glu Met Gln Glu Ser Ala Lys Ala Asn Gly Arg Val Pro Leu Pro His
370                 375                 380
Ile Pro Arg Thr Tyr Arg Met Pro Lys Asp Ile His Val Glu Pro Glu
385                 390                 395                 400
Lys Phe Ala Ala Glu Leu Ile Asn Arg Leu Glu Glu Val Gln Lys Glu
                405                 410                 415
Arg Glu Ala Glu Glu Lys Leu Glu Glu Arg Leu Lys Arg Val Arg Ala
            420                 425                 430
Glu Glu Glu Gly Glu Asp Ala Asp Ile Ser Ser Gly Pro Ser Val Ile
        435                 440                 445
Ser His Lys Met Pro Ser Ala Gln Pro Phe His His Phe Ala Pro Arg
    450                 455                 460
Tyr Ser Glu Met Gly Cys Ala Gly Met Gln Met Arg Asp Ala His Glu
465                 470                 475                 480
Glu Asn Pro Glu Ser Ile Leu Asp Glu His Val Gln Arg Val Met Lys
                485                 490                 495
Thr Pro Gly Cys Gln Ser Pro Gly Pro Gly Arg His Ser Pro Lys Pro
            500                 505                 510
Arg Ser Pro Glu Ser Gly His Leu Gly Lys Leu Ser Gly Thr Leu Gly
        515                 520                 525
Thr Ile Pro Pro Gly His Gly Lys His Thr Thr Lys Ser Gly Met Lys
    530                 535                 540
Leu Asp Ala Ala Asn Leu Tyr His His Lys His Val Tyr His His Ile
545                 550                 555                 560
His His His Ser Met Met Lys Pro Lys Glu Gln Ile Glu Ala Glu Ala
                565                 570                 575
Thr Gln Arg Val Gln Asn Ser Phe Ala Trp Asn Val Asp Ser His Asn
            580                 585                 590
Tyr Ala Thr Lys Ser Arg Asn Tyr Ser Glu Asn Leu Gly Met Ala Pro
        595                 600                 605
Val Pro Met Asp Ser Leu Gly Tyr Ser Gly Lys Ala Ser Leu Leu Ser
    610                 615                 620
Lys Arg Asn Ile Lys Lys Thr Asp Ser Gly Lys Ser Asp Gly Ala Asn
625                 630                 635                 640
Tyr Glu Met Pro Gly Ser Pro Glu Asp Val Glu Arg Asn Gln Lys Ile
                645                 650                 655
Leu Gln Trp Ile Ile Glu Gly Glu Lys Glu Ile Ser Arg His Lys Lys
            660                 665                 670
```

```
Thr Asn His Gly Ser Ser Gly Val Lys Lys Gln Leu Ser His Asp Met
        675                 680                 685

Val Arg Pro Leu Ser Ile Glu Arg Pro Val Ala Val His Pro Trp Val
        690                 695                 700

Ser Ala Gln Leu Arg Asn Val Val Gln Pro Ser His Pro Phe Ile Gln
705                 710                 715                 720

Asp Pro Thr Met Pro Pro Asn Pro Ala Pro Asn Pro Leu Thr Gln Leu
                725                 730                 735

Glu Glu Ala Arg Arg Arg Leu Glu Glu Glu Lys Arg Ala Gly Lys
                740                 745                 750

Leu Pro Leu Lys Gln Arg Leu Lys Pro Gln Lys Arg Pro Gly Ser Gly
        755                 760                 765

Ala Ser Gln Pro Cys Glu Asn Ile Val Val Ala Tyr Tyr Phe Cys Gly
        770                 775                 780

Glu Pro Ile Pro Tyr Arg Thr Leu Val Lys Gly Arg Val Val Thr Leu
785                 790                 795                 800

Gly Gln Phe Lys Glu Leu Leu Thr Lys Lys Gly Asn Tyr Arg Tyr Tyr
                805                 810                 815

Phe Lys Lys Val Ser Asp Glu Phe Asp Cys Gly Val Val Phe Glu Glu
                820                 825                 830

Val Arg Glu Asp Asp Thr Ile Leu Pro Ile Phe Glu Glu Lys Ile Ile
        835                 840                 845

Gly Lys Val Glu Lys Ile Asp
        850                 855

(2) INFORMATION FOR SEQ ID NO:11:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:11:

Leu Trp Ser Glu Ala Phe Asp Glu Leu Leu Ala Ser Lys Tyr Gly Leu
1               5                   10                  15

Ala Ala Phe Arg Ala Phe Leu Lys Ser Glu Phe Cys Glu Glu Asn Ile
                20                  25                  30

Glu Phe Trp Leu Ala Cys Glu Asp Phe Lys Lys Thr Lys Ser Pro Gln
            35                  40                  45

Lys Leu Ser Ser Lys Ala Arg Lys Ile Tyr Thr Asp Phe Ile Glu Lys
50                  55                  60

Glu Ala Pro Lys Glu Ile Asn Ile Asp Phe Gln Thr Lys Thr Leu Ile
65                  70                  75                  80

Ala Gln Asn Ile Gln Glu Ala Thr Ser Gly Cys Phe Thr Thr Ala Gln
                85                  90                  95

Lys Arg Val Tyr Ser Leu Met Glu Asn Asn Ser Tyr Pro Arg Phe Leu
                100                 105                 110

Glu Ser Glu Phe Tyr Gln Asp Leu
            115                 120

(2) INFORMATION FOR SEQ ID NO:12:

(i) SEQUENCE CHARACTERISTICS:
        (A) LENGTH: 120 amino acids
```

(B) TYPE: amino acid
          (C) STRANDEDNESS: single
          (D) TOPOLOGY: linear (ii) MOLECULE TYPE: Protein (xi) SEQUENCE DESCRIPTION: SEQ ID NO:12:

Gln Trp Arg Asp Ser Leu Asp Lys Leu Leu Gln Asn Asn Tyr Gly Leu
1               5                   10                  15

Ala Ser Phe Lys Ser Phe Leu Lys Ser Glu Phe Ser Glu Glu Asn Leu
            20                  25                  30

Glu Phe Gln Ile Ala Cys Glu Asp Tyr Lys Lys Ile Lys Ser Pro Ala
        35                  40                  45

Lys Met Ala Glu Lys Ala Lys Gln Ile Tyr Glu Glu Phe Ile Gln Thr
    50                  55                  60

Glu Ala Pro Lys Glu Val Asn Ile Asp His Phe Thr Lys Asp Ile Thr
65                  70                  75                  80

Met Lys Asn Leu Val Glu Pro Ser Leu Ser Ser Phe Asp Met Ala Gln
                85                  90                  95

Lys Arg Ile His Ala Leu Met Glu Lys Asp Ser Leu Pro Arg Phe Val
                100                 105                 110

Arg Ser Glu Phe Tyr Gln Glu Leu
            115                 120

(2) INFORMATION FOR SEQ ID NO:13:

(i) SEQUENCE CHARACTERISTICS:
          (A) LENGTH: 120 amino acids
          (B) TYPE: amino acid
          (C) STRANDEDNESS: single
          (D) TOPOLOGY: linear (ii) MOLECULE TYPE: Protein (xi) SEQUENCE DESCRIPTION: SEQ ID NO:13:

Lys Trp Gly Glu Ser Leu Glu Lys Leu Leu Val His Lys Tyr Gly Leu
1               5                   10                  15

Ala Val Phe Gln Ala Phe Leu Arg Thr Glu Phe Ser Glu Glu Asn Leu
            20                  25                  30

Glu Phe Trp Leu Ala Cys Glu Asp Phe Lys Lys Val Lys Ser Gln Ser
        35                  40                  45

Lys Met Ala Ser Lys Ala Lys Lys Ile Phe Ala Glu Tyr Ile Ala Ile
    50                  55                  60

Gln Ala Cys Lys Glu Val Asn Leu Asp Ser Tyr Thr Arg Glu His Thr
65                  70                  75                  80

Lys Asp Asn Leu Gln Ser Val Thr Arg Gly Cys Phe Asp Leu Ala Gln
                85                  90                  95

Lys Arg Ile Phe Gln Leu Met Glu Lys Asp Ser Tyr Pro Arg Phe Leu
                100                 105                 110

Arg Ser Asp Leu Tyr Leu Asp Leu
            115                 120

(2) INFORMATION FOR SEQ ID NO:14:

(i) SEQUENCE CHARACTERISTICS:
          (A) LENGTH: 120 amino acids
          (B) TYPE: amino acid
          (C) STRANDEDNESS: single
          (D) TOPOLOGY: linear (ii) MOLECULE TYPE: Protein (xi) SEQUENCE DESCRIPTION: SEQ ID NO:14:

Lys Trp Ala Glu Ser Leu Glu Asn Leu Ile Ser His Glu Cys Gly Leu
1               5                   10                  15

Ala Ala Phe Lys Ala Phe Leu Lys Ser Glu Tyr Ser Glu Glu Asn Ile
            20                  25                  30

Asp Phe Trp Ile Ser Cys Glu Gly Tyr Lys Lys Ile Lys Ser Pro Ser
        35                  40                  45

Lys Leu Ser Pro Lys Ala Lys Lys Ile Tyr Asn Glu Phe Ile Ser Val
50                  55                  60

Gln Ala Thr Lys Glu Val Asn Leu Asp Ser Cys Thr Arg Glu Glu Thr
65                  70                  75                  80

Ser Arg Asn Met Leu Glu Pro Thr Ile Thr Cys Phe Asp Glu Ala Gln
                85                  90                  95

Lys Lys Ile Phe Asn Leu Met Glu Lys Asp Ser Tyr Arg Arg Phe Leu
            100                 105                 110

Lys Ser Arg Phe Tyr Leu Asp Leu
            115                 120

(2) INFORMATION FOR SEQ ID NO:15:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:15:

Gln Trp Ser Gln Ser Leu Glu Lys Leu Leu Ala Asn Gln Thr Gly Gln
1               5                   10                  15

Asn Val Phe Gly Ser Phe Leu Lys Ser Glu Phe Ser Glu Glu Asn Ile
            20                  25                  30

Glu Phe Trp Leu Ala Cys Glu Asp Tyr Lys Lys Thr Glu Ser Asp Leu
        35                  40                  45

Leu Pro Cys Lys Ala Glu Glu Ile Tyr Lys Ala Phe Val His Ser Asp
50                  55                  60

Ala Ala Lys Gln Ile Asn Ile Asp Phe Arg Thr Arg Glu Ser Thr Ala
65                  70                  75                  80

Lys Lys Ile Lys Ala Pro Thr Pro Thr Cys Phe Asp Glu Ala Gln Lys
            85                  90                  95

Val Ile Tyr Thr Leu Met Glu Lys Asp Ser Tyr Pro Arg Phe Leu Lys
            100                 105                 110

Ser His Ile Tyr Leu Asn Leu
            115

(2) INFORMATION FOR SEQ ID NO:16:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:16:

Ser Trp Ala Gln Ser Phe Asp Lys Leu Met His Ser Pro Ala Gly Arg
1               5                   10                  15

```
Ser Val Phe Arg Ala Phe Leu Arg Thr Glu Tyr Ser Glu Glu Asn Met
            20                  25                  30

Leu Phe Trp Leu Ala Cys Glu Glu Leu Lys Ala Glu Ala Asn Gln His
            35                  40                  45

Val Val Asp Glu Lys Ala Arg Leu Ile Tyr Glu Asp Tyr Val Ser Ile
            50                  55                  60

Leu Ser Pro Lys Glu Val Ser Leu Asp Ser Arg Val Arg Glu Gly Ile
65                  70                  75                  80

Asn Lys Lys Met Gln Glu Pro Ser Ala His Thr Phe Asp Asp Ala Gln
                85                  90                  95

Leu Gln Ile Tyr Thr Leu Met His Arg Asp Ser Tyr Pro Arg Phe Leu
            100                 105                 110

Ser Ser Pro Thr Tyr Arg Ala Leu
            115                 120

(2) INFORMATION FOR SEQ ID NO:17:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:17:

Arg Trp Gly Phe Gly Met Asp Glu Ala Leu Lys Asp Pro Val Gly Arg
                5                   10                  15

Glu Gln Phe Leu Lys Phe Leu Ser Glu Phe Ser Ser Glu Asn Leu
            20                  25                  30

Arg Phe Trp Leu Ala Val Glu Asp Leu Lys Lys Arg Pro Ile Lys Glu
            35                  40                  45

Val Pro Ser Arg Val Gln Glu Ile Trp Gln Glu Phe Leu Ala Pro Gly
            50                  55                  60

Ala Pro Ser Ala Ile Asn Leu Asp Ser Lys Ser Tyr Asp Lys Thr Thr
65                  70                  75                  80

Gln Asn Val Lys Glu Pro Gly Arg Tyr Thr Phe Glu Asp Ala Gln Glu
                85                  90                  95

His Ile Tyr Lys Leu Met Lys Ser Asp Ser Tyr Pro Arg Phe Ile Arg
            100                 105                 110

Ser Ser Ala Tyr Gln Glu Leu
            115

(2) INFORMATION FOR SEQ ID NO:18:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:18:

Lys Trp Ala Ala Ser Leu Glu Asn Leu Leu Glu Asp Pro Glu Gly Val
1                   5                   10                  15

Lys Arg Phe Arg Glu Phe Leu Lys Lys Glu Phe Ser Glu Glu Asn Val
            20                  25                  30

Leu Phe Trp Leu Ala Cys Glu Asp Phe Lys Lys Met Gln Asp Lys Thr
```

```
                 35                  40                  45
Gln Met Gln Glu Lys Ala Lys Glu Ile Tyr Met Thr Phe Leu Ser Ser
     50                  55                  60

Lys Ala Ser Ser Gln Val Asn Val Glu Gly Gln Ser Arg Leu Asn Glu
 65                  70                  75                  80

Lys Ile Leu Glu Glu Pro His Pro Leu Met Phe Gln Lys Leu Gln Asp
                 85                  90                  95

Gln Ile Phe Asn Leu Met Lys Tyr Asp Ser Tyr Ser Arg Phe Leu Lys
                100                 105                 110

Ser Asp Leu Phe Leu Lys His
                115
```

(2) INFORMATION FOR SEQ ID NO:19:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:19:

```
Arg Trp Ala Glu Ser Leu His Ser Leu Leu Asp Asp Gln Asp Gly Ile
 1               5                  10                  15

Ser Leu Phe Arg Thr Phe Leu Lys Gln Glu Gly Cys Ala Asp Leu Leu
                 20                  25                  30

Asp Phe Trp Phe Ala Cys Ser Gly Phe Arg Lys Leu Glu Pro Cys Asp
                 35                  40                  45

Ser Asn Glu Glu Lys Arg Leu Lys Leu Ala Arg Ala Ile Tyr Arg Lys
     50                  55                  60

Tyr Ile Leu Asp Ser Asn Gly Ile Val Ser Arg Gln Thr Lys Pro Ala
 65                  70                  75                  80

Thr Lys Ser Phe Ile Lys Asp Cys Val Met Lys Gln Gln Ile Asp Pro
                 85                  90                  95

Ala Met Phe Asp Gln Ala Gln Thr Glu Ile Gln Ser Thr Met Glu Glu
                100                 105                 110

Asn Thr Tyr Pro Ser Phe Leu Lys Ser Asp Ile Tyr Leu Glu Tyr
                115                 120                 125
```

(2) INFORMATION FOR SEQ ID NO:20:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:20:

```
Val Thr Leu Ala Asp Phe Lys Asn Val Leu Ser Asn Arg Pro Val His
 1               5                  10                  15

Ala Tyr Lys Phe Phe Phe Lys Ser Met Asp Gln Asp Phe Gly Val Val
                 20                  25                  30

Lys Glu Glu Ile Phe Asp Asp Asn Ala Lys Leu Pro Cys Phe Asn Gly
                 35                  40                  45

Arg Val Val
     50
```

(2) INFORMATION FOR SEQ ID NO:21:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:21:

```
Ile Thr Leu Gly Asp Phe Lys Ser Val Leu Gln Arg Pro Ala Gly Ala
1               5                   10                  15

Lys Tyr Phe Phe Lys Ser Met Asp Gln Asp Phe Gly Val Val Lys Glu
            20                  25                  30

Glu Ile Ser Asp Asp Asn Ala Arg Leu Pro Cys Phe Asn Gly Arg Val
        35                  40                  45

Val
```

(2) INFORMATION FOR SEQ ID NO:22:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:22:

```
Val Thr Leu Arg Asp Phe Lys Leu Val Leu Asn Lys Gln Asn Asn Asn
1               5                   10                  15

Tyr Lys Tyr Phe Phe Lys Ser Met Asp Ala Asp Phe Gly Val Val Lys
            20                  25                  30

Glu Glu Ile Ala Asp Asp Ser Thr Ile Leu Pro Cys Phe Asn Gly Arg
        35                  40                  45

Val Val
    50
```

(2) INFORMATION FOR SEQ ID NO:23:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:23:

```
Val Thr Leu Gly Gln Phe Lys Glu Leu Leu Thr Lys Lys Gly Ser Tyr
1               5                   10                  15

Arg Tyr Tyr Phe Lys Lys Val Ser Asp Glu Phe Asp Cys Gly Val Val
            20                  25                  30

Phe Glu Glu Val Arg Glu Asp Glu Pro Val Leu Pro Val Phe Glu Glu
        35                  40                  45

Lys Ile Ile
    50
```

AXIN GENE AND USES THEREOF

The invention disclosed herein was made with Government support under Grant No. DK-46934 from the National Institutes of Health of the United States Department of Health and Human Services. Accordingly, the U.S. Government has certain rights in this invention.

Throughout this application, various publications are referenced in parenthesis. Full citations for these publications may be found listed at the end of the specification. The disclosures of these publications in their entireties are hereby incorporated by reference into this application in order to more fully describe the state of the art as known to those skilled therein.

INTRODUCTION

A fundamental problem in mammalian embryology is the mechanism by which the egg cylinder, an epithelial cup in which only the dorsal-ventral axis is established, gives rise to an embryo with anterior-posterior (A-P) polarity. In the mouse, the earliest morphological manifestation of the A-P axis is the delamination of mesoderm in the primitive streak at ~E6.5. The position of the streak cannot be predicted by earlier morphological asymmetries in the embryo (Gardner et al., 1992), and the regulative abilities of early mouse embryos appear to rule out axis determination by localized determinants from the egg. While a few secreted factors or transcription factors are expressed asymmetrically in the egg cylinder shortly before primitive streak formation, and thus might be involved in induction of the streak, their roles in this process have not been established (reviewed by Bachvarova, 1996; Conlon and Beddington, 1995).

In the amphibian embryo, the dorsal-ventral axis (the second axis to be specified, analogous to the A-P axis of the mouse) is determined by the point of sperm entry and subsequent cortical rotation. This rotation generates the Nieuwkoop Center, a group of dorsal/vegetal blastomeres that induce formation of the Spemann organizer. Transplantation of the Nieuwkoop Center or the organizer to an ectopic position induces the formation of a complete secondary axis, i.e., notochord, somites, neural tube, and head structures (reviewed by Slack, 1994). Recent studies suggest that the formation of the Nieuwkoop Center depends on activation of components of the Wnt signaling pathway (Carnac et al., 1996; Fagotto et al., 1997; Wylie et al., 1996). The Wnts are a family of secreted polypeptides related to Drosophila wingless, whose receptors are believed to be members of the frizzled family (reviewed by Miller and Moon, 1996). The next known component of the signaling pathway is Dishevelled (Dsh), a cytoplasmic protein that, when activated by a Wnt signal, inhibits the activity of glycogen synthase kinase-3 (GSK-3). In the absence of a Wnt signal, GSK-3 activity leads (directly or indirectly) to the phosphorylation and consequent degradation of β-catenin. In the presence of a Wnt signal, GSK-3 is inhibited, increasing the cytosolic level of β-catenin, and promoting its interaction with downstream effectors.

A role for the Wnt signaling pathway in development of the amphibian embryonic axis was revealed by the ability of several Wnts, or downstream factors, to induce an ectopic axis when injected into Xenopus embryos (Miller and Moon, 1996). Furthermore, components of this pathway are required for normal axial development because depletion of maternal β-catenin mRNA (Heasman et al., 1994), or sequestration of β-catenin to the plasma membrane (Fagotto et al., 1996), results in ventralized embryos that fail to develop a dorsal axis. However, it is not clear whether a Wnt ligand triggers Nieuwkoop Center formation, or whether downstream components of the Wnt pathway are activated by some other mechanism (Hoppler et al., 1996; Miller and Moon, 1996; Sokol, 1996). The Nieuwkoop Center is thought to induce a Spemann organizer by secreting a (yet to be identified) diffusible signal (Fagotto et al., 1997; Wylie et al., 1996), which may act synergistically with mesoderm-inducing factors, such as Activin and Vg1, to activate the expression of dorsal-specific genes, such as Goosecoid (Watabe et al., 1995). Dorsoventral patterning of the mesoderm is further controlled by opposing signals emanating from the organizer and the ventral mesoderm: a ventral bone morphogenetic protein (BMP) signal represses dorsal genes, while in the dorsal side the secreted factors Noggin, Chordin and Follistatin directly inhibit BMPs (Hogan, 1996).

While little is known about the molecular control of axis formation in mammalian embryos, a potential source of insight is the study of mouse mutants that affect this process (Conlon and Beddington, 1995; St-Jacques and McMahon, 1996), such as Fused (Fu). Two spontaneous alleles of Fu, called Kinky ($Fu^{Ki}$) and Knobbly ($Fu^{Kb}$), and a transgenic insertional allele, $Fu^{Tg1}$ (previously called Hϵ46), carry recessive mutations that are lethal at E8–E10 (Gluecksohn-Schoenheimer, 1949; Jacobs-Cohen et al., 1984; Perry et al., 1995). In addition to neuroectodermal and cardiac abnormalities, a remarkable property of many early post-implantation embryos homozygous for these three mutant alleles is a duplication of the embryonic axis. This phenotype, unique among mouse mutants, led nearly 40 years ago to the suggestion that Fu may play a role in the specification of the embryonic axis (Gluecksohn-Schoenheimer, 1949). Kinky, Knobbly and a third spontaneous allele, Fused ($Fu^{Fu}$), but not $Fu^{Tg1}$, also have dominant effects that include transient bifurcations of the fetal tailbud, asymmetric fusion of vertebrae leading to tail kinks, deafness, and neurological defects (Lyon et al., 1996).

The cloning of this locus with the aid of a transgene insertion was previously described (Perry et al., 1995). Here, the isolation and sequence of cDNA clones, and the genomic structure of the wild type (WT) and $Fu^{Tg1}$ alleles are reported. Analysis of the $Fu^{Fu}$ and $Fu^{Kb}$ alleles (Vasicek et al., manuscript submitted) has shown that both are caused by retroviral insertions. Because two mutant alleles causing axial duplications in homozygous embryos, $Fu^{Tg1}$ and $Fu^{Kb}$, disrupt production of the major mRNA, the normal gene product may negatively regulate a critical step in the formation of the embryonic axis. This hypothesis is supported by studies in Xenopus embryos, which demonstrate that dorsal injection of WT Fused mRNA blocks axis formation, while ventral injection of a dominant-negative mutant form induces an ectopic axis. Co-injection with factors acting at various steps in axis formation reveals that Fused exerts its effects at a very early stage, by specifically inhibiting signal transduction through the Wnt pathway in the Nieuwkoop Center. Thus, analysis of the Fu locus has identified a novel inhibitor of the Wnt signaling pathway, and suggests that the same pathway regulates an early step in embryonic axis formation in mammals and amphibians. To avoid confusion with the unrelated Drosophila gene fused, applicants have renamed the Fu gene "Axin", for "axis inhibition".

SUMMARY OF THE INVENTION

This invention provides an isolated nucleic acid which encodes Axin.

This invention also provides an isolated nucleic acid which encodes a polypeptide comprising the amino acid sequence of Axin.

This invention also provides a polypeptide comprising the amino acid sequence of Axin. This invention also provides a purified wildtype Axin or purified mutant Axin.

This invention also provides an oligonucleotide of at least 15 nucleotides capable of specifically hybridizing with a sequence of nucleotides present within a nucleic acid which encodes wildtype Axin without hybridizing to a nucleic acid which encodes mutant Axin, and an oligonucleotide of at least 15 nucleotides capable of specifically hybridizing with a sequence of nucleotides present within the nucleic acid which encodes mutant Axin without hybridizing to a nucleic acid which encodes wildtype Axin.

This invention also provides a method for determining whether a subject carries a mutation in the axin gene which comprises (a) obtaining an appropriate nucleic acid sample from the subject and (b) determining whether the nucleic acid sample from step (a) is, or is derived from, a nucleic acid which encodes mutant Axin so as to thereby determine whether a subject carries a mutation in the axin gene.

This invention further provides a method for determining whether a subject has a predisposition for cancer which comprises (a) obtaining an appropriate nucleic acid sample from the subject; and (b) determining whether the nucleic acid sample from step (a) is, or is derived from, a nucleic acid which encodes mutant Axin so as to thereby determine whether a subject has a predisposition for cancer.

This invention further provides a method for treating a subject who has a predisposition to cancer by either introducing the isolated nucleic acid encoding the wildtype Axin or an effective amount of the wildtype human homolog of Axin and a pharmaceutically acceptable carrier, so as to thereby treat the subject who is susceptible to cancer.

This invention also provides a method for determining whether a subject has cancer, which comprises (a) obtaining an appropriate nucleic acid sample from the subject; and (b) determining whether the nucleic acid sample from step (a) is, or is derived from, a nucleic acid which encodes mutant Axin so as to thereby determine whether a subject has cancer.

This invention also provides a method for detecting a mutation in cancerous cells of the subject which comprises (a) obtaining an appropriate nucleic acid sample from the subject; and (b) determining whether the nucleic acid sample from step (a) is, or is derived from, a nucleic acid which encodes mutant Axin so as to thereby detect a mutation in the cancerous cells of the subject.

This invention further provides a method of suppressing cells unable to regulate themselves by either introducing the isolated nucleic acid encoding wildtype Axin or wildtype Axin in an amount effective enough to suppress the cells.

This invention further provides a method of treating a subject who has cancer by either introducing the isolated nucleic acid encoding wildtype Axin or the protein itself in an effective amount.

This invention further provides a method for identifying a chemical compound which is capable of suppressing cells unable to regulate themselves in a subject which comprises (a) contacting mutant Axin with the chemical compound under conditions permitting binding between the mutant Axin and the chemical compound; (b) detecting specific binding of the chemical compound to the mutant Axin; and (c) determining whether the chemical compound inhibits the mutant Axin so as to identify a chemical compound which is capable of suppressing cells unable to regulate themselves.

This invention further provides pharmaceutical composition comprising a chemical compound capable of inhibiting cancer, an antisense molecule capable of inhibiting an isolated nucleic acid encoding mutant Axin, or purified Axin in an amount effective to treat cancer and a pharmaceutically effective carrier.

This invention further provides a method of treating a subject who has cancer comprising administration of an effective amount of the above-identified pharmaceutical composition.

This invention further provides transgenic, nonhuman mammal comprising an isolated nucleic acid encoding Axin, specifically the mutant protein.

BRIEF DESCRIPTION OF THE FIGURES

Abbreviations: The amino acid residues are abbreviated as follows: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr. CON: consensus sequence.

Figure 1:
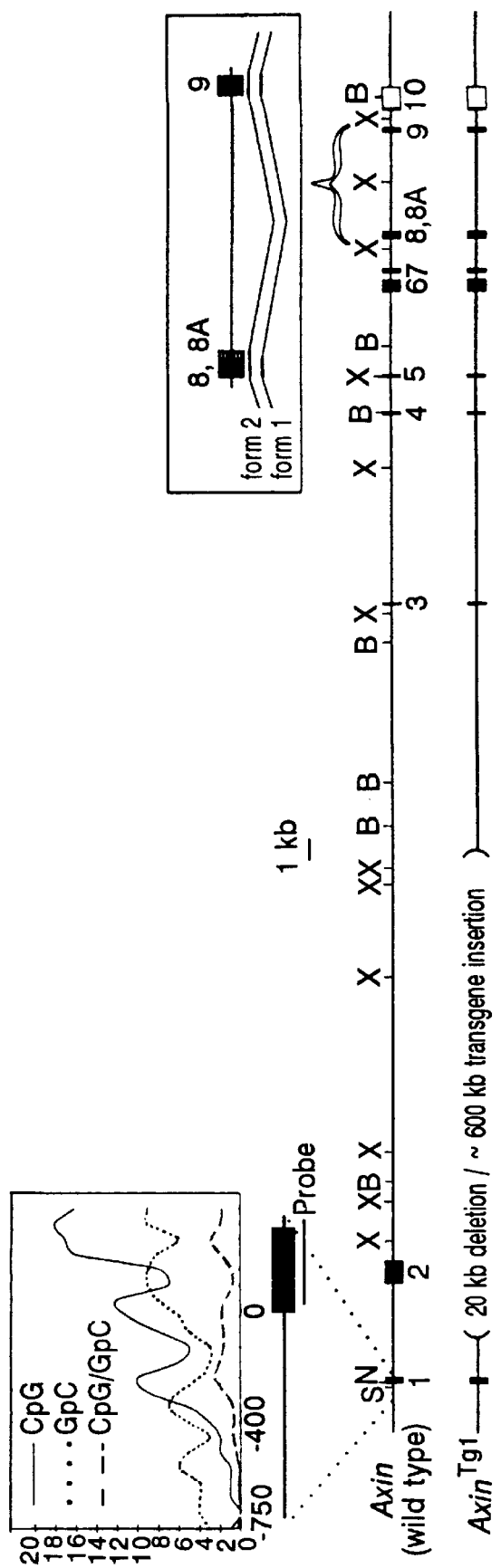
FIG. 1. Structure of the WT Axin gene and the transgenic allele $Axin^{Tg1}$. In $Axin^{Tg1}$, a random transgene insertion (Perry et al., 1995) was accompanied by a deletion including exon 2. Exon 1 is located in a CpG island, as indicated by the frequency of CpG or GpC dinucleotides per 100 bp, and the ratio of CpG/GpC, calculated at 50 bp intervals (left inset). A genomic probe used to isolate cDNA clones is indicated below the inset. The open box in exon 10 represents the 3' UTR. The inset at right shows the origin of form 1 and 2 alternatively spliced mRNAs. The cDNA sequences corresponding to exon 1 are 1–308; exon 2, 309–1267; exon 3, 1268–1408; exon 4, 1409–1505; exon 5, 1506–1643; exon 6, 1644–2161; exon 7, 2162–2332; exon 8, 2333–2578; exon 8A, 2579–2686; exon 9, 2687–2854; and exon 10, 2855–3731. The RGS region is encoded in exon 2, and the Dsh homology in exons 9–10. Restriction sites: N, NotI; S, SacII; X, XbaI; B, BamHI.

2A. Northern blot. ES cells are WT (+/+) or $Axin^{Tg1/Tg1}$ (−/−). Sg, salivary gland; Th, thymus; Te, testis; Lu, lung; He, heart; Ki, kidney; Br, brain; Ov, ovary; Sp, spleen; Li, liver.

2B. Whole mount in situ hybridization analysis of Axin mRNA in (left to right) two E7.5, two E8.5 and one E9.5 WT embryos. Scale bar, 0.2 mm.

2C. Expression of both mRNA isoforms in tissues and ES cells, detected by RT-PCR using primers flanking the 108 bp sequence encoded by exon 8A. The upper band (563 bp) represents form 2 mRNA and the lower band (455 bp) form 1. C, control with no added cDNA. m, 123 bp ladder.

FIGS. 3A–3D. Amino acid sequence of mouse Axin and its human and chicken homologs, and similarity to RGS and Dsh proteins.

3A–3B. Mouse (m) (SEQ ID NO: 1), human (h) (SEQ ID NO: 4) and chick (c) (SEQ ID NO: 10) Axin sequences. Identical residues are highlighted in black, blue or red and conserved residues in gray. RGS and Dsh homologies are highlighted in blue and red, respectively. The mouse sequence begins with the first residue encoded by the cDNA sequence, and the first two Met residues are indicated by *. Also indicated is a 36 aa segment included in murine and human form 2. The mouse and human form 1 and the chicken sequence contain a bipartite NLS consensus at position 749 (K/R, K/R, 10 aa spacer, followed by 3 K/R in the next 5 residues), which is interrupted in form 2. In addition, mAxin includes a second NLS at aa 59. The murine sequence contains one consensus site for tyrosine phosphorylation (aa 192–199), and several for cAMP- and cGMP-dependent protein kinase, protein kinase C, casein kinase II, and GSK-3. The site of intron 6, where Axin$^{Fu}$ contains a proviral insertion, is marked by a green triangle, and the site where exon 7 is interrupted in Axin$^{Kb}$, by a magenta triangle.

3C. Alignment of the RGS domains of Axin and 8 human or rat RGS proteins (SEQ ID NO: 11, 12, 13, 14, 15, 16, 17, 18 and 19).

3D. Alignment of a 51 aa segment of Axin with a similar region in Drosophila Dsh and two murine homologs (SEQ ID NO: 20, 21, 22 and 23).

Figure 4A:
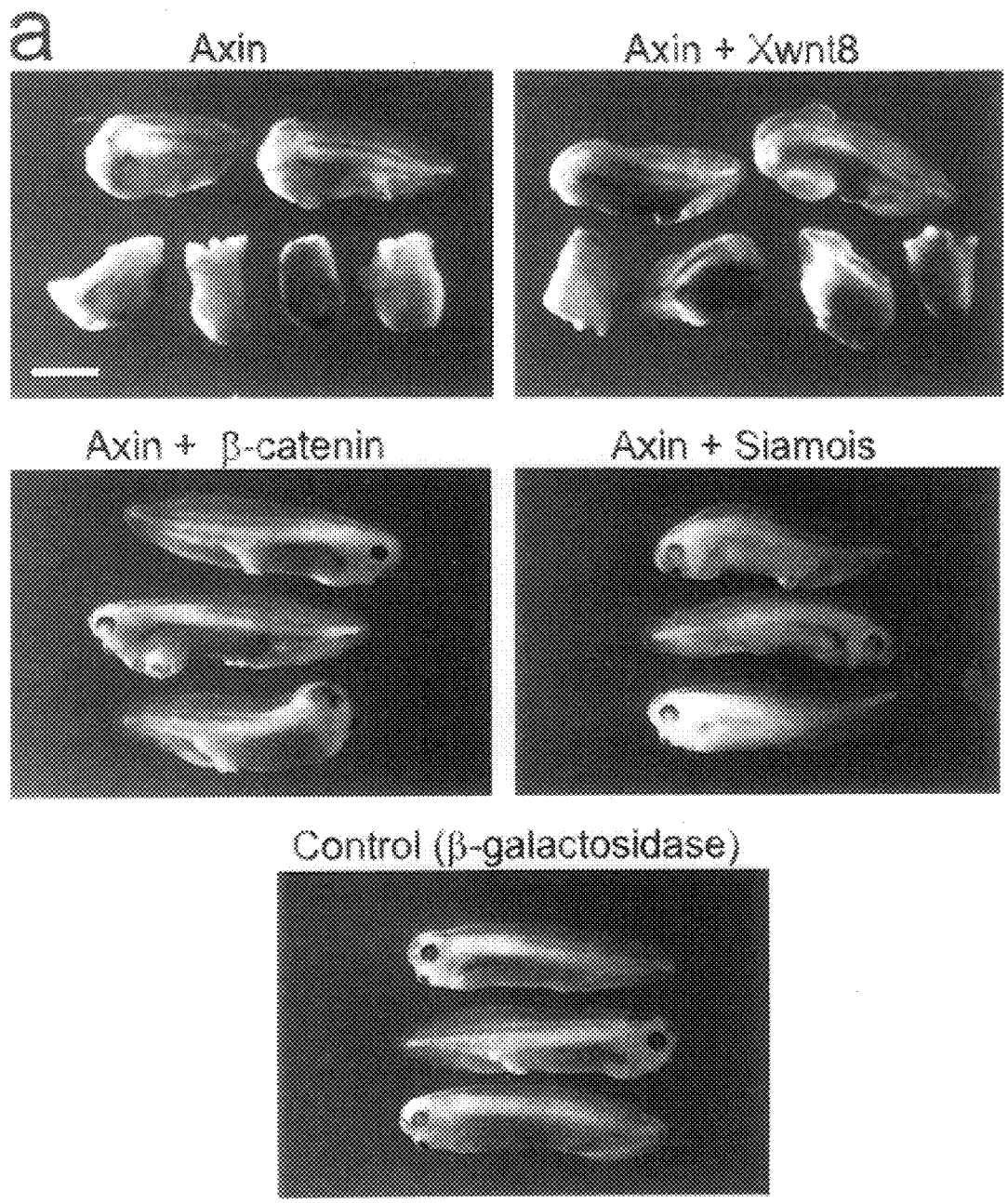
Figure 4B:
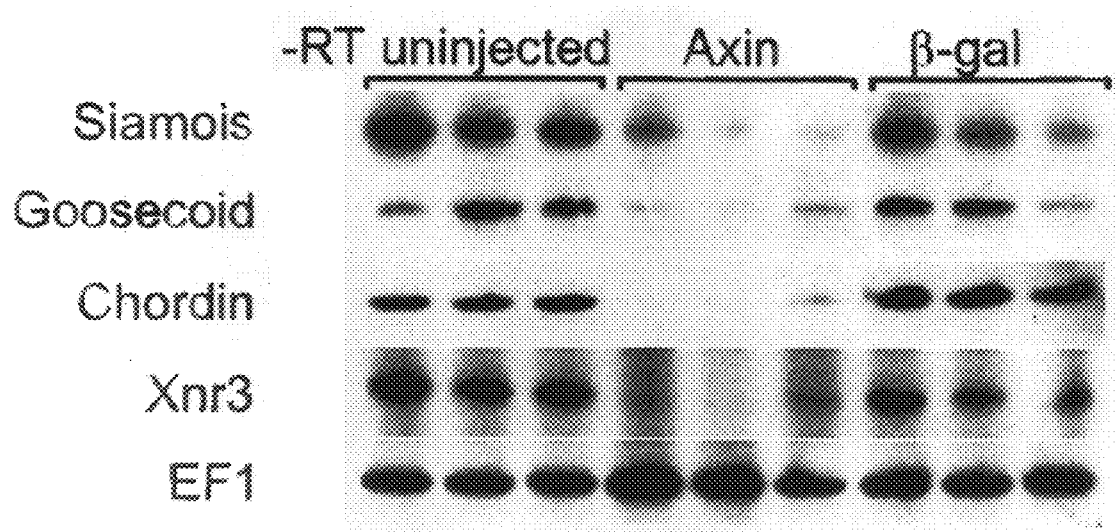
Figure 4C:
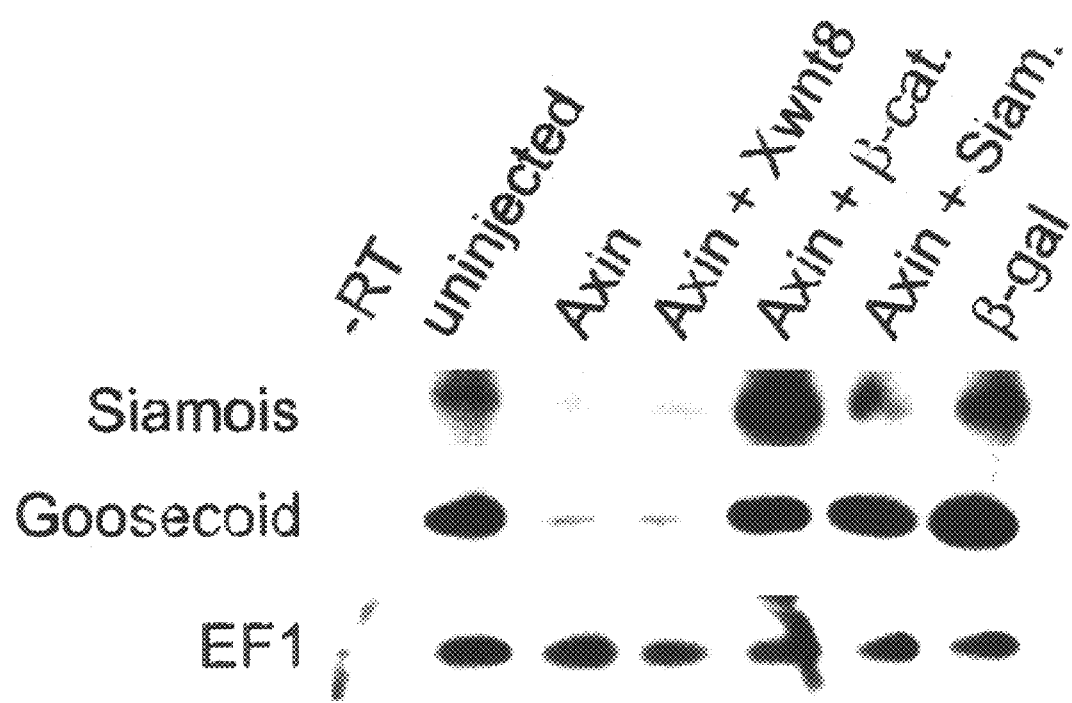

FIGS. 4A–4C. Dorsal injection of Axin mRNA ventralizes Xenopus embryos.

4A. Ventralization by dorsal injection of Axin, and rescue by β-catenin or Siamois but not Xwnt8. 2 ng of Axin mRNA, either alone or together with the other mRNA indicated, was injected into each of two dorsal blastomeres at the 4-cell stage. Embryos were evaluated at the tadpole stage (Table 1), and examples are shown. The amount of Xwnt8 (20 pg), β-catenin (300 pg) or Siamois (100 pg) mRNA used was the minimal amount required to obtain full axis induction when each was injected alone in one ventral blastomere (see FIGS. 5A & 5B). Scale bar, 1 mm.

4B. Dorsal injection of Axin reduces expression of dorsal markers Siamois, Goosecoid, Chordin, and Xnr3, but not the ubiquitously expressed elongation factor EF1. Each column shows the RT-PCR analysis of a pool of uninjected embryos or embryos injected at the 4-cell stage with Axin or control β-gal mRNA (2 ng), and grown to early gastrulae. -RT, control experiments in which RNA from uninjected embryos was processed without reverse transcriptase.

4C. Dorsal co-injection of β-catenin with Axin restores expression of Siamois and Goosecoid, and co-injection of Siamois restores Goosecoid expression, while co-injection of Xwnt8 has no effect. Note that the injected Siamois (not detected with the primers used in this assay) does not induce expression of endogenous Siamois.

Figure 5A:
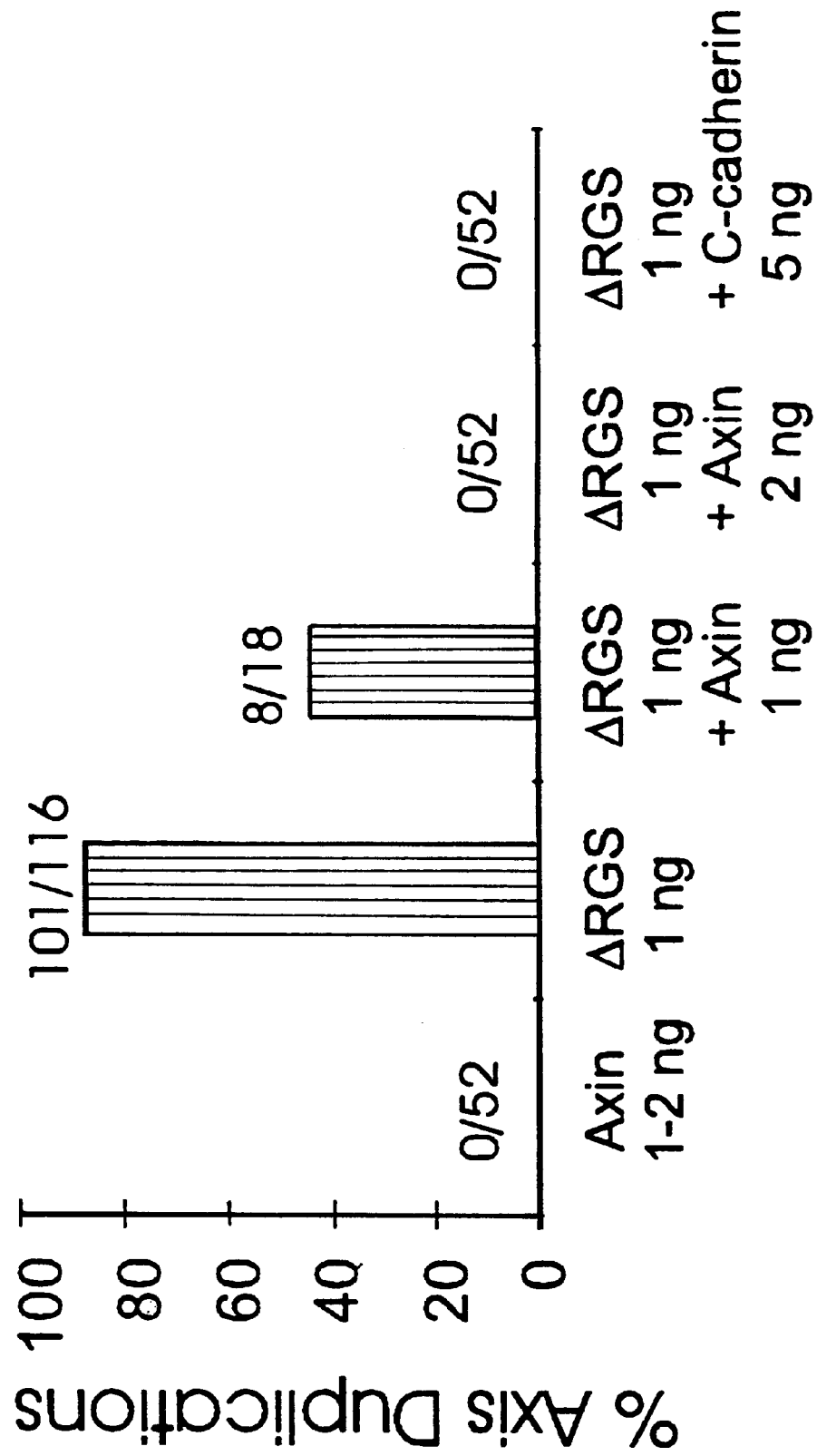
Figure 5B:
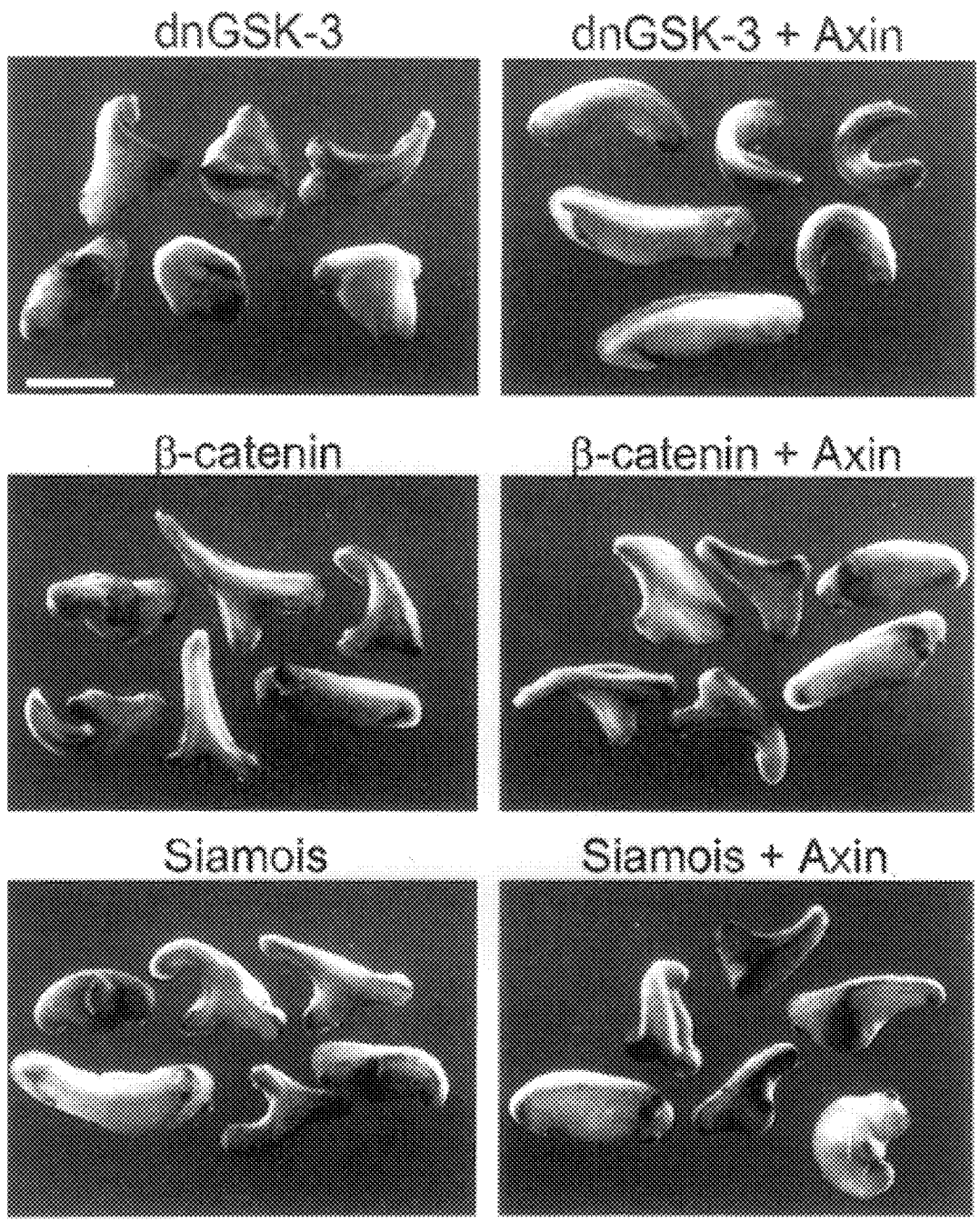
Figure 5C:
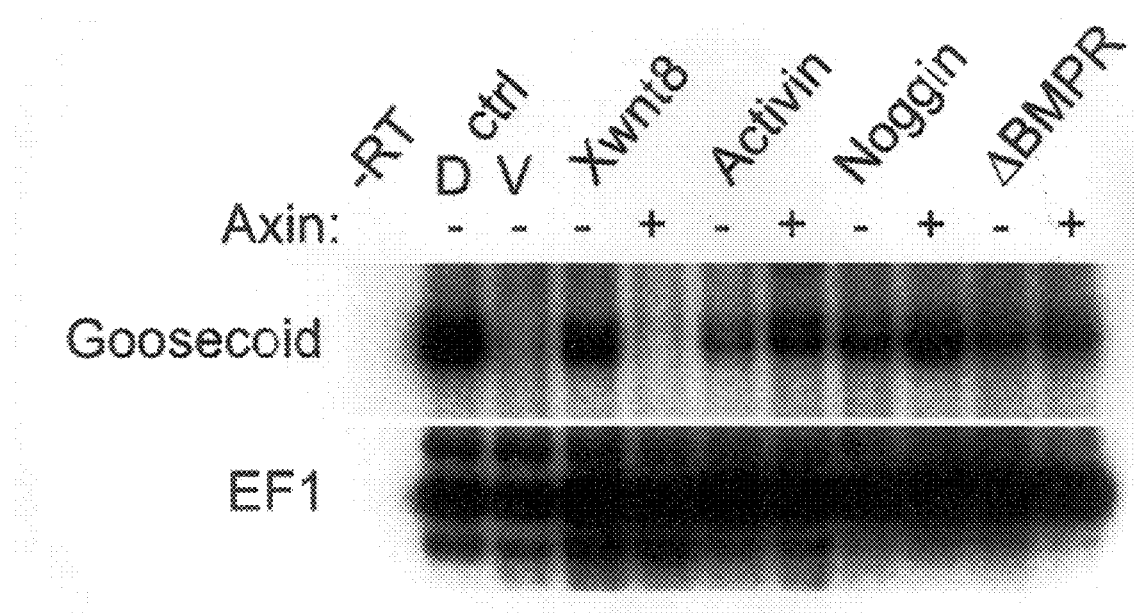

FIGS. 5A–5C. Ability of Axin to block ectopic axis formation.

5A. Ventral co-injection of Axin mRNA inhibits ectopic axis formation by upstream components of the Wnt pathway (Xwnt8, Xdsh and dnGSK-3), but not by β-catenin or Siamois, nor by Activin, Noggin or ΔBMPR. mRNA encoding the indicated dorsalizing factor was injected subequatorially in one ventral blastomere at the 4–8 cell stage, with or without 1 ng Axin, and embryos were examined for axial duplications at the late neurula—tailbud stage. The fraction of embryos with duplicated axes is indicated above each bar. mRNAs were injected in the minimal amounts needed to induce ectopic axes at high frequency: 10–20 pg Xwnt8, 1.5 ng Xdsh, 2 ng dnGSK-3, 300 pg β-catenin, 100 pg Siamois, 7.5 pg Activin, 200 pg noggin, or 1 ng ΔBMPR (Fagotto et al., 1997). Activin-induced secondary axes were generally very incomplete. Higher amounts of Activin mRNA lead to uninterpretable phenotypes.

5B. Examples of injected embryos. Scale bar, 2 mm.

5C. Co-injection of Axin mRNA inhibits induction of the dorsal marker Goosecoid by Xwnt8, but not by Activin, Noggin, or ΔBMPR. Ectopic expression of Goosecoid in the ventral half of early gastrulae (stage 10½) was analyzed by RT-PCR. Dorsal (D) and ventral (V) halves of uninjected embryos served as positive and negative controls (ctrl) for normal expression of Goosecoid.

FIGS. 6A–6G. Axis duplications in Xenopus embryos injected ventrally with ΔRGS, and in mouse embryos homozygous for the loss-of-function Axin$^{Tg1}$ allele.

6A & 6B. Xenopus embryos with axis duplications caused by injection of 2 ng ΔRGS in one ventral blastomere (6A) or 1 ng ΔRGS in two ventral blastomeres (6B). The embryo in 6B is also strongly dorsalized. Scale bars, 0.5 mm.

6C. Frequency of axis duplications in embryos injected with Axin, ΔRGS, or ΔRGS together with Axin or C-cadherin.

6D. Ectopic expression of dorsal markers in embryos injected ventrally with ΔRGS. Each column shows the RT-PCR analysis of the dorsal (D) or ventral (V) halves of a pool of embryos. In uninjected embryos, Siamois, Goosecoid, Chordin, and Xnr3 are expressed dorsally. Ventral injection of ΔRGS, but not Axin, induces ectopic expression of the four dorsal markers.

6E–6G. Lateral view of a normal E7.5 mouse embryo (e6E) and two E8.5 Axin$^{Tg1/Tg1}$ embryos with axial duplications (6F and 6G), visualized by in situ hybridization to HNF-3β, a marker of anterior axial mesoderm (Sasaki and Hogan, 1994). White arrows, primary axes; black arrowheads, ectopic axes. Scale bars, 0.2 mm.

Figure 7:
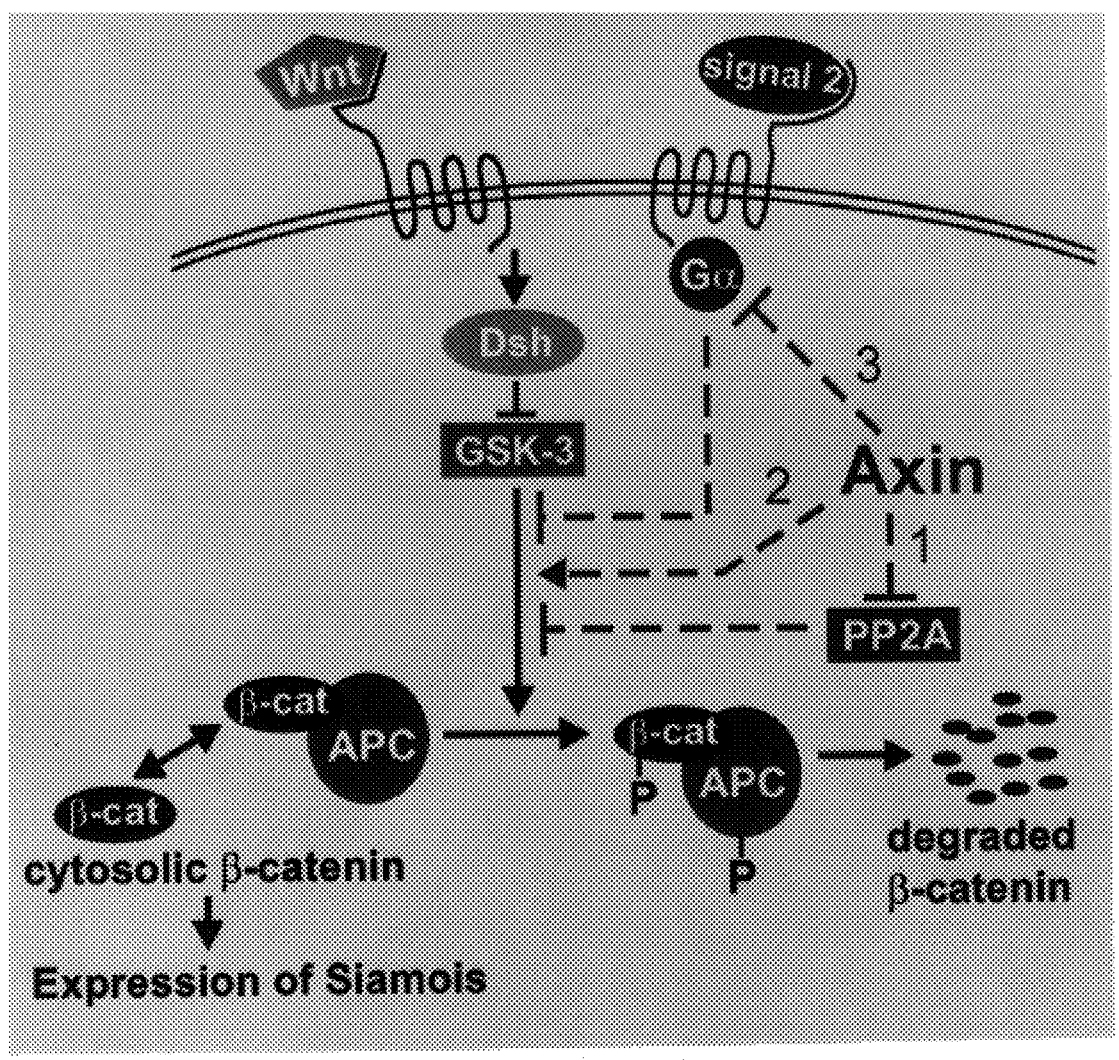

FIG. 7. Model for the inhibitory effect of Axin on Wnt signal transduction. Established components of the Wnt pathway in the Nieuwkoop Center are indicated by blue symbols and solid black arrows, and positions where Axin might inhibit the pathway are indicated by red symbols and dashed arrows. GSK-3 promotes the degradation of β-catenin, while Wnt signals inhibit GSK-3 (via Dsh) and lead to accumulation of cytosolic β-catenin and expression of Siamois. Axin blocks the stimulation of this pathway by Wnt, Dsh or dominant-negative GSK-3, but not by overexpression of β-catenin or Siamois. Three alternative hypotheses are illustrated: (1) Axin might inhibit a protein phosphatase (PP2A) that may otherwise dephosphorylate substrates of GSK-3; (2) Axin might stimulate the activity of GSK-3 through an unknown mechanism; (3) Axin might inhibit, via its RGS domain, the transmission of a second signal (signal 2) involving a G-protein-coupled receptor, which would otherwise stimulate the Wnt pathway downstream of GSK-3. See text for further details.

FIG. 8. Amino acid sequence of murine Axin (Sequence I.D. No. 1).

FIGS. 9A–9B. Nucleic acid sequence of murine Axin (Sequence I.D. No. 2).

FIGS. 10A–10B. Nucleic acid sequence of human Axin (Sequence I.D. No. 3).

FIG. 11. Amino acid sequence of human Axin. (Sequence I.D. No. 4).

DETAILED DESCRIPTION

Throughout this application, references to specific nucleotides are to nucleotides present on the coding strand of the nucleic acid. The following standard abbreviations are used throughout the specification to indicate specific nucleotides:

C=cytosine

A=adenosine

T=thymidine
G=guanosine

A "gene" means a nucleic acid molecule, the sequence of which includes all the information required for the normal regulated production of a particular protein, including the structural coding sequence, promoters and enhancers.

The nucleic acids or oligonucleotides of the subject invention also include nucleic acids or oligonucleotides coding for polypeptide analogs, fragments or derivatives which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These nucleic acids or oligonucleotides include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The nucleic acids and oligonucleotides described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

This invention provides for an isolated nucleic acid which encodes Axin. This isolated nucleic acid may be DNA or RNA, specifically cDNA or genomic DNA. This isolated nucleic acid also encodes mutant Axin or the wildtype protein.

Specifically, the isolated nucleic acid encodes a mouse wildtype Axin. This isolated nucleic acid may have the sequence designated Seq. I.D. No.: 2. Also, the isolated nucleic acid may have substantially the same amino acid sequence as the sequence designated Seq. I.D. No.: 1.

The isolated nucleic acid may also encode a human Axin having substantially the same amino acid sequence as the sequence designated Seq. I.D. No.: 4. Specifically the isolated nucleic acid has the sequence designated Seq. I.D. No.: 3.

This isolated nucleic acid may also encode a polypeptide comprising the amino acid sequence of Axin.

As used in this application, "Axin" means and includes any polypeptide having Axin activity, e.g. negative regulation of the Wnt signalling pathway, and having an amino acid sequence homologous to the amino acid sequence of mouse Axin (the sequence of which is set forth in Sequence I.D.

No.: 1). Thus, this term includes any such polypeptide whether naturally occurring and obtained by purification from natural sources or non-naturally occuring and obtained synthetically, e.g. by recombinant DNA procedures. Moreover, the term includes any such polypeptide whether its sequence is substantially the same as, or identical to the sequence of any mammalian homolog of the human polypeptide, e.g. murine, bovine, porcine, etc. homologs. Additionally, the term includes mutants or other variants of any of the foregoing which retain at least some of the enzymatic activity of nonmutants or nonvariants.

The invention also encompasses DNAs and cDNAs which encode amino acid sequences which differ from Axin, but which do not produce phenotypic changes.

However, a mutant Axin will not exhibit the same phenotype as the wildtype Axin. For example, a cell containing a mutant version of the axin gene will express a protein unable to negatively regulate the Wnt signalling pathway.

The nucleic acid of the subject invention also include nucleic acids that encode for polypeptide analogs, fragments or derivatives which differ from naturally-occurring forms in terms of the identity or location of one or more amino acid residues (including deletion analogs containin less than all of the residues specified for the protein, substitution analogs wherein one or more residues specified are replaced by other residues and addition analogs wherein one or more amino acid residues is added to a terminal or medial portion of the polypeptides) and which share some or all properties of the naturally-occuring forms.

The polypeptide of the subject invention also includes analogs, fragments or derivatives which differ from naturally-occurring forms, but Axin activity.

This invention also provides a vector comprising an isolated nucleic acid encoding Axin. The isolated nucleic acid of the vectors is operatively linked to a promoter of RNA transcription which maybe, or is identical to, a bacterial, yeast, insect or mammalian promoter. The vector may be a plasmid, cosmid, yeast artificial chromosome (YAC), bacteriophage or eukaryotic viral DNA. Specifically, this invention provides two cosmids designated Genbank Accession No. Z69667 and Z81450, respectively.

Further other numerous vector backbones known in the art as useful for expressing proteins may be employed. Such vectors include but are not limited to: adenovirus, simian virus 40 (SV40), cytomegalovirus (CMV), mouse mammary tumor virus (MMTV), Moloney murine leukemia virus, murine sarcoma virus, and *Rous sarcoma* virus, DNA delivery systems, i.e liposomes, and expression plasmid delivery systems.

This invention also provides a vector system for the production of a polypeptide which comprises the vector in a suitable host. Suitable host includes a cell which includes, but is not limited, prokaryotic or eukaryotic cells, e.g. bacterial cells (including gram positive cells), yeast cells, fungal cells, insect cells and animal cells.

Suitable animal cells include, but are not limited to, HeLa cells, Cos cells, CV1 cells and various primary mammalian cells. Numerous mammalian cells may be used as hosts, including, but not limited to, the mouse fibroblast cell NIH 3T3, CHO cells, Ltk$^-$ cells, etc. Expression plasmids such as that described supra may be used to transfect mammalian cells by methods well known in the art such as calcium phosphate precipitation, electroporation.

This invention also provides a method for producing a polypeptide (e.g. Axin) which comprises growing a host vector system under suitable conditions permitting production of the polypeptide and recovering the polypeptide so produced. Methods of recovering polypeptides produced in such host vector systems are well-known in the art and typically include steps involving cell lysis, solubilization and chromatography.

This invention also providies a method of obtaining a polypeptide in purified form which comprises: (a) introducing a vector, as described above, into a suitable host cell; (b) culturing the resulting cell so as to produce the polypeptide; (c) recovering the polypeptide produced in step (b); and (d) purifying the polypeptide so recovered. As discussed above the vector may include a plasmid, cosmid, yeast artificial chromosome, bacteriophage or eukaryotic viral DNA. Also, the host cell may be a bacterial cell (including gram positive cells), yeast cell, fungal cell, insect cell or animal cell. Suitable animals cells include, but are not limited to HeLa cells, Cos Cells, CV1 cells and various primary mammalian cells. Culturing methods useful for permitting transformed or transfected host cells to produce polypeptides are well known in the art as are the methods for recovering polypeptides from such cells and for purifying them.

Using the aforementioned method, this invention also provides a purified wildtype Axin and a purified mutant Axin. Further, this invention also provides a polypeptide comprising the amino acid sequence of Axin, including, but limited to, fusion proteins having part of their amino acid sequence the amino acid sequence of Axin.

This invention also provides an oligonucleotide of at least 15 nucleotides capable of specifically hybridizing with a unique sequence of nucleotides present within a nucleic acid which encodes a wildtype Axin without hybridizing to a nucleic acid which encodes a mutant Axin. Further, this invention also provides an oligonucleotide of at least 15 nucleotides capable of specifically hybridizing with a unique sequence of nucleotides present within the nucleic acid which encodes a mutant Axin without hybridizing to a nucleic acid which encodes a wildtype Axin. These oligonucleotides may be DNA or RNA. Such oligonucleotides may be used in accordance with well known standard methods for known purposes, for example, to detect the presence in a sample of DNA which will hybridize thereto.

As used herein, "capable of specifically hybridizing" means wherein the oligonucleotide will selectively bind to only sequences which are unique to either nucleic acids encoding wildtype or mutant Axin.

The oligonucleotides include, but are not limited to, oligonucleotides that hybridize to mRNA encoding Axin so as to prevent translation of the protein.

This invention also provides a nucleic acid having a sequence complementary to the sequence of the isolated nucleic acid which encodes Axin. Furthermore, this application also provides an antisense molecule of capable of specifically hybridizing with the isolated nucleic acid encoding mutant Axin.

This invention provides a method for determining whether a subject carries a mutation in the axin gene which comprises (a) obtaining an appropriate nucleic acid sample from the subject; and (b) determining whether the nucleic acid sample from step (a) is, or is derived from, a nucleic acid which encodes mutant Axin so as to thereby determine whether a subject carries a mutation in the axin gene.

In a specific example of the above-described method, the nucleic acid sample in step (a) is mRNA corresponding to the transcript of DNA encoding a mutant Axin, and wherein the determining of step (b) comprises (i) contacting the mRNA with the oligonucleotide capable of detecting only nucleic acid corresponding to mutant Axin under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant Axin.

As used herein "corresponding to mutant Axin" means capable of specifically hybridizing with a unique sequence of nucleotides present within the nucleic acid which encodes a mutant Axin without hybridizing to a nucleic acid which encodes a wildtype Axin.

In another specific embodiment, the determining of step (b) comprises (i) contacting the nucleic acid sample of step (a), and the isolated nucleic acid encoding Axin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant Axin.

In another embodiment, the determining of step (b) comprises: (i) sequencing the nucleic acid sample of step (a); and (ii) comparing the nucleic acid sequence of step (i) with the isolated nucleic acid encoding wildtype Axin, so as to thereby determine whether the nucleic acid sample is, or is derived from, a nucleic acid which encodes mutant Axin.

One can also practice the invention, wherein the determining of step (b) comprises: (i) amplifying the nucleic acid present in the sample of step (a); and (ii) detecting the presence of the mutant Axin in the resulting amplified nucleic acid.

In order to facilitate identification of the nucleic acid from step (a) the isolated nucleic acid or the oligonucleotide is labeled with a detectable marker. The detectable marker may be a radioactive isotope, a fluorophor or an enzyme. In additions, the nucleic acid sample may be bound to a solid matrix before performing step (i).

The invention described above may have sample which is blood, tissues or sera.

This invention also provides a method for determining whether a subject has a predisposition for cancer which comprises (a) obtaining an appropriate nucleic acid sample from the subject; and (b) determining whether the nucleic acid sample from step (a) is, or is derived from, a nucleic acid which encodes mutant Axin so as to thereby determine whether a subject has a predisposition for cancer.

In a specific example of the above-described method, the nucleic acid sample in step (a) is mRNA corresponding to the transcript of DNA encoding a mutant Axin, and wherein the determining of step (b) comprises (i) contacting the mRNA with the oligonucleotide capable of detecting only nucleic acid corresponding to mutant Axin under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant Axin.

As used herein "corresponding to mutant Axin" means capable of specifically hybridizing with a unique sequence of nucleotides present within the nucleic acid which encodes a mutant Axin without hybridizing to a nucleic acid which encodes a wildtype Axin.

In another specific embodiment, the determining of step (b) comprises (i) contacting the nucleic acid sample of step (a), and the isolated nucleic acid encoding Axin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant Axin.

In another embodiment, the determining of step (b) comprises: (i) sequencing the nucleic acid sample of step (a); and (ii) comparing the nucleic acid sequence of step (i) with the isolated nucleic acid encoding wildtype Axin, so as to thereby determine whether the nucleic acid sample is, or is derived from, a nucleic acid which encodes mutant Axin.

One can also practice the invention, wherein the determining of step (b) comprises: (i) amplifying the nucleic acid present in the sample of step (a); and (ii) detecting the presence of the mutant Axin in the resulting amplified nucleic acid.

In order to facilitate identification of the nucleic acid from step (a) the isolated nucleic acid or the oligonucleotide is labeled with a detectable marker. The detectable marker may be a radioactive isotope, a fluorophor or an enzyme. In additions, the nucleic acid sample may be bound to a solid matrix before performing step (i)

This invention also provides where the sample includes, but is not limited to, blood, tissues or sera.

As used herein "cancer" includes, but is not limited to, brain, thyroid, breast, colorectal, gastrointestinal, esophageal carcinomas or melanomas.

This invention also provides a method for treating a subject who has a predisposition to cancer which comprises introducing the isolated nucleic acid encoding wildtype Axin into the subject under conditions such that the nucleic acid expresses wildtype Axin, so as to thereby treat the subject.

This invention also provides a method for treating a subject who has a predisposition to cancer which comprises an effective amount of the wildtype human homolog of Axin and a pharmaceutically acceptable carrier, so as to thereby treat the subject who is susceptible to cancer.

This invention also provides a method for determining whether a subject has cancer, which comprises (a) obtaining an appropriate nucleic acid sample from the subject; and (b) determining whether the nucleic acid sample from step (a) is, or is derived from, a nucleic acid which encodes mutant Axin so as to thereby determine whether a subject has cancer.

In a specific example of the above-described method, the nucleic acid sample in step (a) is mRNA corresponding to the transcript of DNA encoding a mutant Axin, and wherein the determining of step (b) comprises (i) contacting the mRNA with the oligonucleotide capable of detecting only nucleic acid corresponding to mutant Axin under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant Axin.

In another specific embodiment, the determining of step (b) comprises (i) contacting the nucleic acid sample of step (a), and the isolated nucleic acid encoding Axin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant Axin.

In another embodiment, the determining of step (b) comprises: (i) sequencing the nucleic acid sample of step (a); and (ii) comparing the nucleic acid sequence of step (i) with the isolated nucleic acid encoding wildtype Axin, so as to thereby determine whether the nucleic acid sample is, or is derived from, a nucleic acid which encodes mutant Axin.

One can also practice the invention, wherein the determining of step (b) comprises: (i) amplifying the nucleic acid present in the sample of step (a); and (ii) detecting the presence of the mutant Axin in the resulting amplified nucleic acid.

In order to facilitate identification of the nucleic acid from step (a) the isolated nucleic acid or the oligonucleotide is labeled with a detectable marker. The detectable marker may be a radioactive isotope, a fluorophor or an enzyme. In additions, the nucleic acid sample may be bound to a solid matrix before performing step (i).

This invention also provides a method for detecting a mutation in cancerous cells of the subject which comprises: (a) obtaining an appropriate nucleic acid sample from the subject; and (b) determining whether the nucleic acid sample from step (a) is, or is derived from, a nucleic acid which encodes mutant Axin so as to thereby detect a mutation in the cancerous cells of the subject.

In a specific example of the above-described method, the nucleic acid sample in step (a) is mRNA corresponding to the transcript of DNA encoding a mutant Axin, and wherein the determining of step (b) comprises (i) contacting the mRNA with the oligonucleotide capable of detecting only nucleic acid corresponding to mutant Axin under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant Axin.

In another specific embodiment, the determining of step (b) comprises (i) contacting the nucleic acid sample of step (a), and the isolated nucleic acid encoding Axin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant Axin.

In another embodiment, the determining of step (b) comprises: (i) sequencing the nucleic acid sample of step (a); and (ii) comparing the nucleic acid sequence of step (i) with the isolated nucleic acid encoding wildtype Axin, so as to thereby determine whether the nucleic acid sample is, or is derived from, a nucleic acid which encodes mutant Axin.

One can also practice the invention, wherein the determining of step (b) comprises: (i) amplifying the nucleic acid present in the sample of step (a); and (ii) detecting the presence of the mutant Axin in the resulting amplified nucleic acid.

In order to facilitate identification of the nucleic acid from step (a) the isolated nucleic acid or the oligonucleotide is labeled with a detectable marker. The detectable marker may be a radioactive isotope, a fluorophor or an enzyme. In additions, the nucleic acid sample may be bound to a solid matrix before performing step (i).

This invention also provides a method of suppressing cells unable to regulate themselves which comprises introducing the isolated nucleic acid encoding wildtype Axin into the cells.

In a specific example of the above-described method, the nucleic acid sample in step (a) is mRNA corresponding to the transcript of DNA encoding a mutant Axin, and wherein the determining of step (b) comprises (i) contacting the mRNA with the oligonucleotide capable of detecting only nucleic acid corresponding to mutant Axin under conditions permitting binding of the mRNA to the oligonucleotide so as to form a complex; (ii) isolating the complex so formed; and (iii) identifying the mRNA in the isolated complex so as to thereby determine whether the mRNA is, or is derived from, a nucleic acid which encodes mutant Axin.

In another specific embodiment, the determining of step (b) comprises (i) contacting the nucleic acid sample of step (a), and the isolated nucleic acid encoding Axin with restriction enzymes under conditions permitting the digestion of the nucleic acid sample, and the isolated nucleic acid into distinct, distinguishable pieces of nucleic acid, (ii) isolating the pieces of nucleic acid; and (iii) comparing the pieces of nucleic acid derived from the nucleic acid sample with the pieces of nucleic acid derived from the isolated nucleic acid so as to thereby determine whether the nucleic acid sample is, or is derived from, a nucleic acid which encodes mutant Axin.

In another embodiment, the determining of step (b) comprises: (i) sequencing the nucleic acid sample of step (a); and (ii) comparing the nucleic acid sequence of step (i) with the isolated nucleic acid encoding wildtype Axin, so as to thereby determine whether the nucleic acid sample is, or is derived from, a nucleic acid which encodes mutant Axin.

One can also practice the invention, wherein the determining of step (b) comprises: (i) amplifying the nucleic acid present in the sample of step (a); and (ii) detecting the presence of the mutant Axin in the resulting amplified nucleic acid.

In order to facilitate identification of the nucleic acid from step (a) the isolated nucleic acid or the oligonucleotide is labeled with a detectable marker. The detectable marker may be a radioactive isotope, a fluorophor or an enzyme. In additions, the nucleic acid sample may be bound to a solid matrix before performing step (i).

Also, the cells may be unable to regulate themselves because of a mutation in the axin gene or a mutation in the adenomatous polyposis coli gene.

This invention also provides a method of suppressing cells unable to regulate themselves which comprises introducing wildtype Axin into the cells in an amount effective enough to suppress the cells.

This invention also provides a method of treating a subject who has cancer which comprises introducing the isolated nucleic acid encoding wildtype Axin, into the subject so as to thereby treat the cancer.

One well-known means of introducing the isolated nucleic acid, comprises: (a) recovering cancerous cells from the subject; (b)introducing the isolated nucleic acid encoding the wildtype Axin into the cells; and (c)reintroducing the cells of step (b) into the subject so as to treat the subject who has cancer.

This invention further provides a method for identifying a chemical compound which is capable of suppressing cells unable to regulate themselves in a subject which comprises: (a) contacting mutant Axin with the chemical compound under conditions permitting binding between the mutant Axin and the chemical compound; (b) detecting specific binding of the chemical compound to the mutant Axin; and (c) determining whether the chemical compound inhibits the mutant Axin so as to identify a chemical compound which is capable of suppressing cells unable to regulate themselves.

This method is applicable when the cells are cancerous. For example, when cancerous cells are derived from the abdominal cavity, brain, breast, skin, colon, rectum, esophagus, stomach, thyroid or intestine.

This invention provides pharmaceutical compositions comprising the chemical compound identified by the above-described method of in an amount effective to inhibit cancer and a pharmaceutically effective carrier.

Further this invention also includes a pharmaceutical compositions includes an antisense molecule to an isolated nucleic acid which encodes mutant Axin in an amount effective to treat cancer and a pharmaceutically effective carrier.

This invention also includes a pharmaceutical composition comprising the purified wildtype Axin in an amount effective to treat cancer and a pharmaceutically effective carrier.

One can treat a subject who has cancer by administrating an effective amount of the above-described pharmaceutical composition to the subject who has cancer.

One can administer the above-described compositions by topical, oral, aerosol, subcutaneous administration, infusion, intralesional, intramuscular, intraperitoneal, intratumoral, intratracheal, intravenous injection, or liposome-mediate delivery.

Methods of administration of pharmaceutical compositions are well-known in the art.

This invention also includes transgenic, nonhuman mammal containing the isolated nucleic encoding Axin, specifically, an isolated nucleic acid encoding mutant Axin.

This invention is illustrated in the Experimental Details section which follows. These sections are set forth to aid in an understanding of the invention but are not intended to, and should not be construed to, limit in any way the invention as set forth in the claims which follow thereafter.

First Section

Experimental Procedures

1. Isolation and characterization of mouse Axin cDNA and genomic clones

Primers for mAxin are named for the position of their 5' terminus in the CDNA (+numbers) or in upstream genomic DNA (− numbers). F indicates a forward and R a reverse primer. Sequences are listed 5' to 3'. A 315 bp NotI-StuI genomic probe at the left of the transgene insert (Perry et al., 1995) was used to screen an E8.5 mouse embryo cDNA library, yielding one clone (N7) that was partially colinear with the probe. Using a fragment of N7, 12 more clones were isolated from a WEHI-3 cDNA library (Stratagene). Additional Axin cDNA clones were obtained from various libraries using probes from clone N7, but none extended as far 5' as N7. 5' RACE was performed using kidney cDNA, AP1 primer (Advantage cDNA PCR kit, Clonetech) and mAxin primer +98R (caccagccctctctggaacc) (SEQ ID NO: 9). The RACE product extending farthest 5' was colinear with clone N7 and contained 4 more bp at the 5' end. To estimate the ratio of forms 1 and 2 mRNA, total RNA was reverse transcribed using oligo-dT primer, and the cDNA was amplified using +2289F (gagggagagaaggagatcag) (Sequence I.D. No. 5) and +2744R (gtagctccccttcttggttag) (Sequence. I.D. No. 6).

Intron/exon structure was determined by restriction mapping and sequencing of genomic subclones and products of long template PCR using primers in adjacent exons. Previously isolated clones (Perry et al., 1995) included exons 1–3, and clones including exons 6–10 were isolated from a strain 129 library. The remaining region was isolated by long template PCR (Boehringer Mannheim) using primers at different positions in the cDNA.

2. Isolation of human and chick Axin cDNA clones

Database searches revealed ESTs (T07178, R75687, T30966, T32063, T15895 and T72547) representing the 3' region of a human Axin homolog (hAxin). Additional clones were isolated by 5' and 3' RACE using human placenta RNA (Clonetech Marathon RACE kit). A stage 12–15 chick embryo cDNA library (a gift of Dr. D. Wilkinson) was screened with a mAxin probe and four clones containing the same insert in both orientations were isolated. The 3131 bp cAxin cDNA sequence contains a polyadenylation signal near the 3' end, but is shorter than the cAxin mRNA (~3.6 kb), even after accounting for a poly(A) tail, and thus may lack part of the 5' UTR.

3. Sequence analysis

Database searches were conducted using BLAST, and sequence alignments using ClustalW and BOXSHADE. Other RGS sequences are: Q08116 (hRGS1), P41220 (hRGS2), U27768 (hRGS3), U27768 (rRGS4), D31257 and R35272 (hRGS5), U32328 (hRGS7), H87415 (hRGS10), X91809 (hGAIP).

4. Northern blot and in situ hybridization

20 μg of total RNA from embryos, adult tissues or ES cells was run on a formaldehyde-agarose (1.2%) gel, blotted to Genescreen plus (NEN-Dupont), and hybridized with a $^{32}$P-DNA probe containing the entire mAxin cDNA sequence, as described (Perry et al., 1995). For in situ hybridization (Wilkinson, 1992), an anti-sense probe was produced by T7 transcription of a HindIII-SacI fragment of mAxin cDNA (bp 765–1065, within exon 2) in pBluescript. A sense probe did not produce a significant signal. The HNF-3β probe was produced from clone c21 (Sasaki and Hogan, 1993).

5. Constructs for Xenopus injection

Axin cDNAs were cloned into the XhoI site of pCS2+MT (Rupp et al., 1994). The experiments shown employed vector MTPA2, which includes Axin form 2 (bp 37 to 3310) and encodes aa 13 to the normal C-terminus. Translation initiates in the N-terminal Myc tag. Three other Axin vectors (MTPA1, MTFU1 and MTFU2) were similarly active at ventralization: MTPA1 was identical to MTPA2 except it was derived from a form 1 cDNA. MTFU1 and MTFU2 were identical to MTPA1 and MTPA2, except they contained a longer 3' UTR (bp 3311–3731). ΔRGS was derived from MTFU1 by deleting cDNA bp 754 –1053. Siamois was cloned in pCS2+MT (Fagotto et al., 1997) and β-catenin (C-terminally HA-tagged) in pSP36 (Funayama et al., 1995). Other expression vectors were: Xwnt8 and Noggin (gift of Dr. R. Harland), Activin (Dr. D. Melton), ΔBMPR (Dr. A. Susuki), dnGSK-3 (GSK-3-K>R, Dr. D. Kimelman) and Xdsh (Dr. U. Rothbacher). GSK-3-K>R is a mutant of Xenopus GSK-3β without kinase activity (Pierce and Kimelman, 1995). ΔBMPR is a truncated BMPR lacking the kinase domain (Suzuki et al., 1994).

6. Xenopus injections and analysis of phenotypes mRNAs were synthesized and injected as previously described (Fagotto et al., 1996; 1997). For RT-PCR, mRNA was extracted from whole early gastrulae (stage 10½) or dissected dorsal and ventral halves, and specific mRNAs were detected as described (Fagotto et al., 1997). Siamois primers were: 5' ttgggagacagacatga (corresponds to part of the 5' UTR, present in the endogenous mRNA but not the injected synthetic Siamois mRNA) (Sequence I.D. No. 7) and 3': tcctgttgactgcagact (Sequence I.D. No. 8). Other primers were as described (Fagotto et al., 1997). For immunofluorescence, Myc-tagged Axin was detected in frozen sections of early gastrulae using anti-Myc antibody 9E10.2, as described (Fagotto et al., 1996; Fagotto and Gumbiner, 1994).

Results

1. Identification of the Axin gene

A genomic probe from the Axin$^{Tg1}$ transgene insertion locus detected a 3.9 kb RNA in wild type embryonic stem (ES) cells but not in Axin$^{Tg1/Tg1}$ ES cells, representing a strong candidate for the Axin mRNA (Perry et al., 1995). To isolate cDNA clones, a probe located within a CpG island upstream from the transgene insertion site (FIG. 1) was used to screen a mouse embryo library. One cDNA clone contained a region identical in sequence with the genomic probe, confirming that it was encoded at the Axin locus, and this clone was used to isolate additional overlapping cDNA clones. The composite cDNA sequence was 3623 bp long, excluding the poly(A) tail. All the cDNA clones were co-linear in their regions of overlap, except for a 108 bp sequence present in a fraction of clones following bp 2579, representing an alternative splicing product (FIG. 1). Transcripts lacking this 108 bp segment were termed "form 1" and those containing it "form 2".

2. Genomic organization of Axin

Using Axin cDNA probes, a series of overlapping clones was isolated from a WT mouse genomic library, and the locations of exons and introns were determined (see Experimental Procedures). As illustrated in FIG. 1, 10 exons were identified, spanning ~56 Kb. The extra 108 bp segment in form 2 mRNA results from the use of an alternative 5' splice site following exon 8, and is designated exon 8A. The longest cDNA clones representing the 3.9 kb mRNA appeared to be missing 25–75 nt from the 5' end, based on RNase H and S1 nuclease mapping studies. Difficulties in cloning these 5' terminal sequences may be a consequence of the very high GC content of the CpG island surrounding the apparent promoter region (FIG. 1). Based on Southern blot hybridization to genomic DNA, and the analysis of multiple cDNA and genomic clones, Axin appears to be a single copy gene.

In the Axin$^{Tg1}$ allele, exon 2 and parts of the two flanking introns are deleted. Exons 1 and 3 are separated by a ~600 kb transgene insertion (FIG. 1), a disruption that leads to the absence of the major WT 3.9 kb mRNA in homozygotes (FIG. 2). As described elsewhere (Vasicek et al., manuscript submitted), the Axin$^{Fu}$ allele contains an endogenous intracisternal A particle (IAP) provirus within intron 6, while Axin$^{Kb}$ contains a similar IAP element interrupting exon 7. The Axin$^{Ki}$ allele is apparently extinct.

3. Ubiquitous expression of wild type Axin mRNA.

Figure 2A:
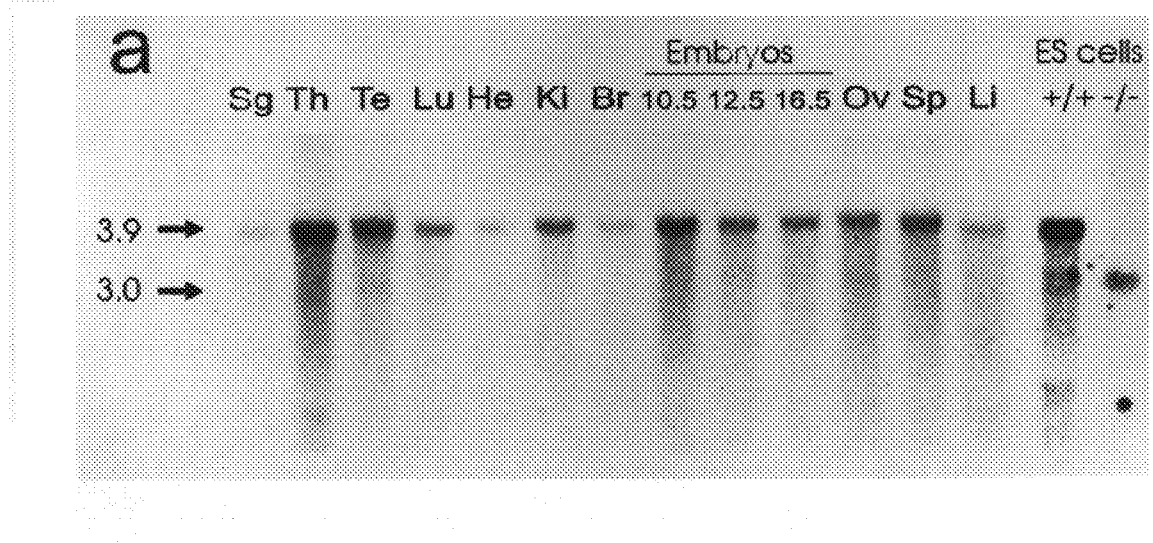
FIGS. 2A–2C. Expression of Axin MRNA in adult tissues, embryos and ES cells.

On Northern blots, a major band of ~3.9 kb was observed in all WT adult tissues examined, embryos at E10.5–E16.5, and ES cells. A 3.0 kb band was also observed at very low levels in some WT tissues and ES cells. In Axin$^{Tg1/Tg1}$ ES cells, the 3.9 kb RNA was absent, but a 3.0 kb RNA was observed (FIG. 2A). Because the 3.0 kb mRNA was observed in both WT and Axin$^{Tg1/Tg1}$ cells, and contains exons 3–10 but not 1 and 2, it is likely to be transcribed from a weak promoter downstream from the 3' end of the transgene-induced deletion. Thus, Axin$^{Tg1}$ is a loss-of-function allele with respect to the major 3.9 kb mRNA, although it may not be a null allele.

Figure 2B:
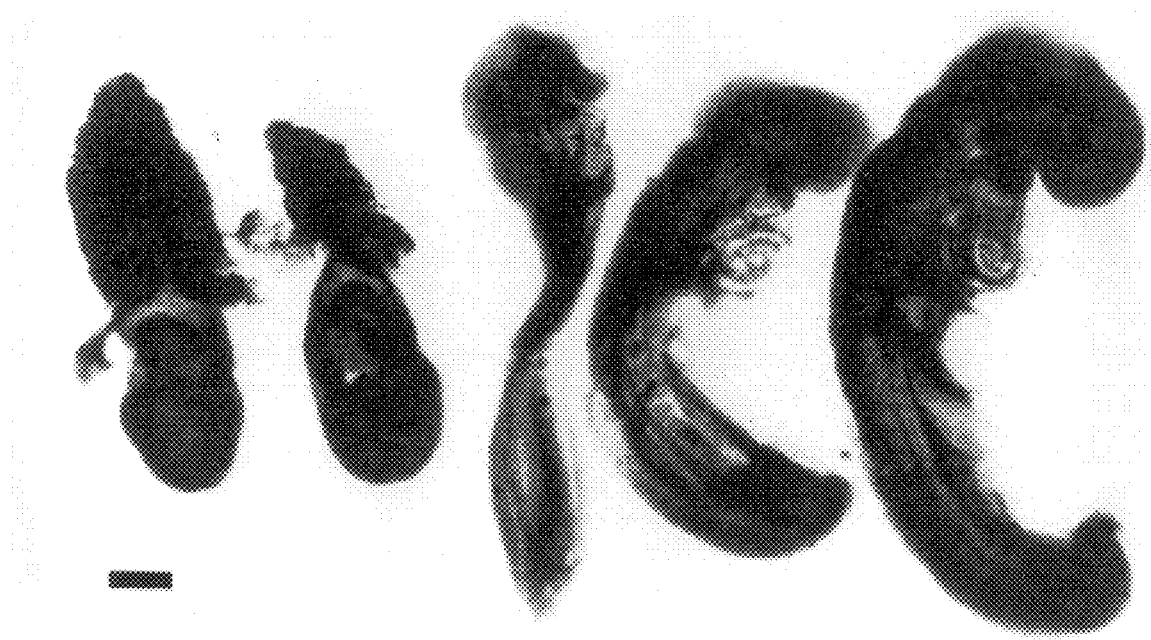
Figure 2C:
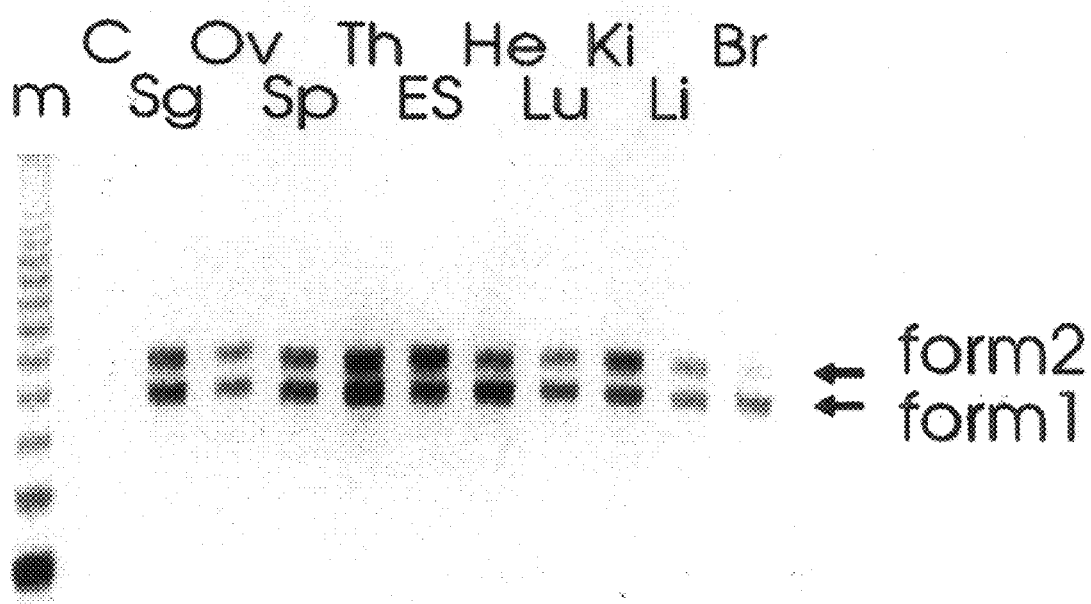

In situ hybridization with WT embryos at E7.5–E9.5 showed that Axin mRNA is uniformly distributed throughout embryonic and extraembryonic tissues of the postimplantation embryo (FIG. 2B). Axin mRNA was also detected by RT-PCR in 1-cell through blastocyst stage embryos. Form 1 and 2 mRNAs were both present in all adult tissues examined and in ES cells (FIG. 2C).

4. The predicted amino acid sequences of Axin and its human and chicken homologs The murine Axin (mAxin) cDNA sequence included an open reading frame (ORF) beginning at base 3, which could encode a protein of up to 956 (form 1) or 992 (form 2) amino acids (FIG. 3A) (SEQ ID NO: 1, 4, and 10). Homology searches identified several ESTs representing a human Axin homolog, and additional human cDNA sequences were isolated by 5' and 3' RACE (Chenchik et al., 1995). The predicted human and murine Axin amino acid (aa) sequences are 87% identical overall. In addition, a cDNA clone representing a chicken homolog was isolated, and its predicted aa sequence was 66% identical to mouse Axin (FIG. 3A) (SEQ ID NO: 1, 4, and 10). The first two AUG codons in the mAxin ORF were located at bp 375 and 391 of the cDNA, but neither was surrounded by a consensus initiation site (Kozak, 1986). To determine whether either site could serve as an initiation codon, 293T cells were transfected with Axin cDNA expression vectors including a C-terminal epitope tag. The sizes of the in vivo translation products were consistent with initiation at one of the first two AUG codons. However, because the murine and human ORFs continue to be conserved upstream of this position, it remains possible that the normal initiation site is further upstream.

The predicted aa sequence contains multiple sites for Ser/Thr phosphorylation and one for Tyr phosphorylation, suggesting that Axin may be a phosphoprotein. It also contains one (form 2) or two (form 1) sequences matching the consensus for a bipartite nuclear localization signal (NLS) (Dingwall and Laskey, 1991). However, detection of epitope-tagged Axin proteins expressed in mammalian cells or Xenopus embryos indicated a peri-membrane rather than a nuclear location for both forms. Database searches revealed two regions of homology to other known proteins. One of these, aa 213 to 338, shows 30–40% identity and 50–60% similarity to the RGS (Regulation of G-protein Signaling) domain (Dohlman and Thorners, 1997). A second potentially important region of similarity (FIG. 3c) (SEQ ID NO: 11, 12, 13, 14, 15, 16, 17, 18 and 19) is a 51 aa segment near the Axin C-terminus, which is ~40% identical and ~60% similar to a conserved sequence near the N-terminus of Drosophila Dsh and its vertebrate homologs (Klingensmith et al., 1994; Sussman et al., 1994). Both the RGS and Dsh homology regions are highly conserved among mouse, human and chick Axin homologs (FIG. 3A) (SEQ ID NO: 1, 4, and 10).

5. Injection of Axin mRNA inhibits dorsal axis formation in Xenopus embryos.

The observation that the Axin$^{Tg1}$ and Axin$^{Kb}$ alleles, which cause axial duplications in homozygous mouse embryos, are both unable to produce the major 3.9 kb mRNA suggested that one function of Axin is to negatively regulate an early step in axis formation. Because the Axin sequence is highly conserved among amniotes, mAxin might be able to function in amphibian embryos, a system highly amenable to experimental manipulation of early axial development. Therefore, in vitro synthesized mAxin mRNA (encoding aa 13-956, with an N-terminal Myc epitope tag) was injected into the dorsal, subequatorial region of 4-cell Xenopus embryos, which were scored at the tadpole stage for effects on axis formation (FIG. 4A and Table 1). Most of these embryos developed with strong axial defects ranging from loss of anterior structures to complete lack of body axis, a phenotype characteristic of completely ventralized embryos (Kao and Elinson, 1988). Control injections of β-gal mRNA had no effect. Embryos injected dorsally with Axin also showed a markedly reduced expression of the dorsal markers Siamois, Goosecoid, Chordin and Xnr3, consistent with the observed ventralizing effects (FIG. 4B). Forms 1 and 2 Axin mRNAs were equally active, and α-Myc staining showed that both proteins were similarly localized in a punctate pattern near the plasma membrane.

TABLE 1

Frequency and extent of ventralization by dorsal injection of Axin mRNA, and rescue by β-catenin or Siamois but not Xwnt8.
Both dosal blastomeres of 4-cell embryos were injected in the subequatorial region. Dorso-Anterior Index (DAI) is a measure of axial development, where 5 is normal, 0 is completely ventralized, and >5 is hyper-dorsalized (Kao and Elinson, 1988). *DAI <4 was considered significant ventralization.

| mRNAs injected | % | Average DAI | Number |
|---|---|---|---|
| β-galactosidase (2 ng, control) | 3 | 4.8 | 31 |
| Axin (2 ng) | 78 | 1.7 | 118 |
| Axin + Xwnt8 (10–20 pg) | 90 | 1.9 | 67 |
| Axin + β-catenin (300 pg) | 29 | 4.3 | 35 |
| Axin + Siamois (50–100 pg) | 2 | 5.1 | 96 |

6. Inhibition of dorsal axis formation by Axin is mediated by the Wnt signaling pathway.

The ventralizing effect of Axin could be due either to inhibition of Nieuwkoop Center activity, which requires the activation of the Wnt signaling pathway, or to perturbation of further downstream inductive processes, i.e. establishment of the Spemann organizer or BMP-dependent mesodermal patterning. To test whether Axin might exert its effects via the Wnt pathway, mRNA encoding Xwnt8, β-catenin or Siamois was co-injected with Axin mRNA into the dorsal, subequatorial region. Siamois is a homeobox gene whose expression is specifically activated by Wnt signaling, and which appears to mediate the effects of the Wnt pathway on axis formation (Carnac et al., 1996; Fagotto et al., 1997; Lemaire et al., 1995). Co-injection of Siamois or β-catenin, but not Xwnt8, overcame the ventralizing effect of Axin, rescuing normal axis formation in a large proportion of embryos (FIG. 4A and Table 1) and restoring expression of dorsal markers (FIG. 4C).

As Xwnt8 or several downstream factors can induce a secondary dorsal axis when injected into the ventral side of the embryo, the ability of Axin to inhibit secondary axis formation was examined. Co-expression of Axin completely inhibited the axis-inducing activity of Xwnt8, Xdsh (a Xenopus Dsh homolog) and dominant-negative GSK-3, while it did not affect secondary axis formation by β-catenin or Siamois (FIGS. 5A, and B). Thus, injection of Axin mRNA can block either normal or secondary dorsal axis formation in Xenopus embryos, apparently by interfering with signaling through the Wnt pathway at a level downstream of Wnt, Dsh and GSK-3, and upstream of β-catenin and Siamois.

7. Expression of Axin does not affect other downstream pathways involved in axis formation.

Induction of the Spemann organizer can be also mimicked by Activin, a potent mesodermal inducer, which at high concentrations induces dorsal mesoderm. Axin did not inhibit the induction of Goosecoid by Activin in the ventral region of early gastrula embryos (FIG. 5C), and had no effect on the formation of an ectopic blastopore lip or a partial secondary axis in Activin-injected embryos (FIG. 5A). These results are consistent with the conclusion that Activin acts downstream of, or in parallel to, the Wnt pathway (Carnac et al., 1996; Fagotto et al., 1997; Wylie et al., 1996).

Axial patterning is also regulated further downstream by the antagonistic activity of factors secreted by the organizer (Noggin, Chordin, Follistatin) and the ventral mesoderm (BMPs). For instance, ventral expression of Noggin, a natural inhibitor of BMPs, or a dominant-negative truncated BMP receptor (ΔBMPR) causes formation of an ectopic axis (Hogan, 1996). However, Axin failed to block the induction of a secondary axis, or the ectopic expression of the dorsal marker Goosecoid, by ventral injection of Noggin or ΔBMPR (FIGS. 5A, C). These results confirm that Axin acts specifically on the Wnt signaling pathway, and does not perturb other pathways involved in early axial patterning.

8. Deletion of the Axin RGS homology region creates a dominant-negative mutant.

Figure 6A:
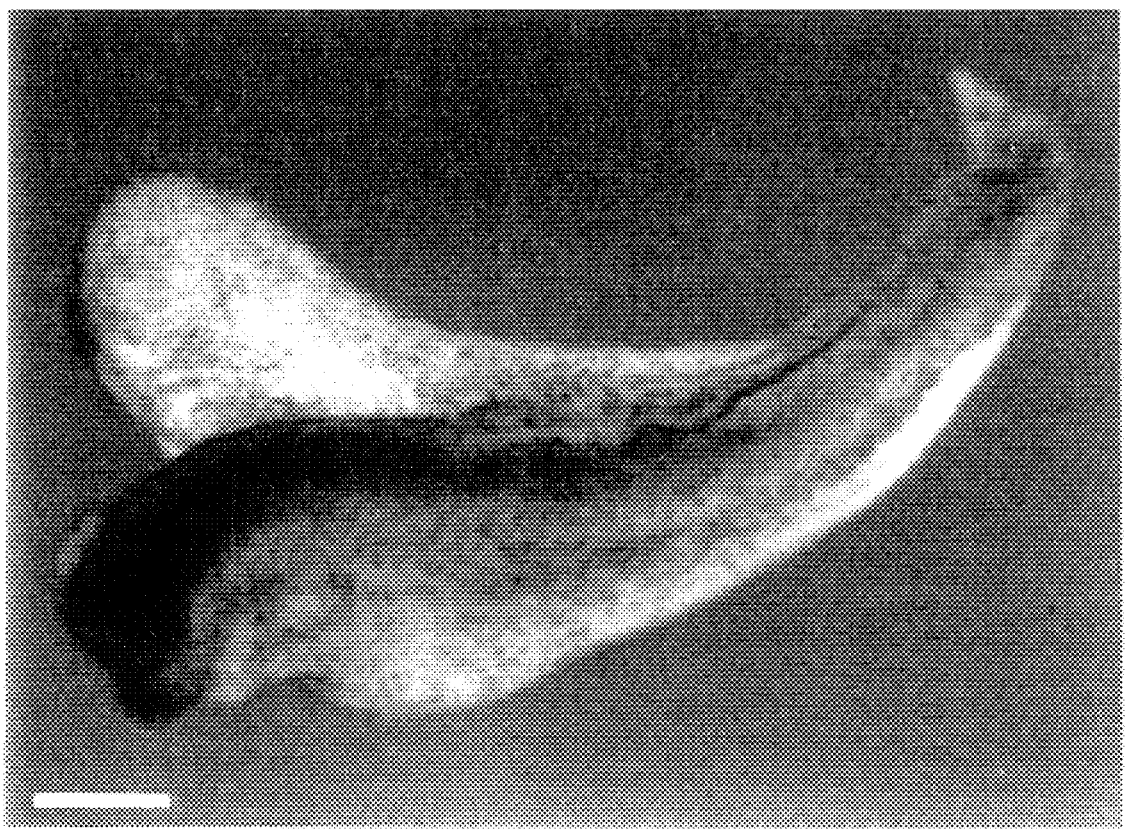
Figure 6B:
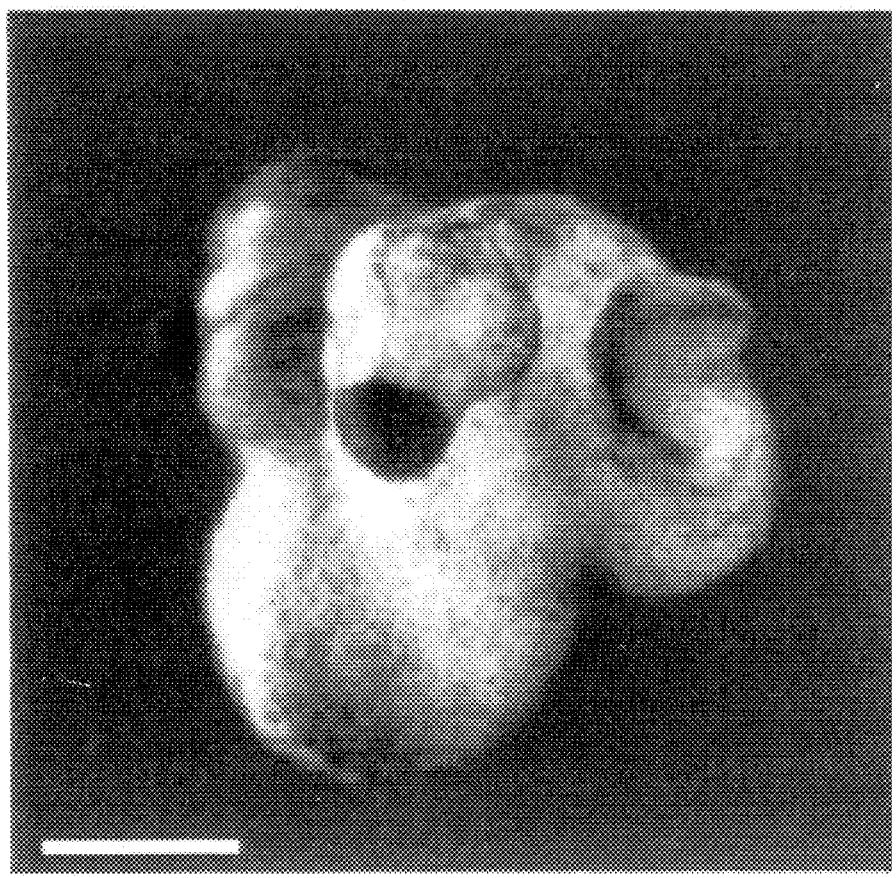
Figure 6C:
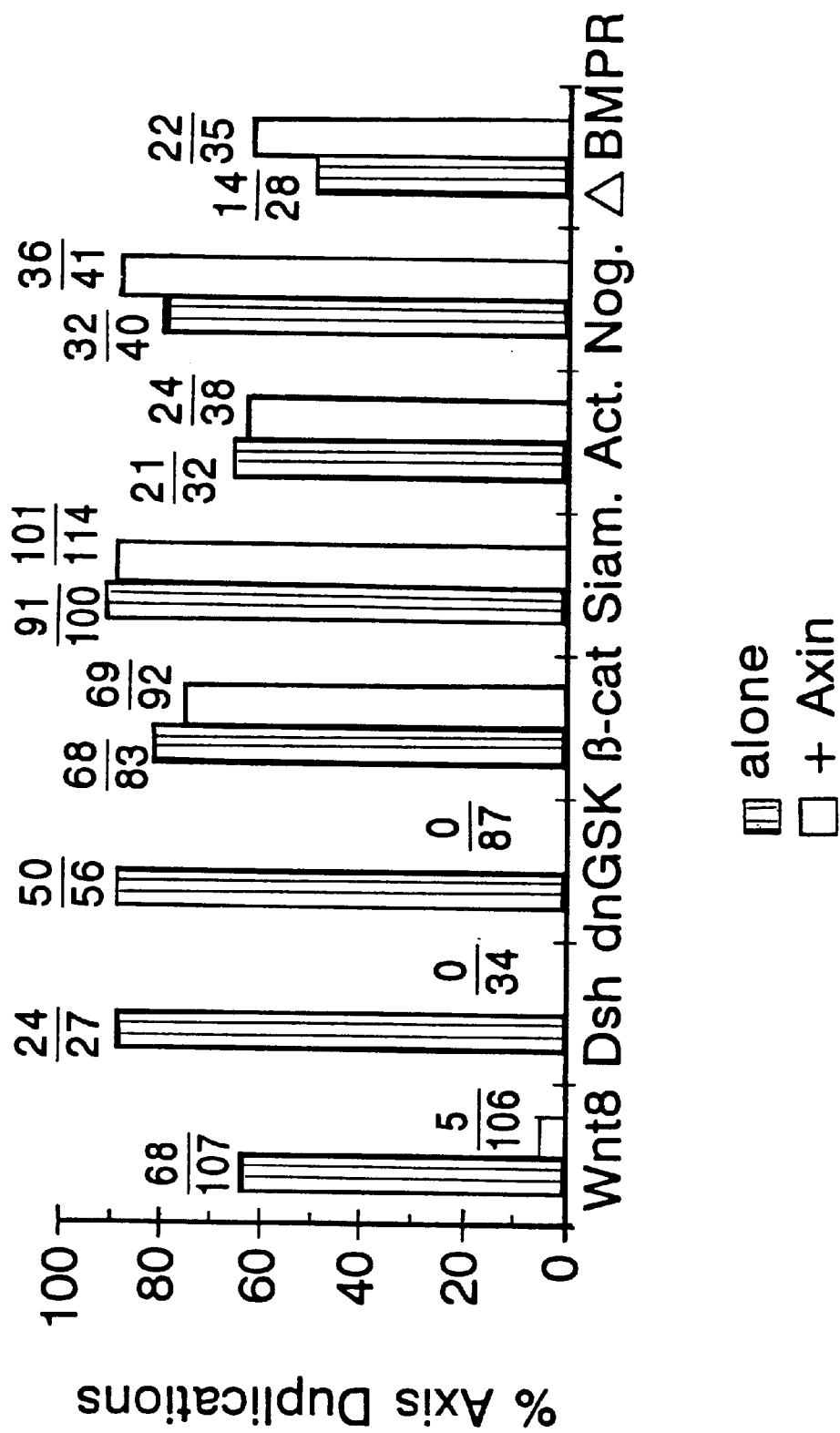
Figure 6D:
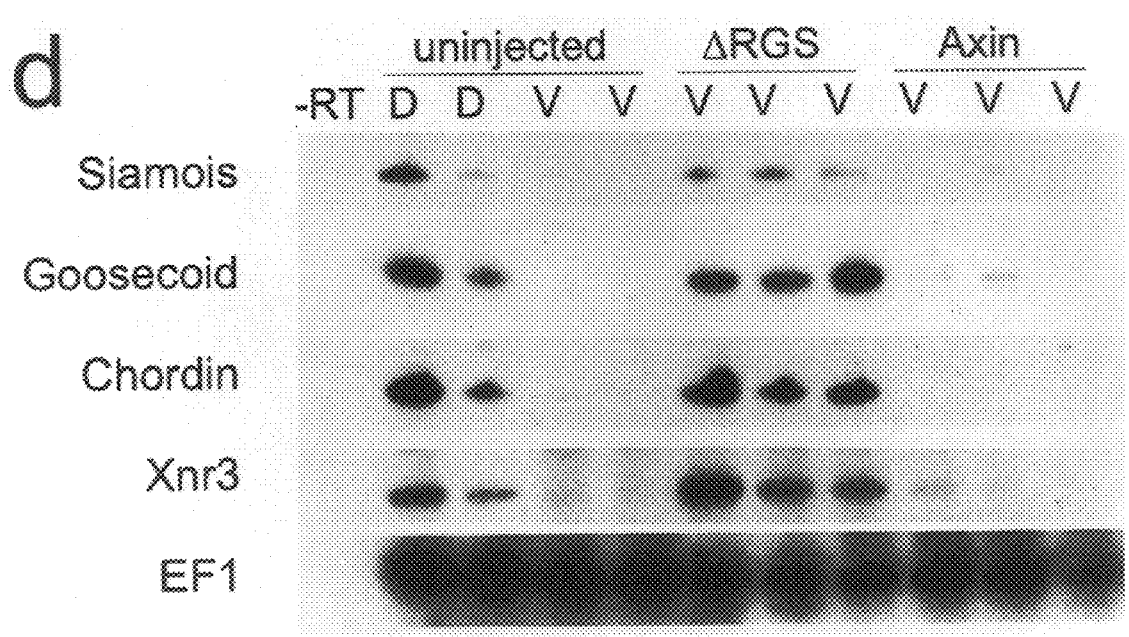
Figure 6E:
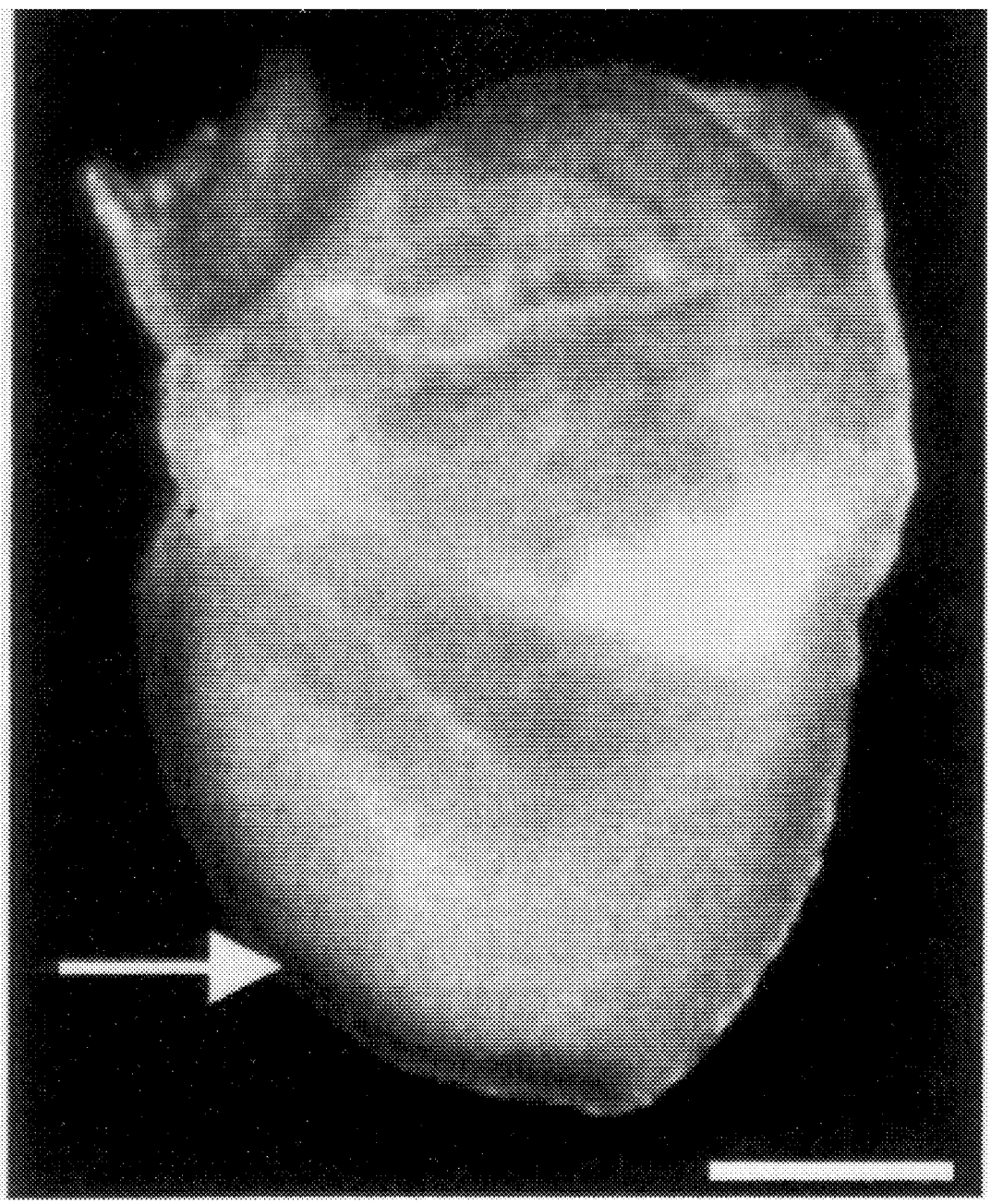
Figure 6F:
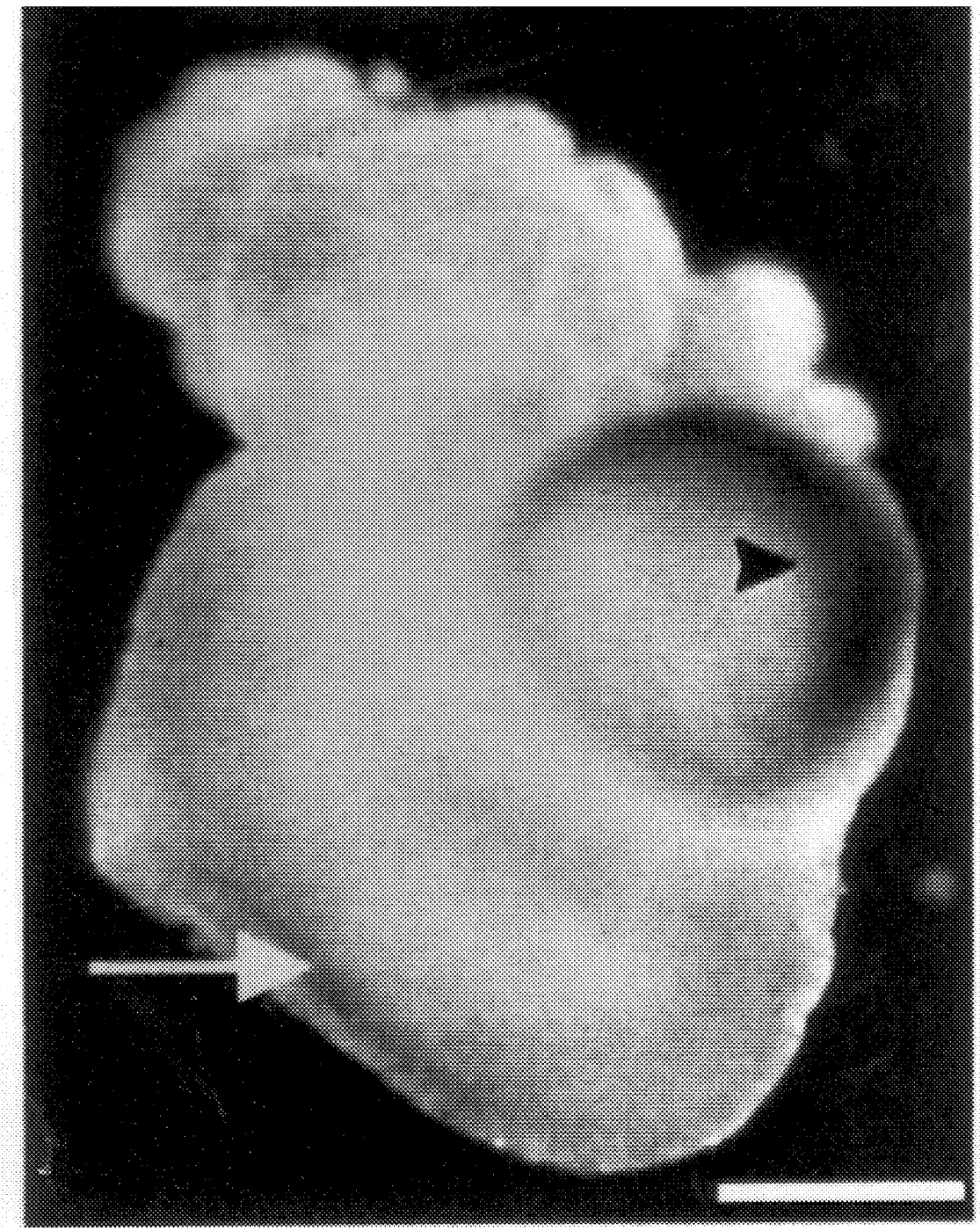
Figure 6G:
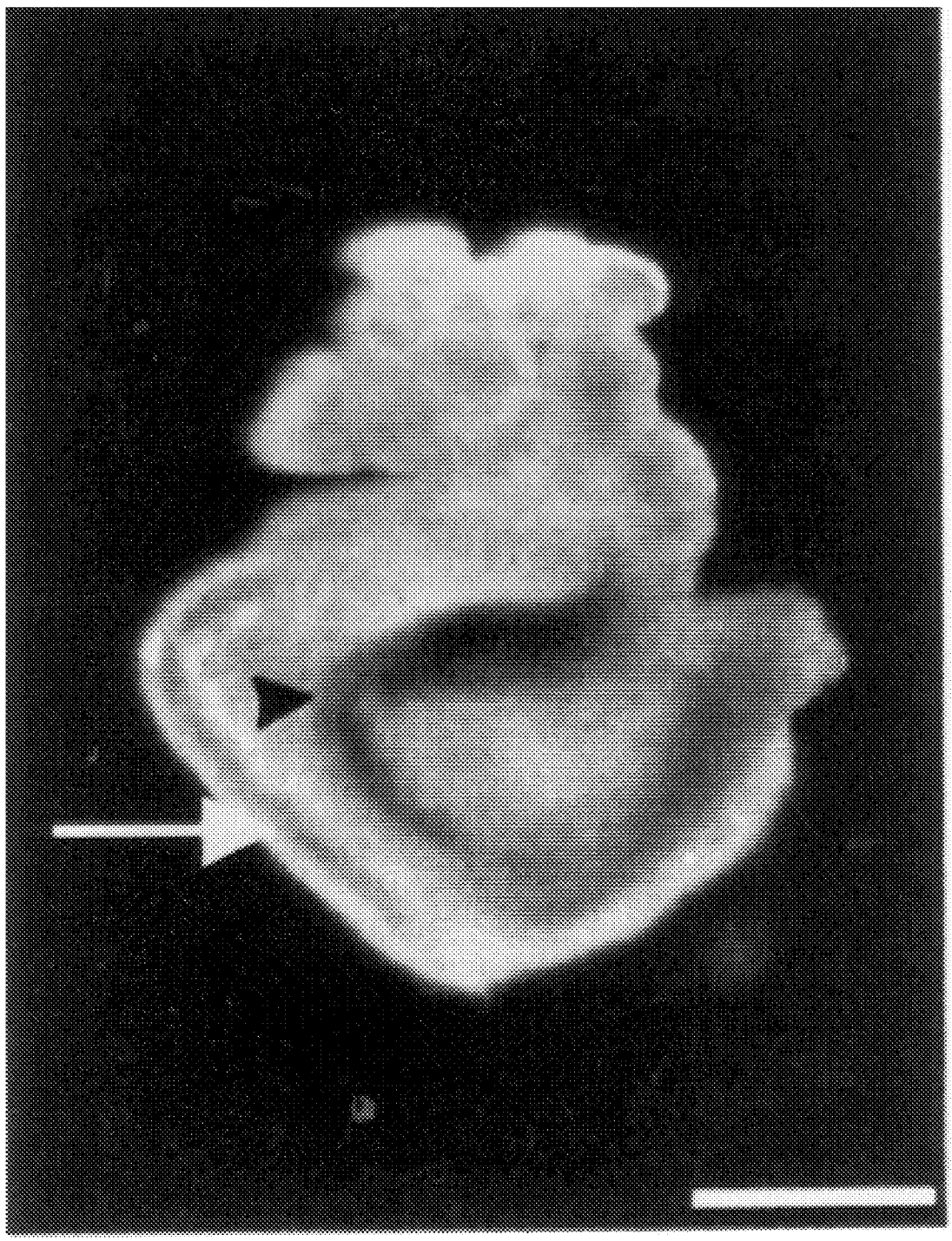

To test the importance of the RGS domain, we injected Xenopus embryos with mRNA encoding ΔRGS, a mutant form of Axin in which the sequences encoding aa 252–351 were deleted. Dorsal injection of ΔRGS revealed that it had lost the ability to ventralize (only 4/44 embryos ventralized, average Dorso-Anterior Index ~5). Surprisingly, ΔRGS acted as a potent dorsalizer when injected ventrally, producing secondary axes (usually complete, including the most anterior head structures) in 87% of embryos (FIGS. 6A–C). ΔRGS induced ectopic expression of several dorsal markers, including Siamois, consistent with an activation of the Nieuwkoop Center signaling pathway (FIG. 6D). Ventral injection of wild type Axin mRNA had no effect on development and did not induce ectopic expression of dorsal markers (FIGS. 6C, and D). However, co-injection of Axin blocked the axis-inducing activity of ΔRGS, as did co-injection of C-cadherin, which binds to and inhibits signaling through β-catenin (Fagotto et al., 1996) (FIG. 6C). Thus, ΔRGS has an effect opposite to that of Axin, and appears to acts through a dominant-negative mechanism to inhibit an endogenous Axin activity. The axial duplications induced by ΔRGS are reminiscent of those caused by loss-of-function Axin alleles in the mouse embryo, two examples of which are shown in FIGS. 6 (E–G).

Discussion

Mutations at the Fused locus have been a subject of interest since the early days of mouse genetics because of their pleiotropic effects on a variety of developmental processes. The most remarkable abnormality seen in early post-implantation embryos homozygous for Fused alleles was the formation of ectopic axial structures, which led to the suggestion that this locus played a role in the determination of the embryonic axis (Gluecksohn-Schoenheimer, 1949). The wild type Fused gene, now called Axin, and a transgenic insertional mutant allele, have been cloned and the structure characterized of $Axin^{Tg1}$. Two of the old mutant alleles, $Axin^{Fu}$ and $Axin^{Kb}$, have also been characterized (Vasicek et al., submitted). The observation that the major Axin mRNA is disrupted in two different alleles that cause axial duplications suggested that the normal gene product plays a negative regulatory role at some step in axis formation. This hypothesis is supported by the observation that dorsal injection of Axin mRNA blocks axis formation in Xenopus embryos, while ventral injection of a dominant-negative form of Axin induces a complete secondary axis. Furthermore, co-injection of Axin with factors in the Wnt signal transduction pathway shows that Axin exerts its effects on axis formation by inhibiting the Wnt pathway. These studies reveal that Axin is a novel regulatory protein for a signaling pathway known to trigger an early step in embryonic axis formation in amphibians. Results, together with the phenotype of Axin mutant embryos, also imply that the Wnt signaling pathway plays an early and critical role in axis formation in mammalian embryos.

1. The Axin gene.

The Axin gene encodes a major mRNA of 3.9 kb, which is expressed ubiquitously in embryos and adult tissues. In the $Axin^{Tg1}$ allele, exon 2 is replaced with ~600 kb of transgene DNA, preventing expression of the major mRNA. Two spontaneous Axin alleles, $Axin^{Fu}$ and $Axin^{Kb}$, are each caused by the insertion of an IAP provirus, within intron 6 or exon 7, respectively (Vasicek et al., submitted). Many of the similarities and differences between the phenotypic effects of Axin alleles can be explained by the nature of these mutations. While the provirus in the $Axin^{Fu}$ intron is efficiently spliced out, resulting in near-normal levels of the 3.9 kb mRNA, the provirus in $Axin^{Kb}$ precludes the production of the normal mRNA. Therefore, the similar recessive defects and embryonic lethality seen in $Axin^{Tg1}$ and $Axin^{Kb}$ (but not $Axin^{Fu}$) embryos can be attributed to the inability of either allele to encode the major Axin mRNA. On the other hand, the dominant effects of $Axin^{Fu}$ and $Axin^{Kb}$, which are not seen in $Axin^{Tg1}$ mice, appear to be a specific consequence of abnormal transcripts associated with the proviral insertions in these alleles (Vasicek et al., submitted).

Two genomic cosmids encoding part of a human Axin homolog map to chromosome 16p13.3 (Accession No. Z69667 and Z81450). Examination of the human genetic map did not reveal any genetic traits (e.g., developmental or neurological defects) that seem likely to be associated with Axin mutations.

The predicted Axin protein includes regions of similarity to two families of proteins involved in signal transduction, RGS and Dsh. Several proteins containing an RGS domain (De Vries et al., 1995; Druey et al., 1996; Koelle and Horvitz, 1996) bind $G_\alpha$ subunits (De Vries et al., 1995; Dohlman et al., 1996) and serve as GTPase-activating proteins (GAPs) for the $G_i$ subfamily of $G_\alpha$ subunits, thus inhibiting signal transduction by accelerating the rate of the intrinsic GTPase (Berman et al., 1996; Hunt et al., 1996; Watson et al., 1996). At least 17 mammalian RGS proteins have been identified, and it is not yet clear if they all serve as GAPs for members of the $G_{i\alpha}$ subfamily, or if some serve as GAPs for other $G_\alpha$ subfamilies, or perform other functions (Dohlman and Thorners, 1997). While the Axin RGS domain contains similar residues at many positions of amino acid conservation among RGS proteins, it differs at other conserved positions, and contains two short inserts not present in other RGS domains (FIG. 3B) (SEQ ID NO: 1, 4, and 10). Thus, whether the Axin RGS is a $G_\alpha$ GAP remains to be determined. Axin also displays homology to a 50 aa sequence within a conserved N-terminal region of Drosophila and vertebrate Dsh proteins. The importance of this sequence is unknown, although deletion of a 165 aa segment including this sequence rendered the Drosophila protein inactive (Yanagawa et al., 1995).

2. Axin and Wnt signaling in establishment of the amphibian Nieuwkoop Center.

Based on its ability to block ectopic axis formation in Xenopus embryos by Xwnt8, Dsh or dnGSK-3, Axin appears to negatively regulate signaling through the Wnt pathway, either at the level of GSK-3 or further downstream. Furthermore, its inability to block the effects of β-catenin or Siamois suggests that Axin acts upstream of β-catenin (FIG. 7). GSK-3 is a Ser/Thr protein kinase whose activity results in the phosphorylation of β-catenin and its consequent degradation. GSK-3 may directly phosphorylate β-catenin (Yost et al., 1996), or its effects on β-catenin may be mediated by the phosphorylation of adenomatous polyposis coli (APC), which associates with β-catenin and GSK-3 (Miller and Moon, 1996). When GSK-3 activity is inhibited, either naturally through the activity of Wnt and Dsh, or experimentally by dnGSK-3, the level of cytosolic β-catenin is increased, downstream effectors are activated, and Nieuwkoop Center activity results. Thus, both Axin and GSK-3 negatively regulate formation of the Nieuwkoop Center by inhibiting the same signaling pathway.

One hypothetical mechanism for the similar action of Axin and GSK-3 (FIG. 7) is suggested by the observation that Axin can bind to the Ser/Thr protein phosphatase PP2A. If Axin were to inhibit PP2A activity, and if PP2A de-phosphorylated the GSK-3 substrate(s) involved in Wnt signaling, then the overexpression of Axin would increase the level of phosphorylation of this substrate. Thus, even if GSK-3 activity were reduced by Dsh or dnGSK-3, the substrate would remain highly phosphorylated, which could explain why Axin appears epistatic to these two proteins. Alternatively, Axin might stimulate GSK-3 activity by another mechanism that can overcome its inhibition by Dsh or dnGSK-3. A third possibility is suggested by the demonstrated importance of the RGS domain for the ability of Axin to inhibit Wnt signaling and ventralize the frog embryo. There is no evidence for a $G_\alpha$ protein in the Wnt pathway, and the evidence that Axin functions downstream of Dsh and GSK-3 would argue against an activity at the level of a hypothetical G-protein coupled to a Wnt receptor. However, the Axin RGS domain, if it is a functional $G_\alpha$ GAP, might inhibit a second signaling pathway involving a $G_\alpha$ protein, which converges with and stimulates the Wnt pathway at a level downstream of GSK-3. In order to explain the ability of high levels of Axin to block the Wnt pathway, this second signal would have to be required for some step in the transmission of the Wnt signal (e.g., cytosolic accumulation of β-catenin) in the early frog embryo.

Not only does deletion of the RGS region abolish the axis-inhibiting properties of Axin, but it creates a dominant-negative form that can induce an ectopic dorsal axis. An obvious implication is that the amphibian embryo contains a protein homologous to Axin, which normally serves to inhibit ectopic axis formation, and whose activity is blocked by ΔRGS. This conclusion is consistent with the observation that loss-of-function Axin mutations in the mouse cause the development of ectopic axial structures. Thus, not only is Axin capable of inhibiting signaling through the Wnt pathway when it is over-expressed, but this appears to be a natural function of the protein. Presumably, the levels of endogenous Axin in the embryo are high enough to prevent signaling in the absence of a strong upstream signal (e.g., a Wnt ligand), but low enough to allow signaling when the pathway is activated by a natural or experimental stimulus. While the dominant-negative mechanism of ΔRGS remains to be determined, one possibility is that it competes for binding to a protein to which Axin normally binds, but fails to perform the function carried out by the RGS domain.

3. Axin, Wnts and axis formation in mammalian embryos.

The ability of Axin to regulate an early step in Xenopus axis formation mediated by the Wnt signaling pathway, together with the occurrence of axial duplications in Axin mutant mouse embryos, argues strongly that an evolutionarily conserved mechanism involving the Wnt pathway plays a critical role in embryonic axis formation in mammals as well as amphibians. In Xenopus, signaling through components of the Wnt pathway is thought to confer Nieuwkoop Center activity to a group of dorsal-vegetal blastomeres, which consequently secrete factors that induce formation of the organizer by the adjacent dorsal mesoderm. in the mouse, the equivalent of the organizer is the node, a group of cells at the anterior end of the primitive streak (Beddington, 1994). Fate mapping of the pre-streak embryo indicates that the node derives from epiblast cells at the future posterior pole (Lawson et al., 1991). While the location of the Nieuwkoop Center equivalent (i.e., the cells that induce formation of the organizer) is unknown, the most likely locations are the posterior extraembryonic or embryonic ectoderm proximal to the cells fated to form the node, or the overlying visceral endoderm (Bachvarova, 1996; Conlon and Beddington, 1995).

During normal mouse embryogenesis, the Wnt signaling pathway is activated in a discrete region of the early egg cylinder, by the localized production of a Wnt or another stimulus that activates downstream components of the Wnt pathway. This localized signal establishes the A-P axis of the embryo, and the responding cells constitute a Nieuwkoop Center equivalent (NCE). According to this model, the ubiquitously expressed Axin serves to attenuate the response to this signal, so that cells in regions of the embryo not exposed to the signal, or exposed to low levels, do not respond, and only a single NCE is formed at the appropriate developmental stage. In mutant embryos lacking Axin, the Wnt pathway could be inappropriately activated and multiple NCE would result. The presence of multiple, discrete axes in mutant embryos could be explained by lateral inhibition mechanism, whereby once a NCE or organizer is formed, it restricts axis formation in adjacent regions of the embryo (Cooke, 1972; Khaner and Eyal-Giladi, 1989; Ziv et al., 1992).

The hypothesis that the Wnt pathway is important for mammalian axis formation is supported by the observation that ubiquitous expression of Cwnt-8C in transgenic embryos causes axial duplications (Pöpperl et al., 1997). Also consistent is the failure of β-catenin null mutant mouse embryos to undergo gastrulation (Haegel et al., 1995). No Wnt mutants produced so far have affected early events in axis formation, and the expression of Wnts in pre-streak mouse embryos has not been reported (Moon et al., 1997; Parr and McMahon, 1994), leaving open the question of what signal triggers this pathway in the normal embryo. In the pre-streak chick embryo, on the other hand, Cwnt-8c is expressed in the posterior marginal zone, a region possibly equivalent to the Nieuwkoop Center (Hume and Dodd, 1993).

While the earliest stage at which axial duplications originate in Axin mutant embryos has not been defined, they appear to occur by the stage at which NCE activity would be expected, i.e., the early egg cylinder. Some of earliest $Axin^{Ki/Ki}$ embryos examined (E7.0–7.5) contained a bifurcated epiblast with two discrete amniotic cavities or two primitive streaks (Glueksohn-Schoenheimer, 1949; Tilghman, 1996). At later stages, in addition to duplication of anterior axial mesoderm (e.g., FIGS. 7F, and G), duplication of the allantois (derived from posterior streak) has been observed in both $Axin^{Tg1}$ and $Axin^{Ki}$ embryos (Glueksohn-Schoenheimer, 1949; Perry et al., 1995). In contrast, transplantation of the node to an ectopic site resulted in formation of ectopic notochord, neural tube and somites, but not allantois (Beddington, 1994). Therefore, structures derived from the most anterior and posterior portions of the primitive streak are duplicated in Axin mutant embryos, suggesting that the duplications precede the formation of the streak. The extent of anterior neuroectodermal development of the ectopic axes in Axin mutant embryos remains to be further studied using molecular markers: "complete twinning" as well as partial duplications were reported in $Axin^{Ki}$ embryos, but ectopic forebrain structures have not yet been documented in $Axin^{Tg1}$ or $Axin^{Kb}$ embryos.

In addition to their effects on axis formation, Axin mutations cause neuroectodermal defects (incomplete closure, malformation or truncation of the head folds) cardiac defects and embryonic lethality in homozygotes. It remains to be determined whether these abnormalities are also due to defective regulation of Wnt signaling pathways. Anterior truncations have been observed in transgenic mouse embryos that ubiquitously expressed Cwnt-8C (R. Beddington, personal communication) and in frog embryos ectopically expressing Xwnt-8 after the mid-blastula transition (Christian and Moon, 1993). Therefore, inappropriate Wnt signaling may also account for the neuroectodermal defects in Axin mutant embryos. Another interesting question that can now be addressed is the molecular basis of the dominant defects seen in $Axin^{Fu}$, $Axin^{Kb}$ and $Axin^{Ki}$ heterozygotes, which were attributed to gain-of-function mutations (Greenspan and O'Brien, 1986). Analysis of $Axin^{Fu}$ and $Axin^{Kb}$ suggests that their similar dominant effects may be mediated by C-terminally truncated Axin proteins that are potentially encoded by abnormally spliced transcripts (Vasicek et al., manuscript submitted). It is possible that these abnormal Axin proteins perturb Wnt signaling pathways involved in brain and skeletal development.

References for the First Section

Bachvarova, R. F. (1996) "Anterior-posterior polarization and mesoderm inducing factors in the pregastrula mouse embryo." Comparison to chick and frog embryos. *Adv. Dev. Biol.* 4: 147–191.

Beddington, R. S. P. (1994) "Induction of a second neural axis by the mouse node." *Development* 120: 613–620.

Berman, D. M., Wilkie, T. M., and Gilman, A. G. (1996) "GAIP and RGS4 are GTPase-activating proteins for the $G_i$ subfamily of G protein α subunits." *Cell* 86: 445–452.

Carnac, G., Kodjabachian, L., Gurdon, J. B., and Lemaire, P. (1996) "The homeobox gene Siamois is a target of the Wnt dorsalization pathway and triggers organizer activity in the absence of mesoderm." *Development* 122: 3055–3065.

Chenchik, A., Moqadam, J., and Siebert, P. (1995) "Marathon cDNA amplification: a new method for cloning full-length cDNAs." *CLONETECHniques* 10: 5–8.

Christian, J. L., and Moon, R. T. (1993) "Interactions between Xwnt-8 and Spemann organizer signaling pathways generate dorsoventral pattern in the embryonic mesoderm of Xenopus." *Genes Dev* 7: 13–28.

Conlon, F., and Beddington, R. (1995) "Mouse gastrulation from a frog's perspective." *Semin. Dev. Biol.* 6: 249–256.

Cooke, J. (1972) "Properties of the primary organization field in the embryo of Xenopus laevis. II. Positional information for axial organization in embryos with two head organizers." *J Embryol Exp Morphol* 28: 27–46.

De Vries, L., Mousli, M., Wurmser, A., and Farquhar, M. G. (1995) "GAIP, a protein that specifically interacts with the trimeric G protein G alpha i3, is a member of a protein family with a highly conserved core domain." *Proc Natl Acad Sci U S A* 92: 11916–11920.

Dingwall, C., and Laskey, R. A. (1991) "Nuclear targeting sequences—a consensus?" *Trends Biochem Sci* 16: 478–81.

Dohlman, H. G., Song, J., Ma, D., Courchesne, W. E., and Thorners, J. (1996) "Sst2, a negative regulator of pheromone signaling in the yeast *Saccharomyces cerevisiae*: expression, localization, and genetic interaction and physical association with Gpal (the G-protein α subunit)." *Molec. Cell. Biol.* 16: 5194–5209.

Dohlman, H. G., and Thorners, J. (1997) "RSG proteins and signaling by heterotrimeric G proteins." *J. Biol. Chem.* 272: 3871–4.

Druey, K. M., Blumer, K. J., Kang, V. H., and Kehrl, J. H. (1996) "Inhibition of G-protein-mediated MAP kinase activation by a new mammalian gene family." *Nature* 379: 742–746.

Fagotto, F., Funayama, N., Gluck, U., and Gumbiner, B. M. (1996) "Binding to cadherins antagonizes the signaling activity of beta-catenin during axis formation in Xenopus." *J. Cell Biol.* 132: 1105–1114.

Fagotto, F., Guger, K., and Gumbiner, B. M. (1997) "Induction of the primary dorsalizing center in Xenopus by the Wnt/GSK/β-catenin signaling pathway, but not by Vg1, Activin, or Noggin." *Development* 124: 453–460.

Fagotto, F., and Gumbiner, B. M. (1994) "Beta-catenin localization during Xenopus embryogenesis: accumulation at tissue and somite boundaries." *Development* 120: 3667–79.

Funayama, N., Fagotto, F., McCrea, P., and Gumbiner, B. M. (1995) "Embryonic axis induction by the armadillo repeat domain of beta-catenin: evidence for intracellular signaling." *J. Cell Biol.* 128: 959–68.

Gardner, R. L., Meredith, M. R., and Altman, D. G. (1992) "Is the anterior-posterior axis of the fetus specified before implantation in the mouse?" *J. Exp. Zool.* 264: 437–443.

Gluecksohn-Schoenheimer, S. (1949) "The effects of a lethal mutation responsible for duplications and twinning in mouse embryos." *J. Exp. Zool.* 110: 47–76.

Greenspan, R. J., and O'Brien, M. C. (1986) "Genetic analysis of mutations at the fused locus in the mouse." *Proc Natl Acad Sci U S A* 83: 4413–7.

Haegel, H., Larue, L., Ohsugi, M., Fedorov, L., Herrenknecht, K., and Kemler, R. (1995) "Lack of beta-catenin affects mouse development at gastrulation." *Development* 121: 3529–3537.

Heasman, J., Crawford, A., Goldstone, K., Garner-Hamrick, P., Gumbiner, B., McCrea, P., Kintner, C., Noro, C. Y., and Wylie, C. (1994) "Overexpression of cadherins and underexpression of beta-catenin inhibit dorsal mesoderm induction in early Xenopus embryos." *Cell* 79: 791–803.

Hogan, B. L. (1996) "Bone morphogenetic proteins: multifunctional regulators of vertebrate development." *Genes Dev* 10: 1580–94.

Hoppler, S., Brown, J. D., and Moon, R. T. (1996) "Expression of a dominant-negative Wnt blocks induction of MyoD in Xenopus embryos." *Genes Dev* 10: 2805–17.

Hume, C. R., and Dodd, J. (1993) "Cwnt-8C: a novel Wnt gene with a potential role in primitive streak formation and hindbrain organization." *Development* 119: 1147–1160.

Hunt, T. W., Fields, T. A., Casey, P. J., and Peralta, E. G. (1996) "RGS10 is a selective activator of $Gα_i$ GTPase activity" *Nature* 383: 175–177.

Jacobs-Cohen, R. J., Spiegelman, M., Cookingham, J. C., and Bennett, D. (1984) "Knobbly, a new dominant mutation in the mouse that affects embryonic ectoderm organization." *Genet. Res.* 43: 43–50.

Kao, K. R., and Elinson, R. P. (1988) "The entire mesodermal mantle behaves as Spemann's organizer in dorsoanterior enhanced Xenopus laevis embryos." *Dev Biol* 127: 64–77.

Khaner, O., and Eyal-Giladi, H. (1989) "The chick's marginal zone and primitive streak formation. I. Coordinative effect of induction and inhibition." *Dev Biol* 134: 206–214.

Klingensmith, J., Nusse, R., and Perrimon, N. (1994) "The Drosophila segment polarity gene dishevelled encodes a novel protein required for response to the wingless signal." *Genes Dev* 8: 118–30.

Koelle, M. R., and Horvitz, H. R. (1996) "EGL-10 regulates G protein signaling in the C. elegans nervous system and shares a conserved domain with many mammalian proteins." *Cell* 84: 115–125.

Kozak, M. (1986) "Point mutations define a sequence flanking the AUG initiator codon that modulates translation by eukaryotic ribosomes." *Cell* 44: 283–92.

Lawson, K. A., Meneses, J. J., and Pedersen, R. A. (1991) "Clonal analysis of epiblast fate during germ layer formation in the mouse embryo." *Development* 113: 891–911.

Lemaire, P., Garrett, N., and Gurdon, J. B. (1995) "Expression cloning of Siamois, a Xenopus homeobox gene expressed in dorsal-vegetal cells of blastulae and able to induce a complete secondary axis." *Cell* 81: 85–94.

Lyon, M. F., Rastan, S., and Brown, S. D. M. (1996) *Genetic Variants and Strains of the Laboratory Mouse* (Oxford: Oxford University Press).

Miller, J. R., and Moon, R. T. (1996) "Signal transduction through β-catenin and specification of cell fate during embryogenesis." *Genes Dev.* 10: 2527–2539.

Moon, R. T., Brown, J. D., and Torres, M. (1997) "WNTs modulate cell fate and behavior during vertebrate development." *Trends Genetd.* 13: 157–162.

Parr, B. A., and McMahon, A. P. (1994) "Wnt genes and vertebrate development." *Curr. Opin. Genet. Dev.* 4: 523–8.

Perry, W. L. I., Vasicek, T. J., Lee, J. J., Rossi, J. M., Zeng, L., Zhang, T., Tilghman, S. M., and Costantini, F. (1995) "Phenotypic and molecular analysis of a transgenic insertional allele of the mouse Fused locus." *Genetics* 141: 321–332.

Pierce, S. B., and Kimelman, D. (1995) "Regulation of Spemann organizer formation by the intracellular kinase Xgsk-3. " *Development* 121: 755–765.

Pöpperl, H., Schmidt, C. W., V., Dodd, J., Krumlauf, R., and Beddington, R. S. P. (1997) "Misexpression of Cwnt8C in the mouse induces an ectopic embryonic axis and causes a truncation of the anterior neurectoderm." *Development* (in press).

Rupp, R. A., Snider, L., and Weintraub, H. (1994) "Xenopus embryos regulate the nuclear localization of XMyoD." *Genes Dev* 8: 1311–23.

Sasaki, H., and Hogan, B. L. (1993) "Differential expression of multiple fork head related genes during gastrulation and axial pattern formation in the mouse embryo." *Development* 118: 47–59.

Sasaki, H., and Hogan, B. L. (1994) "HNF-3 beta as a regulator of floor plate development." *Cell* 76: 103–15.

Slack, J. M. (1994) "Inducing factors in Xenopus early embryos." *Curr. Biol.* 4: 116–126.

Sokol, S. Y. (1996) "Analysis of Dishevelled signalling pathways during Xenopus development." *Curr. Biol.* 6: 1456–1467.

St-Jacques, B., and McMahon, A. P. (1996) "Early mouse development: lessons from gene targeting." *Curr. Opin. Genet. Dev.* 6: 439–444.

Sussman, D. J., Klingensmith, J., Salinas, P., Adams, P. S., Nusse, R., and Perrimon, N. (1994) "Isolation and characterization of a mouse homolog of the Drosophila segment polarity gene dishevelled." *Devel. Biol.* 166: 73–86.

Suzuki, A., Thies, R. S., Yamaji, N., Song, J. J., Wozney, J. M., Murakami, K., and Ueno, N. (1994) "A truncated bone morphogenetic protein receptor affects dorsal-ventral patterning in the early Xenopus embryo." *Proc Natl Acad Sci U S A* 91: 10255–10259.

Tilghman, S. M. (1996) "Lessons learned, promises kept: a biologist's eye view of the Genome Project." *Genome Res* 6: 773–80.

Watabe, T., Kim, S., Candia, A., Rothbacher, U., Hashimoto, C., Inoue, K., and Cho, K. W. (1995) "Molecular mechanisms of Spemann's organizer formation: conserved growth factor synergy between Xenopus and mouse." *Genes Dev* 9: 3038–3050.

Watson, N., Linder, M. E., Druey, K. M., Kehrl, J. H., and Blumer, K. J. (1996) "RGS family members: GTPase-activating proteins for heterotrimeric G-protein α-subunits." *Nature* 383: 172–175.

Wilkinson, D. G. (1992) "Whole mount in situ hybridization of vertebrate embryos." In *In situ hybridization: a practical approach*. D. G. Wilkinson, ed. (Oxford: IRL Press), pp. 75–83.

Wylie, C., Kofron, M., Payne, C., Anderson, R., Hosobuchi, M., Joseph, E., and Heasman, J. (1996) "Maternal beta-catenin establishes a 'dorsal signal' in early Xenopus embryos." *Development* 122: 2987–2996.

Yanagawa, S., van Leeuwen, F., Wodarz, A., Klingensmith, J., and Nusse, R. (1995) "The dishevelled protein is modified by wingless signaling in Drosophila." *Genes Dev* 9: 1087–1097.

Yost, C., Torres, M., Miller, J. R., Huang, E., Kimelman, D., and Moon, R. T. (1996) "The axis-inducing activity, stability, and subcellular distribution of beta-catenin is regulated in Xenopus embryos by glycogen synthase kinase 3." *Genes Dev.* 10: 1443–1454.

Ziv, T., Shimoni, Y., and Mitrani, E. (1992) "Activin can generate ectopic axial structures in chick blastoderm explants." *Development* 115: 689–694.

Second Section

Wnts are a family of secreted polypeptides which play many functions in development and tumorigenesis (Nusse, 1992; Nusse and Varmus, 1992). The earliest Wnt genes to be identified were shown to have oncogenic effects in the mouse mammary gland. Wnt-1 was first identified as a target for activation by insertion of a retrovirus in mammary tumors ((Nusse, 1992; Nusse and Varmus, 1992) and references therein), and inappropriate expression of Wnt-1 can also cause mammary gland tumorigenesis in transgenic mice (Tsukamoto et al., 1988). Wnts are believed to utilize a signal transduction pathway including the following components: The receptors for Wnts are believed to be members of the frizzled family (Bhanot et al., 1996; Chan et al., 199; Wang et al., 1996; Yang-Synder et al., 1996). The next known component of the pathway is Dishevelled (DSH) (Noordermeer et al., 1994), a cytoplasmic protein that is phosphorylated in response to wingless (Yanagawa et al., 1995). Through an unknown mechanism, Dsh inhibits the activity of glycogen synthase kinase-3 (GSK-3). In the absence of a Wnt signal, GSK-3 activity leads (directly or indirectly) to the phosphorylation and consequent degradation of β-catenin. In the presence of a Wnt signal, GSK-3 is inhibited, increasing the cytosolic level of β-catenin, and promoting its interaction with downstream effectors (Behrens et al., 1996; Funayama et al., 1995; Molenaar et al., 1996; Yost et al., 1996). The product of the APC (adenomatous polyposis coli) gene is also involved in Wnt signaling, apparently forming a complex with GSK-3 and β-catenin (Munemitsu et al., 1995; Papkoff et al., 1996; Polakis, 1997; Rubin et al., 1996; Rubinfeld et al., 19930.

Mutations in at least two components of the Wnt signaling pathway, APC, and β-catenin, have been associated with a variety of cancers, including hereditary colorectal cancer (Familial Adenomatous Polyposis coli, of FAP) and melanoma (Morin et al., 1997; Peifer, 1997; Polakis, 1997; Rubinfeld et al., 1997). While colon cancer is the primary manifestation of FAP, some patients also develop tumors in other sites, such as other regions of the GI tract, in the thyroid, brain and abdominal cavity (Polakis, 1997). The role of APC in tumorigenesis is thought to be mediated by β-catenin. Normally, APC together with GSK-3 regulates the levels of free cytosolic β-catenin, which remain low. When APC is mutated, degradation of β-catenin is disrupted and levels of β-catenin are greatly increased (Peifer, 1997; Polakis, 1997). In addition, mutations in the β-catenin that interfere with its normal regulation have been found in cases of colon cancer (Morin et al., 1997) and melanoma (Rubinfeld et al., 1997).

Axin has been shown to negatively regulate signaling through the Wnt pathway, based on its ability to block induction of a secondary embryonic axis in frog embryos, when co-injected with mRNAs for Wnt, dishevelled or a dominant-negative mutant form of GSK-3 (Zeng et al., 1997). Axin cannot block axis duplication caused by injection of mRNA for β-catenin, indicating that it functions upstream of β-catenin, but downstream of GSK-3. Therefore, Axin is likely to promote the degradation of β-catenin, either directly or indirectly. Overexpression of Axin in pre-cancerous or tumor cells may be expected to counteract the effects of mutations in APC, β-catenin or other associated proteins, which would otherwise increase the levels of cytosolic β-catenin leading to cellular transformation. Therefore, Axin may be useful clinically to counteract the effects of such mutations. In addition, mutations in the Axin gene itself may result in loss of regulation of β-catenin levels and consequent tumorigenesis, i.e., Axin may be a tumor suppressor gene. Such mutations could either be loss-of-function mutations, or dominant-negative mutations. The ability of one such mutation (a deletion of the RGS domain of Axin) to create a dominant negative mutant form of the protein has been demonstrated (Zeng et al., 1997).

References for the Second Section

Behrens, J., von Kries, J. P., Kuhl, M., Bruhn, L., Wedlich, D., Grosschedl, R., and Birchmeier, W. (1996) "Functional interaction of beta-catenin with the transcription factor LEF-1, *Nature* 382: 638–642.

Bhanot, P., Brink, M., Samos, C. H., Hesieh, J. C., Wang, Y., Macke, J. P., Andrew, D., Nathans, J., and Nusse, R. (1996) "A new member of the frizzled family from Drosophila functions as a Wingless receptor. *Nature* 382: 225–230.

Chan, S. D., Karpf, D. B., Fowlkes, M. E., Hooks, M., Bradley, M. S., Vuong, V., Bambino, T., Liu, M. Y., Arnaud, C. D., Strewler, G. J., and et al. (1992) "Two homologs of the Drosophila polarity gene frizzled (fz) are widely expressed in mammalian tissues. *J. Biol. Chem* 267: 25202–25207.

Funayama, N., Fagotto, F., McCrea, P., and Gumbiner, B. M. (1995) "Embryonic axis induction by the armadillo repeat domain of beta-catenin: evidence for intercellular signaling." *J. Cell. Biol.* 128: 959–968.

Molenaar, M., van de Wetering, M., Oosterwegel, M., Peterson-Maduro, J., Godsave, S., Korinek, V., Roose, J., Destree, O., and Clevers, H. (1996) "Xtcf-3 transcription factor mediates beta-catenin-induced axis formation in Xenopus embryos. *Cell* 86: 391–399.

Morin, P. J.., Sparks, A. B., Korinek, V., Barker, N., Clevers, H., Vogelstein, B., and Kinzler, K. W. (1997) "Activation of beta-catenin-Tcf signaling in colon cancer by mutations in beta-catenin or APC [see comments]. *Science* 275: 1787–1790.

Munemitsu, S., Albert, I., Souza, B., Rubinfeld, B., and Polakis, P., (1995). "Regulation of intracellular beta-catenin levels by the adenomatous polyposis coli (APC) tumor-suppressor protein. *Proc. Natl. Acad. Sci. U.S.A.* 92: 3046–3050.

Noordermeer, J., Klingensmith, J., Perrimon, N., and Nusse, R. (1994) "Dishevelled and armadillo act in the wingless signaling pathway in Drosophila. *Nature* 367: 80–83.

Nusse, R. (1992) "The Wnt gene family in tumorigenesis and in normal development [Review]. *J. Steroid Biochem. Mol. Biol.* 43: 9–12.

Nusse, R., and Varmus, H. E. (1992) "Wnt genes" *Cell* 69: 1073–1087.

Papkoff, J., Rubinfeld, B., Schryver, B., and Polakis, P. (1996) "Wnt-1 regulates free pcols of catenins and stabilizes APC-catenin complexes." *Mol. Cell. Biol.* 16: 2128–2134.

Peifer, M., (1997) "Beta-catenin as oncogene: the smoking gun." *Science* 275: 1752–1753.

Polakis, P. (1997) "The adenomatous polyposis coli (APC) tumor suppressor." *Biochim. Biophys. Acta.* 1332: F127–147.

Rubinfeld, B., Albert, I., Porfiri, E., Fiol, C., Munemitsu, S., and Polakis, P. (1996) "Binding of GSK3β to the APC-β-catenin complex and regulation of complex assembly." *Science* 272: 1023–1026.

Rubinfeld, B., Robbins, P., El-Gamil, M., Albert, I., Porfiri, E., and Polakis, P. (1997) "Stabilization of beta-catenin by genetic defects in melanoma cell lines." *Science* 275: 1790–1792.

Rubinfeld, B., Souza, B., Albert, I., Muller, O., Chamberlain, S. H., Masiarz, F. R., Munemitsu, S., and Polakis, P. (1993) "Association of the APC gene product with beta-catenin." *Science* 262: 1731–1734.

Tsukamoto, A. S., Grosschedl, R., Guzman, R. C., Parslow, T., and Varmus, H. E. (1988) "Expression of the int-1 gene in transgenic mice is associated with mammary gland hyperplasia and adenocarcinomas in male and female mice." *Cell* 55: 619–625.

Wang, Y., Macke, J. P., Abella, B. S., Andreasson, K., Worley, P., Gilbert, D. J., Copeland, N. G., Jenkins, N. A., and Nathans, J., (1996) "A large family of putative transmembrane receptors homologous to the product of the Drosophila tissue polarity gene frizzled." *J. Biol. Chem.* 271: 4468–4476.

Yanagawa, S., van Leeuwen, F., Wodarz, A., Klingensmith, J., and Nusse, R. (1995) "The dishevelled protein is modified by wingless signaling in Drosophila." *Genes Dev.* 9: 1087–1097.

Yang-Synder, J., Miller, J. R., Brown, J. D., Lai, C. J., and Moon, R. T. (1996) "A frizzled homolog functions in a vertebrate Wnt signaling pathway." *Curr. Biol.* 6: 1302–1306.

Yost, C., Torres, M., Miller, J. R., Huang, E., Kimelman, D., and Moon, R. T. (1996) "The axis-inducing activity, stability, and subcellular distribution of beta-catenin is regulated in Xenopus embryos by glycogen synthase kinase 3." *Genes Dev.* 10: 1443–1454.

Zeng, L., Fagotto, F., Zhang, T., Hsu, W., Vasicek, T. J., III, P. W. L., Lee, J. J., Tilghman, S. M., Gumbiner, B. M., and Costantini, F. (1997) "The mouse Fused locus encodes Axin, an inhibitor of the Wnt signaling pathway that regulates embryonic axis formation." *Cell* 90: 181–192.

What is claimed is:

1. An isolated nucleic acid which encodes an axin polypeptide selected from the group consisting of human axin (SEQ ID NO: 4) and mouse axin (SEQ ID NO: 1).

2. The isolated nucleic acid of claim 1, wherein the nucleic acid is DNA.

3. The isolated nucleic acid of claim 2, wherein the nucleic acid is cDNA.

4. The isolated nucleic acid of claim 1, wherein the axin polypeptide is mouse axin.

5. The isolated nucleic acid of claim 1, wherein the axin polypeptide is human axin.

6. The isolated nucleic acid of claim 4, wherein the nucleic acid comprises SEQ ID NO:2.

7. The isolated nucleic acid of claim 5, wherein the nucleic acid comprises SEQ ID NO:3.

8. An isolated nucleic acid which encodes a vertebrate axin polypeptide which negatively regulates the Wnt signaling pathway and specifically hybridizes to a nucleic acid complementary to a nucleic acid of claim 1.

9. An isolated nucleic acid which comprises at least 50 nucleotides in length which have a sequence complementary to the sequence of the isolated nucleic acid of claim 1.

10. An isolated nucleic acid which encodes a mutant axin polypeptide which: (a) has a sequence identical to that of a wildtype axin polypeptide except for a deletion of a segment of amino acid residues, wherein the wildtype polypeptide is mouse Axin (SEQ ID NO: 1) and the deleted amino acid residues comprise amino acid residues 213–338 set forth in SEQ ID NO: 1; and (b) activates the Wnt signaling pathway.

11. An isolated nucleic acid which encodes a mutant axin polypeptide which: (a) has a sequence identical to that of a wildtype axin polypeptide except for a deletion of a segment of amino acid residues, wherein the wildtype polypeptide is human Axin (SEQ ID NO: 4) and the deleted amino acid residues comprise amino acid residues 121–247 set forth in SEQ ID NO: 4; and (b) activates the Wnt signaling pathway.

12. A vector comprising the isolated nucleic acid of claim 1.

13. The vector of claim 12, further comprising a promoter of RNA transcription operatively linked to the nucleic acid.

14. The vector of claim 12, wherein the promoter comprises a bacterial, yeast, insect or mammalian promoter.

15. The vector of claim 12, further comprising plasmid, cosmid, yeast artificial chromosome (YAC), bacteriophage or eukaryotic viral DNA.

16. A host vector system for the production of a polypeptide which comprises the vector of claim 12 in a suitable host.

17. The host vector system of claim 16, wherein the suitable host is a prokaryotic or eukaryotic cell.

18. The host vector system of claim 17, wherein the prokaryotic cell is a bacterial cell.

19. The host vector system of claim 17, wherein the eukaryotic cell is a yeast, insect, plant or mammalian cell.

20. A method for producing a polypeptide which comprises growing the host vector system of claim 16 under suitable conditions permitting production of the polypeptide and recovering the polypeptide so produced.

21. A method of obtaining a polypeptide in purified form which comprises:

(a) introducing the vector of claim 12 into a suitable host cell;

(b) culturing the resulting cell so as to produce the polypeptide;

(c) recovering the polypeptide produced in step (b); and (d) purifying the polypeptide so recovered.

22. The isolated nucleic acid of claim 1, wherein the nucleic acid is RNA.

* * * * *